(12) United States Patent
Hu et al.

(10) Patent No.: US 8,455,522 B2
(45) Date of Patent: *Jun. 4, 2013

(54) BENZOXAZOLONE DERIVATIVES AS ALDOSTERONE SYNTHASE INHIBITORS

(75) Inventors: Qi-Ying Hu, Cambridge, MA (US); Julien Papillon, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/319,768

(22) PCT Filed: May 12, 2010

(86) PCT No.: PCT/EP2010/056529
§ 371 (c)(1),
(2), (4) Date: Nov. 10, 2011

(87) PCT Pub. No.: WO2010/130773
PCT Pub. Date: Nov. 18, 2010

(65) Prior Publication Data
US 2012/0071514 A1    Mar. 22, 2012

Related U.S. Application Data

(60) Provisional application No. 61/178,680, filed on May 15, 2009, provisional application No. 61/327,221, filed on Apr. 23, 2010.

(51) Int. Cl.
*A61K 31/443* (2006.01)
*C07D 413/02* (2006.01)

(52) U.S. Cl.
USPC ........................................ 514/338; 546/271.7

(58) Field of Classification Search
USPC ........................................ 514/338; 546/271.7
See application file for complete search history.

(56) References Cited

U.S. PATENT DOCUMENTS

| | | | |
|---|---|---|---|
| 6,831,175 B2 | 12/2004 | Li et al. | |
| 2003/0187026 A1 | 10/2003 | Li et al. | |
| 2003/0199511 A1 | 10/2003 | Li et al. | |
| 2006/0247441 A1 | 11/2006 | Wilk | |
| 2007/0027327 A1 | 2/2007 | Wu et al. | |
| 2007/0191447 A1* | 8/2007 | Kodo et al. | 514/395 |
| 2009/0048322 A1 | 2/2009 | Chow et al. | |

FOREIGN PATENT DOCUMENTS

| | | |
|---|---|---|
| EP | 1719761 A1 | 11/2006 |
| WO | 00/64872 A1 | 11/2000 |
| WO | 03/051366 A2 | 6/2003 |
| WO | 03/086467 A1 | 10/2003 |
| WO | 2005/080334 A1 | 9/2005 |
| WO | 2006/066133 A2 | 6/2006 |
| WO | 2007/024949 A2 | 3/2007 |
| WO | 2009/023179 A2 | 2/2009 |
| WO | 2009/135651 A1 | 11/2009 |
| WO | 2009/156462 A2 | 12/2009 |
| WO | 2010/130773 A2 | 11/2010 |
| WO | 2010/130794 A1 | 11/2010 |
| WO | 2010/130796 A1 | 11/2010 |

OTHER PUBLICATIONS

Lucas et al., "In Vivo Active Aldosterone Synthase Inhibitors with Improved Selectivity: Lead Optimization Providing a Series of Pyridine Substituted 3, 4-Dihydro-1H-quinolin-2-one Derivatives," Journal of Medicinal Chemistry 51 (24):8077-8087 (Dec. 25, 2008).
Adams et al.; "Mapping the Kinase Domain of Janus Kinase 3"; Bioorganic & Medicinal Chemistry Letters; 13:3105-3110 (2003).
Ellis et al.; "A Versatile Synthesis of Unsymmetrical 3,3'-Bioxindoles: Stereoselective Mukaiyama Aldol Reactions of 2-Siloxyindoles with Isatins"; J. Org. Chem.; 73:9151-9154 (2008).
McAllister et al.; "A Fluorous-Phase Pummerer Cyclative-Capture Strategy for the Synthesis of Nitrogen Heterocycles"; Angew. Chem. Int. Ed.—Communications; 44:452-455 (2005).
McAllister et al.; "A Fluorous, Pummerer Cyclative-Capture Strategy for the Synthesis of N-Heterocycles"; Chem. Eur. J.; 13:1032-1046 (2007).
RN 1194452-52-2, RN 1194452-50-0, RN 1194452-19-1, RN 1194452-17-9, RN 1194452-15-7 and RN 1194452-13-5, Nov. 30, 2009.
Zhu et al.; "Discovery and SAR of oxindole—pyridine-based protein kinase B/Akt inhibitors for treating cancers"; Bioorganic & Medicinal Chemistry Letters; 16:3424-3429 (2006).

* cited by examiner

*Primary Examiner* — Samantha Shterengarts
(74) *Attorney, Agent, or Firm* — Sophie Binet Cross

(57) ABSTRACT

The present invention provides a compound of formula I;

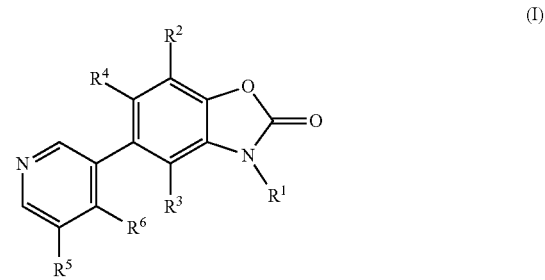

a method for manufacturing the compounds of the invention, and its therapeutic uses. The present invention further provides a combination of pharmacologically active agents and a pharmaceutical composition.

10 Claims, No Drawings

BENZOXAZOLONE DERIVATIVES AS ALDOSTERONE SYNTHASE INHIBITORS

This application is a U.S. National Phase filing of International Serial No. PCT/EP2010/056529 filed May 12, 2010, and claims priority to U.S. provisional application Ser. No. 61/327,221 filed Apr. 23, 2010 and Ser. No. 61/178,680 filed May 15, 2009, the contents of which are incorporated herein by reference in their entirety.

BACKGROUND OF THE INVENTION

The mineralocorticoid hormone aldosterone is produced by the adrenal gland and acts on the distal tubules and collecting ducts of the kidney to increase reabsorption of ions and water in the kidney. Aldosterone causes conservation of sodium, secretion of potassium, increased water retention, and increased blood pressure.

Aldosterone has been implicated in the pathogenesis of cardiovascular diseases such as hypertension and heart failure. In clinical trials, treatment with the nonselective mineralocorticoid receptor antagonist (MRA) spironolactone or the selective MRA eplerenone significantly reduced morbidity and mortality among patients with heart failure or myocardial infarction already taking an angiotensin-converting enzyme inhibitor or a β-blocker. However, significant side effects such as gynecomastia and impotence were observed in male patients receiving spironolactone while hyperkalemia was seen in patients taking either drug.

SUMMARY OF THE INVENTION

The invention pertains to the compounds, methods for using them, and uses thereof as described herein. Examples of compounds of the invention include the compounds of Formulae I-III, and the compounds of the examples.

The invention therefore provides a compound of the Formula I:

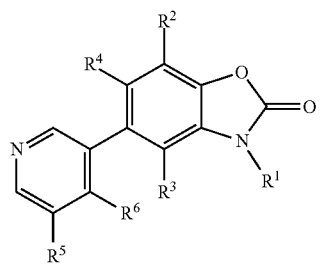

(I)

or a pharmaceutically acceptable salt thereof, wherein:

$R^1$ is $C_{1-7}$alkyl, $C_{6-10}$aryl-$C_{1-7}$alkyl, hydroxy-$C_{1-7}$alkyl, $C_{3-8}$cycloalkyl or —$CH_2C(O)NR^8R^9$;

$R^2$ and $R^4$ are each independently hydrogen or halogen;

$R^3$ is hydrogen or $C_{1-7}$alkoxy;

$R^5$ is hydrogen, halogen, $C_{1-7}$alkoxy, $C_{1-7}$alkyl, $C_{3-8}$cycloalkyl, cyano, —$CH_2NR^8R^9$, —$CH_2NR^8(SO_2)$—$C_{1-7}$alkyl, —$CH_2NR^8(SO_2)$—$C_{3-8}$cycloalkyl, —$NR^8(SO_2)$—$C_{1-7}$alkyl, —$NR^8(SO_2)$—$C_{3-8}$cycloalkyl or —$NHC(O)NR^8R^9$; in which each alkyl and cycloalkyl is optionally substituted with one or more substituents selected from the group consisting of $C_{1-7}$alkoxy, halogen, hydroxy, —$NH_2$, —$NH(C_{1-7}$alkyl) and —$N(C_{1-7}$alkyl)$_2$;

$R^6$ hydrogen, $C_{1-7}$alkyl, $C_{3-8}$cycloalkyl, heterocyclyl, —$C(O)$—$C_{1-7}$alkyl, —$C(O)NR^8R^9$, —$C_{1-7}$alkyl-$NR^8C(O)$—$C_{1-7}$alkyl, —$CH_2NR^8(SO_2)$—$C_{1-7}$alkyl-$NR^8$—$S(O)_n$—$C_{1-7}$alkyl, —$CH_2NR^8$—$S(O)_n$—$C_{3-8}$cycloalkyl or —$CH_2NR^8(SO_2)$—$C_{1-7}$alkyl; in which each alkyl and cycloalkyl is optionally substituted with one or more substitutents selected from the group consisting of $C_{6-10}$aryl, $C_{1-7}$alkoxy, halogen, hydroxy and —$NH_2$, —$NH(C_{1-7}$alkyl) and —$N(C_{1-7}$alkyl)$_2$; and $R^8$ and $R^9$ are each independently hydrogen, $C_{1-7}$alkyl or $C_{6-10}$aryl-$C_{1-7}$alkyl; and n is 1 or 2;

wherein each heteroaryl is a mono- or bicyclic aromatic moiety comprising 5-10 ring atoms selected from carbon atoms and 1 to 5 heteroatoms, and each heterocyclyl is a mono- or bicyclic saturated or partially saturated but non-aromatic moiety comprising 4-10 ring atoms selected from carbon atoms and 1 to 5 heteroatoms; and each heteroatoms being O, N or S.

In another embodiment, the invention pertains, at least in part, to a method for treating a disorder or disease mediated by aldosterone synthase and/or 11-beta hydroxylase (CYP11B1) in a subject by administering to the subject a therapeutically effective amount of a compound according to any one of Formulae I-III, or a pharmaceutically acceptable salt thereof, such that the disorder or disease mediated by aldosterone synthase and/or CYP11B1 in the subject is treated.

In yet another embodiment, the invention pertains, at least in part, to a method for treating a subject for hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess, comprising administering to the subject a therapeutically effective amount of a compound according to any one of Formulae I-III, or a pharmaceutically acceptable salt thereof, such that the subject is treated.

In yet another embodiment, the invention pertains, at least in part, to pharmaceutical compositions, comprising an effective amount of a compound according to any one of Formulae I-III, or a pharmaceutically acceptable salt thereof, wherein said effective amount is effective to treat a disorder or disease mediated by aldosterone synthase and/or CYP11B1.

In still another embodiment, the invention pertains, at least in part, to combinations including pharmaceutical combinations of one or more therapeutically active agents.

In another embodiment, the invention pertains, at least in part, to a method for inhibiting aldosterone synthase and/or CYP11B1 in a subject by administering to the subject a therapeutically effective amount of a compound according to any one of Formulae I-III, or a pharmaceutically acceptable salt thereof, such that aldosterone synthase and/or CYP11B1 is inhibited.

An alternative approach to ameliorate the deleterious effects of aldosterone, provided by the present invention, is the suppression of aldosterone production by aldosterone synthase inhibitors. Aldosterone synthase is an enzyme responsible for the final steps of the biosynthesis of aldosterone from deoxycorticosterone, via conversion of corticosterone to form 18-OH-corticosterone, which is then converted to aldosterone.

Accordingly, the invention pertains, at least in part, to compounds, pharmaceutical compositions containing the compound and methods of use thereof. The present invention also relates to novel compounds which may be used, for example, as modulators and/or inhibitors of aldosterone synthase and/or CYP11B1.

The compounds of the present invention may, for example, be used to treat various diseases or disorders hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess.

DETAILED DESCRIPTION OF THE INVENTION

Compounds of the Invention

References hereinafter to compounds of Formula I apply equally to compounds of Formulae II and III.

References hereinafter to embodiments of the invention apply equally to compounds of Formula I and compounds of Formulae II and III, insofar as the embodiments are present.

Various embodiments of the invention are described herein. It will be recognized that features specified in each embodiment may be combined with other specified features to provide further embodiments.

In one embodiment the invention provides a compound of the Formula I

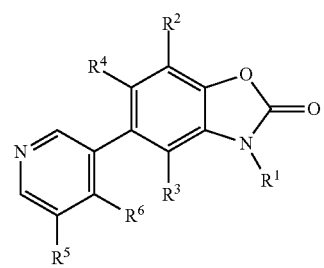

(I)

or a pharmaceutically acceptable salt thereof, wherein:
$R^1$ is $C_{1-7}$alkyl, $C_{6-10}$aryl-$C_{1-7}$alkyl, hydroxy-$C_{1-7}$alkyl, $C_{3-8}$cycloalkyl or —$CH_2C(O)NR^8R^9$;
$R^2$ and $R^4$ are each independently hydrogen or halogen;
$R^3$ is hydrogen or $C_{1-7}$alkoxy;
$R^5$ is hydrogen, halogen, $C_{1-7}$alkoxy, $C_{1-7}$alkyl, $C_{3-8}$cycloalkyl, cyano. —$CH_2NR^8R^9$, —$CH_2NR^8(SO_2)$—$C_{1-7}$alkyl, —$CH_2NR^8(SO_2)$—$C_{3-8}$cycloalkyl, —$NR^8(SO_2)$—$C_{1-7}$alkyl, —$NR(SO_2)$—$C_{3-8}$cycloalkyl or —$NHC(O)NR^8R^9$; in which each alkyl and cycloalkyl is optionally substituted with one or more substitutents selected from the group consisting of $C_{1-7}$alkoxy, halogen, hydroxy, —$NH_2$, —$NH(C_{1-7}$alkyl) and —$N(C_{1-7}$alkyl)$_2$;
$R^6$ hydrogen, $C_{1-7}$alkyl, $C_{3-8}$cycloalkyl, heterocyclyl, —$C(O)$—$C_{1-7}$alkyl, —$C(O)NR^8R^9$, —$C_{1-7}$alkyl-$NR^8C(O)$—$C_{1-7}$alkyl, —$CH_2NR^8(SO_2)$—$C_{1-7}$alkyl, —$C_{1-7}$alkyl-$NR^8$—$S(O)_n$—$C_{1-7}$alkyl, —$CH_2NR^8$—$S(O)_n$—$C_{3-8}$cycloalkyl or —$CH_2NR^8(SO_2)$—$C_{1-7}$alkyl; in which each alkyl and cycloalkyl is optionally substituted with one or more substitutents selected from the group consisting of $C_{6-10}$aryl, $C_{1-7}$alkoxy, halogen, hydroxy and —$NH_2$, —$NH(C_{1-7}$alkyl) and —$N(C_{1-7}$alkyl)$_2$; and
$R^8$ and $R^9$ are each independently hydrogen, $C_{1-7}$alkyl or $C_{6-10}$aryl-$C_{1-7}$alkyl; and n is 1 or 2;
wherein each heteroaryl is a mono- or bicyclic aromatic moiety comprising 5-10 ring atoms selected from carbon atoms and 1 to 5 heteroatoms, and
each heterocyclyl is a mono- or bicyclic saturated or partially saturated but non-aromatic moiety comprising 4-10 ring atoms selected from carbon atoms and 1 to 5 heteroatoms, and each heteroatoms being O, N or S.

Certain compounds of Formula I include compounds of Formula II:

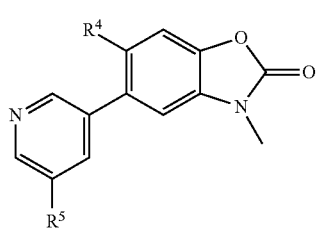

(II)

or a pharmaceutically acceptable salt thereof, wherein $R^4$ and $R^6$ have the definitions of Formula I; supra.

In one particular aspect of this embodiment, $R^4$ is H or halo (e.g. chloro, fluoro, bromo).

In yet another aspect of this embodiment, are compounds of Formula II, or a pharmaceutically acceptable salt thereof, in which $R^5$ is hydrogen, halogen, $C_{1-7}$alkyl or $C_{3-8}$cycloalkyl in which alkyl and cycloalkyl are optionally substituted with hydroxy, halogen or amino (e.g., —NH$_2$, —NH—C$_{1-7}$alkyl or —N(C$_{1-7}$alkyl)$_2$).

Certain compounds of Formula I include compounds of Formula III:

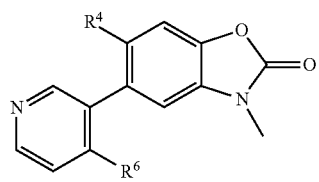

(III)

or a pharmaceutically acceptable salt thereof, wherein $R^4$ and $R^6$ have the definitions of Formula I, supra.

In one aspect of this embodiment, $R^4$ is H or halo (e.g. chloro, fluoro, bromo).

In yet another aspect of this embodiment, are compounds of Formula III, or a pharmaceutically acceptable salt thereof, in which $R^6$ is hydrogen, halogen, $C_{1-7}$alkyl or $C_{3-8}$cycloalkyl in which alkyl and cycloalkyl are optionally substituted with hydroxy, halogen, $C_{1-7}$alkoxy, $C_{6-10}$aryl or amino (e.g., —NH$_2$, —NH—C$_{1-7}$alkyl or —N(C$_{1-7}$alkyl)$_2$).

In another aspect of this embodiment, $R^6$ is $C_{1-7}$alkyl substituted with halogen hydroxy.

In yet another aspect of this embodiment are compounds of Formula III in which $R^4$ is H and $R^6$ is hydroxy-$C_{1-7}$alkyl.

In another embodiment, the invention pertains to compounds of Formula I wherein $R^1$ is $C_{1-7}$ alkyl (e.g., methyl, ethyl, propyl), or

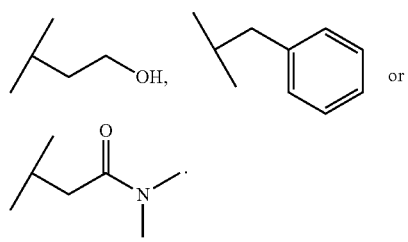

In one embodiment, the invention pertains to compounds of Formula I or other classes and subclasses described herein, or a pharmaceutically acceptable salt thereof, wherein $R^2$ is hydrogen. In another embodiment $R^2$ is halogen (e.g., fluoro, chloro, bromo or iodo).

In one embodiment, one of $R^2$ and $R^4$ is hydrogen and the other is hydrogen or halogen (e.g., fluorine, chlorine, bromine or iodine).

In another embodiment, $R^3$ is hydrogen. In yet another embodiment $R^3$ is $C_{1-7}$alkoxy methoxy or ethoxy).

In yet another embodiment, the invention pertains to compounds according to anyone of Formulae I, II and III, or other classes and subclasses described herein, or a pharmaceutically acceptable salt thereof, wherein $R^4$ is H or halogen. In one aspect of this embodiment $R^4$ is H. In a further aspect of this embodiment, $R^4$ is H and $R^6$ is $C_{1-7}$alkyl substituted with hydroxy.

In another embodiment, the invention pertains to compounds of Formulae I or II or other classes and subclasses described herein, or a pharmaceutically acceptable salt of, wherein $R^5$ is hydrogen, cyano, halogen (e.g., fluoro, chloro, bromo or iodo), or $C_{1-7}$alkoxy methoxy or ethoxy). In one aspect of this embodiment, $R^5$ is hydrogen, halogen, $C_{1-7}$alkyl or $C_{3-8}$cycloalkyl in which alkyl and cycloalkyl are optionally substituted with one are more substitutents selected from the group consisting of $C_{1-7}$alkoxy, halogen, hydroxy, —NH$_2$, —NH(C$_{1-7}$alkyl) and —N(C$_{1-7}$alkyl)$_2$.

In another embodiment, $R^5$ is $C_{1-7}$alkyl or $C_{3-8}$cycloalkyl, each of which is independently substituted with hydroxy, amino (e.g., —NH$_2$, —NH—C$_{1-7}$alkyl or —N(C$_{1-7}$alkyl)$_2$), and/or halogen. Representative examples of this embodiment include compounds according to any one of Formulae I and II or of other Formulae, classes and subclasses described herein, or a pharmaceutically acceptable salt thereof, in which $R^5$ is:

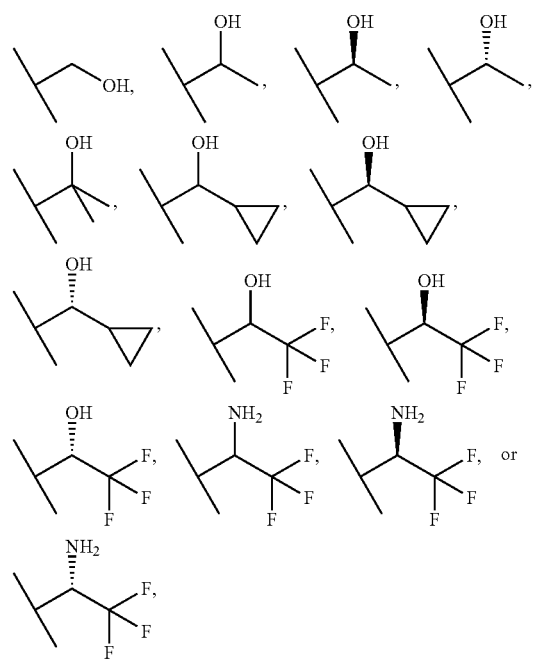

In yet another embodiment, the invention pertains to compounds according to any one of Formulae I and II or other classes and subclasses described herein, or a pharmaceutically acceptable salt thereof, wherein $R^5$ is —CH$_2$NR$^8$R$^9$. Representative examples of this embodiment include compounds of Formula I, or of other Formulae, classes and subclasses described herein, in which $R^5$ is:

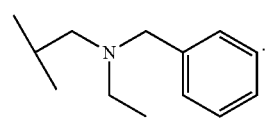

In yet another embodiment, $R^5$ is —CH$_2$NR$^8$(SO$_2$)—C$_{1-7}$alkyl or —CH$_2$NR$^8$(SO$_2$)—C$_{3-8}$cycloalkyl, in which alkyl is optionally substituted as defined in Formula I. Representative examples of this embodiment include compounds of Formula I, or of other Formulae, classes and subclasses described herein, or a pharmaceutically acceptable salt thereof, in which $R^5$ is

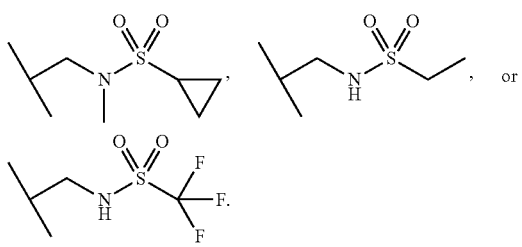

In yet another embodiment, $R^5$ is —NHC(O)NR$^8$R$^9$, for example:

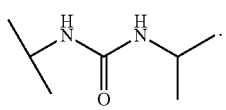

In yet another embodiment, $R^5$ is —NR$^8$(SO$_2$)—C$_{1-7}$alkyl, or NR$^8$(SO$_2$)—C$_{3-8}$cycloalkyl, in which alkyl is optionally substituted as defined in Formula I. Representative examples of this embodiment include compounds of Formula I, or of other Formulae, classes and subclasses described herein, or a pharmaceutically acceptable salt thereof, in which $R^5$ is:

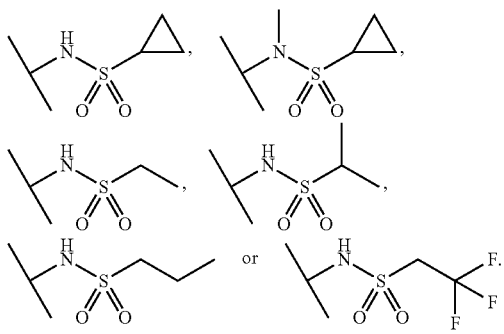

In one embodiment, $R^6$ is hydrogen, C$_{1-7}$alkyl (e.g., methyl, ethyl), C$_{1-7}$alkyl substituted with hydroxy (e.g. hydroxyalkyl), C$_{1-7}$alkyl substituted with C$_{6-10}$aryl (e.g. arylalkyl), C$_{1-6}$alkyl substituted with halogen (e.g. haloalkyl) or C$_{1-7}$alkyl substituted with C$_{1-7}$alkoxy (e.g. alkoxyalkyl). In one particular aspect of this embodiment $R^6$ is H or hydroxy-C$_{1-7}$alkyl.

In another embodiment, $R^6$ is C$_{1-7}$alkyl or C$_{3-8}$cycloalkyl each of which is independently substituted with hydroxy, halogen or C$_{6-10}$aryl. Representative examples of this embodiment include compounds of Formula I, or of other Formulae, classes and subclasses described herein, or a pharmaceutically acceptable salt thereof, in which $R^6$ is a hydroxy-C$_{1-7}$alkyl or C$_{6-10}$aryl-C$_{1-7}$alkyl of the following types:

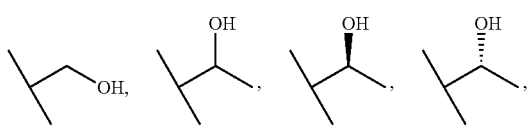

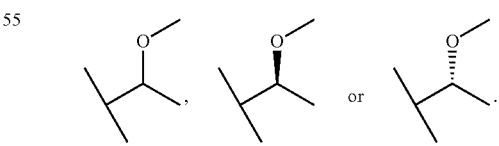

In another embodiment, $R^6$ is C$_{1-6-7}$alkyl substituted with amino (e.g., —NH$_2$, —NH—C$_{1-7}$alkyl or —N(C$_{1-7}$allyl)$_2$), and/or halogen. Representative examples of this embodiment include compounds of Formula I, or of other Formulae, classes and subclasses described herein, or a pharmaceutically acceptable salt thereof, in which $R^6$ is:

In another embodiment, $R^6$ is heterocyclyl, for example:

In another embodiment, $R^6$ is C$_{1-7}$alkyl substituted with C$_{1-7}$alkoxy (alkoxyalkyl). Representative examples of this embodiment include compounds of Formula I, or of other Formulae, classes and subclasses described herein, or a pharmaceutically acceptable salt thereof, in which $R^6$ is:

In yet another embodiment, $R^6$ is —CH$_2$—NR$^8$(SO$_2$)—C$_{1-7}$alkyl, in which alkyl is optionally substituted as defined in Formula I. Representative examples of this embodiment include compounds of Formula I, or of other Formulae, classes and subclasses described herein, or a pharmaceutically acceptable salt thereof, in which $R^6$ is:

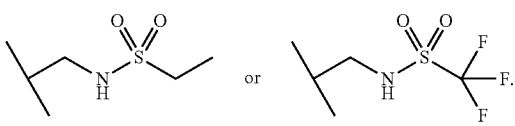

In yet another embodiment, $R^6$ is —C(O)C$_{1-4}$alkyl or —C(O)NR$^8$R$^9$. Representative examples of this embodiment include compounds of Formula I, or of other Formulae, classes and subclasses described herein, or a pharmaceutically acceptable salt thereof, in which $R^6$ is:

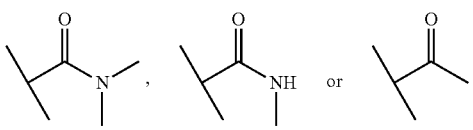

In yet another embodiment, $R^6$ is —C$_{1-7}$alkyl-NR$^8$C(O)—C$_{1-7}$alkyl or —C$_{1-7}$alkyl-NR$^8$S(O)$_n$—C$_{1-7}$alkyl, in which alkyl is optionally substituted as defined in Formula I. For example, $R^6$ is —CH(halo-C$_{1-7}$alkyl)NR$^8$C(O)—C$_{1-7}$alkyl or —CH(halo-C$_{1-7}$alkyl)NR$^8$S(O)$_n$C$_{1-7}$alkyl. Representative examples of this embodiment include compounds of Formula I, or of other Formulae, classes and subclasses described herein, or a pharmaceutically acceptable salt thereof, in which $R^6$ is:

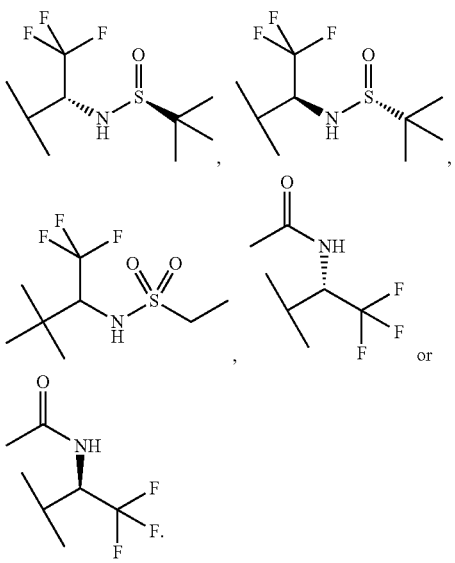

In still another embodiment, examples of $R^8$ and $R^9$ include C$_{1-7}$alkyl (e.g. methyl, ethyl, isopropyl) or hydrogen.

In another embodiment the $R^1$-$R^9$ and n variables are those defined by the $R^1$-$R^9$ variables, respectively, in Examples 1 to 40 in the Examples section below.

In another embodiment individual compound according to the invention are those listed in Examples 1 to 40 in the Examples section below, or a pharmaceutically acceptable salt thereof.

DEFINITION

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl. The term "C$_{1-7}$alkyl" refers to a hydrocarbon having one to seven carbon atoms. Moreover, the term alkenyl includes both "unsubstituted alkyls" and "substituted alkyls".

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-C$_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tart-butoxy, pentyloxy, hexyloxy, cyclopropyloxy-, cyclohexyloxy- and the like. Preferably, alkoxy groups have about 1-7, more preferably about 1-4 carbons. The term alkoxy include substituted alkoxy. Examples of substituted alkoxy groups include halogenated alkoxy groups. Examples of halogen substituted alkoxy groups are fluoromethoxy, difluoromethoxy, trifluoromethoxy, chloromethoxy, dichloromethoxy, and trichloromethoxy. The term "C$_{1-7}$alkoxy" refers to C$_{1-7}$alkyl-O—, wherein C$_{1-7}$alkyl is defined above. Moreover, the term alkoxy includes both "unsubstituted alkoxy" and "substituted alkoxy".

The term alkoxyalkyl refers to an alkyl group, as defined above, in which the alkyl group is substituted with alkoxy. The term also includes substituted alkoxyalkyl moiety.

The term "alkenyl" refers to a branched or unbranched hydrocarbon having at least one carbon-carbon double bond. The term "C$_{2-7}$alkenyl" refers to a hydrocarbon having two to seven carbon atoms and comprising at least one carbon-carbon double bond. Representative examples of alkenyl are vinyl, prop-1-enyl, allyl, butenyl, isopropenyl or isobutenyl. Moreover, the term alkenyl includes both "unsubstituted alkenyls" and "substituted alkenyls".

The term "alkenyoxy" refer to alkenyl-O— wherein alkenyl has the definition above.

The term "alkynyl" refers to a branched or unbranched hydrocarbon having at least one carbon-carbon triple bond. The term "C$_{2-7}$-alkynyl" refers to a hydrocarbon having two to seven carbon atoms and comprising at least one carbon-carbon triple bond. Representative examples of alkynyl are ethynyl, prop-1-ynyl (propargyl), butynyl, isopropynyl or isobutynyl. Moreover, the term alkynyl includes both "unsubstituted alkynyls" and "substituted alkynyls".

As used herein, the term "cycloalkyl" refers to saturated or partially unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2] octyl. Exemplary tricyclic hydrocarbon groups include adamantyl. The term "$C_{3-3}$ cycloalkyl" refers to a cyclic hydrocarbon groups having 3 to 8 carbon atoms.

The term "cycloalkylalkyl" refers to an alkyl substituted with cycloalkyl.

The term "cycloalkylalkyl" refers to an alkyl as defined above substituted with a cycloakyl as defined above.

The alkyl, alkenyl, alkynyl, alkoxy and cycloalkyl groups may be optionally substituted with one or more substituents Representative examples of substituents for alkyl, alkenyl, alkynyl, alkoxy and cycloalkyl moities are oxo, =S, halogen, hydroxy, cyano, nitro, alkyl, alkenyl, akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminoacarbonyl, dialkylaminocarbonyl, arylalkyl, heteroarylalkyl, heterocyclylalkyl, aminocarbonyl, alkenylaminocarbonyl, alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

The term "aryl" refers to monocyclic or bicyclic aromatic hydrocarbon groups having 6-20 carbon atoms in the ring portion. Preferably, the aryl is a ($C_{6-10}$aryl). The term aryl also refers to a group in which an aromatic ring is fused to one or more cycloalkyl rings, where the point of attachment is on the aromatic ring or on the fused cycloalkyl ring. Representative examples of aryl are phenyl, naphthyl, anthracyl, phenanthryl or tetrahydronaphthyl. The term "$C_{6-10}$ aryl" refers to an aromatic hydrocarbon groups having 6 to 10 carbon atoms in the ring portion. Moreover, the term aryl includes both "unsubstituted aryl" and "substituted aryl".

The term "arylalkyl" is an alkyl substituted with aryl. Representative examples of arylalkyl are benzyl or Phenyl-CH$_2$CH$_2$—. The term also includes substituted arylalkyl moiety.

The term "Heteroaryl" includes monocyclic or bicyclic heteroaryl, containing from 5-10 ring members selected from carbon atoms and 1 to 5 heteroatoms, and each heteroatoms is selected from O, N or S. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3, 4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl, cycloaliphatic, or heterocyclyl rings, where the radical or point of attachment is on the heteroaromatic ring or on the fused aryl, cycloaliphatic or heterocyclyl rings. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo [4,5-c]pyridinyl, pyrazolo[4,3-c]]pyridinyl, pyrazolo[4,3-c] pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4, 3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

The term "heteroarylakyl" refers to alkyl substituted with heteroaryl. The term also includes substituted heteroarylalkyl moiety.

The aromatic ring of an "aryl" or "heteroaryl" group can be substituted at one or more ring positions with such substituents as described above, as for example, halogen, hydroxy, cyano, nitro, alkyl, alkenyl, akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminoacarbonyl, dialkylaminocarbonyl, arylalkyl, heteroarylalkyl, heterocyclylalkyl, aminocarbonyl, alkenylaminocarbonyl, alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

As used herein, the term "heterocyclyl" or "heterocyclo" refers to a saturated or unsaturated non-aromatic ring (partially unsaturated) or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "heterocyclyl" includes heterocyclic groups as defined herein substituted with 1, 2 or 3 substituents such as alkyl, hydroxy (or protected hydroxy), halo, oxo (e.g., =O), amino, alkylamino or dialkylamino, alkoxy, cycloalkyl, carboxyl, heterocyclooxy, wherein heterocyclooxy denotes a heterocyclic group bonded through an oxygen bridge, alkyl-O—C(O)—, mercapto, nitro, cyano, sulfamoyl or sulfonamide, aryl, alkyl-C(O)—O—, aryl-C(O)—O—, aryl-S—, aryloxy, alkyl-S—, formyl (e.g., HC(O)—), carbamoyl, arylalkyl-, and aryl substituted with alkyl, cycloalkyl, alkoxy, hydroxy, amino, alkyl-C(O)—NH—, alkylamino, dialkylamino or halogen.

The term "heterocyclylalkyl" is an alkyl substituted with heterocyclyl. The term include substituted heterocyclylalkyl moiety.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfonyl, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy. The term also includes substituted aroyl moieties. The term "substituted aroyl" includes aroyl groups where one or more of the hydrogen atoms are replaced by for example, halogen, hydroxy, cyano, nitro, alkyl, alkenyl, akynyl, alkoxy, alkenyloxy, alkynyloxy, halogen, alkylcarbonyl, alkylcarbonyloxy, arylcarbonyl, arylcarbonyloxy, alkoxycarbonyloxy, aryloxycarbonyloxy, carboxylate, alkylcarbonyl, alkylaminocarbonyl, dialkylaminocarbonyl, arylalkyl, heteroarylalkyl, heterocyclylalkyl, aminocarbonyl, alkenylaminocarbonyl, alkoxycarbonyl, alkylcarbonyl, dialkylaminocarbonyl, arylcarbonyl, arylalkylcarbonyl, alkenylcarbonyl, alkoxycarbonyl, alkylcarbonylamino, alkylcarbonylalkylamino, aminocarbonyl, alkylthiocarbonyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, aminosulfonyl, alkylsulfonyl, arylsulfonyl, sulfhydryl, alkylthio, arylthio, thiocarboxylate, sulfates, alkylsulfinyl, sulfamoyl, sulfonamido, heterocyclyl, or an aromatic or heteroaromatic moiety, wherein each of the afore-mentioned hydrocarbon groups may be optionally substituted with one or more halogen, hydroxy or $C_{1-7}$alkoxy groups.

The terms "alkoxyalkyl," include alkyl groups, as described above, in which the alkyl group is substituted with an alkoxy as defined above. The term includes substituted alkoxyalkyl moiety.

The term "hydroxyalkyl" refers to alkyl groups, as described above, in which the alkyl group is substituted with a hydroxy. The term includes substituted hydroxyalkyl moiety.

The term "hydroxycycloalkyl" refers to a cycloalkyl, as described above, in which the cycloalkyl is substituted with hydroxy. The term includes substituted hydroxycycloalkyl moiety.

The term "hydroxycycloalkylalkyl" refers to a cycloalkylalkyl, as defined above, in which the cycloalkylakyl is substituted with hydroxy. The term includes substituted hydroxycycloalkylalkyl moiety.

The term "carbamoyl" includes $H_2NC(O)$—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O), alkyl(aryl-alkyl)-NC(O)—. The term includes substituted carbamoyl moieties.

The term "sulfonyl" includes R—$SO_2$—, wherein R is hydrogen, alkyl, aryl, heteroaryl, aryl-alkyl, heteroaryl-alkyl, alkoxy, aryloxy, cycloalkyl, or heterocyclyl.

The term "sulfonamido" includes alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)-. The term includes substituted carbamoyl moieties The term "sulfamoyl" includes $H_2NS(O)_2$—, alkyl-NHS(O)$_2$—, (alkyl)$_2$NS(O)$_2$—, NHS(O)$_2$—, alkyl(aryl)-NS(O)$_2$—, (aryl)$_2$NS(O)$_2$—, heteroaryl-NHS(O)$_2$, (aryl-alkyl)-NHS(O)$_2$—, (heteroarykalkyl)-NHS(O)$_2$—. The term includes substituted sulfamoyl moieties.

The term "aryloxy" includes an —O-aryl, wherein aryl is defined herein. The term includes substituted aryloxy moieties.

The term "heteroaryloxy" includes an —O-heteroaryl moiety, wherein heteroaryl is defined herein. The term includes substituted heteroaryloxy moieties.

The term heterocyclyloxy includes an —O-heterocyclyl, wherein heterocyclyl is defined herein. The term includes substituted heterocyclyloxy moieties.

The term "amine" or "amino" includes compounds where a nitrogen atom is covalently bonded to at least one carbon or heteroatom. The term "amine" or "amino" also includes —$NH_2$ and also includes substituted moieties. The term includes "alkyl amino" which comprises groups and compounds wherein the nitrogen is bound to at least one additional alkyl group. The term includes "dialkyl amino" groups wherein the nitrogen atom is bound to at least two additional independently selected alkyl groups. The term includes "arylamino" and "diarylamino" groups wherein the nitrogen is bound to at least one or two independently selected aryl groups, respectively.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." The term "amide," "amido" or "aminocarbonyl" also includes substituted moieties.

The term "carbonyl" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom. The term also includes substituted moieties.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group. The term also includes substituted moieties.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above. The term also includes substituted moieties.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group. The term also includes substituted moieties.

The term "hydroxy" or "hydroxyl" includes groups with an —OH.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxy, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxy, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen and sulfur.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate, "Diastereoisomers" are stereoisomers that have at least two asymmetric atoms, but which are not mirror-images of each other. The absolute stereochemistry is specified according to the Cahn-Ingold-Prelog R-S system. When compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 60% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like, particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1H$, $^2H$ or D, $^3H$); any carbon represented by "C" in any of the formulae herein is intended to represent all isotopic forms of carbon (e.g. $^{11}C$, $^{13}C$, $^{14}C$); any nitrogen represented by "N" is intended to represent all isotopic forms of nitrogen (e.g. $^{14}N$, $^{15}N$). Other examples of isotopes that are included in the invention include isotopes of oxygen, sulfur, phosphorous, fluorine, iodine and chlorine, such as $^{18}F$ $^{31}P$, $^{32}P$, $^{35}S$, $^{36}Cl$, $^{125}I$. The invention includes venous isotopically labeled compounds as defined herein, for example those into which radioactive isotopes, such as $^3H$, $^{13}C$, and $^{14}C$ are present. In one embodiment, the atoms in the formulae herein occur in their natural abundance. In another embodiment, one or more hydrogen atom may be enriched in $^2H$; or/and one or more carbon atom may be enriched in $^{11}C$, $^{13}C$ or $^{14}C$, or/and one or more nitrogen may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to any one of the formulae I to UI. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Isotopically-enriched compounds according to any one of formulae I to III can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by aldosterone synthase and/or CYP11B1, or (ii) associated with aldosterone synthase and/or CYP11B1 activity, or (iii) characterized by abnormal activity of aldosterone synthase and/or CYP11B1; or (2) reduce or inhibit the activity of aldosterone synthase and/or CYP11B1; or (3) reduce or inhibit the expression of aldosterone synthase and/or CYP11B1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of aldosterone synthase and/or CYP11B1; or at least partially reducing or inhibiting the expression of aldosterone synthase and/or CYP11B1.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039.051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspects

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wilts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin- 2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4 Ed, 1952, Methods of Organic Synthesis, Thieme, Volume 21).

The compounds of the invention can be synthesized using the methods described in the following schemes, examples, and by using art recognized techniques. All compounds described herein are included in the invention as compounds. Compounds of the invention may be synthesized according to at least one of the methods described in schemes 1 to 4.

Scheme 1:

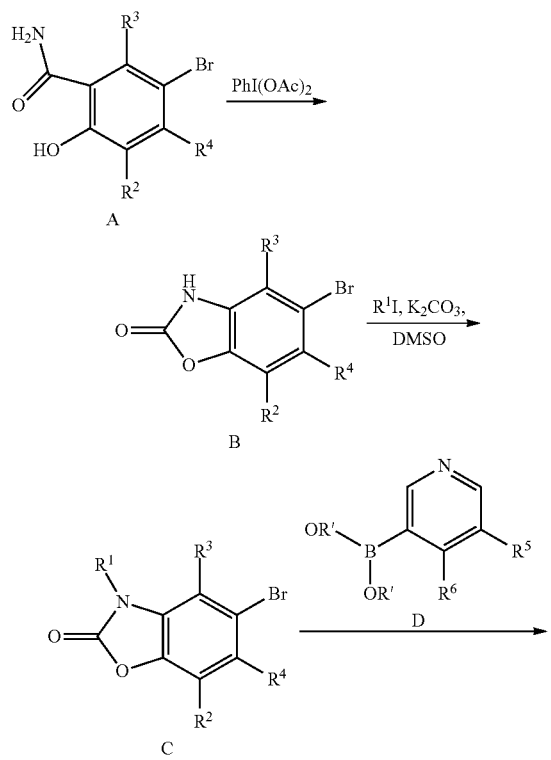

-continued

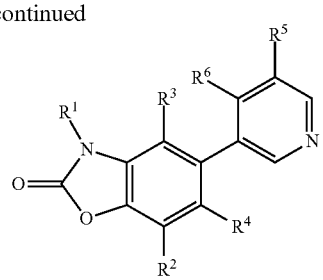

Scheme 1 illustrates the synthesis of compounds of Formula I wherein variables $R^1$ to $R^6$ are as defined in Formula I, supra: substituted 2-hydroxy-benzamide of type A (readily available from its parent carboxylic acid) can be converted to benzoxazolone B via Hofmann rearrangement. Alkylation of B with alkyl halide (such as methyl iodide) in the presence of a suitable base (such as for example potassium carbonate) in a suitable solvent to generate intermediate C. Intermediate C can then undergo Suzuki-type palladium-catalyzed coupling with optionally substituted pyridyl borinic acid or ester (e.g. R' is alkyl or H), such as D, to generate a compound of Formula I. Pyridyl boronic acids or esters are commercially available or are prepared from their corresponding bromide using 4,4,4',4',5,5,5',5'-octamethyl-2,2'-bi(1,3,2-dioxaborolane) and $PdCl_2$(dppf) or any other known methods in the art.

Scheme 2:

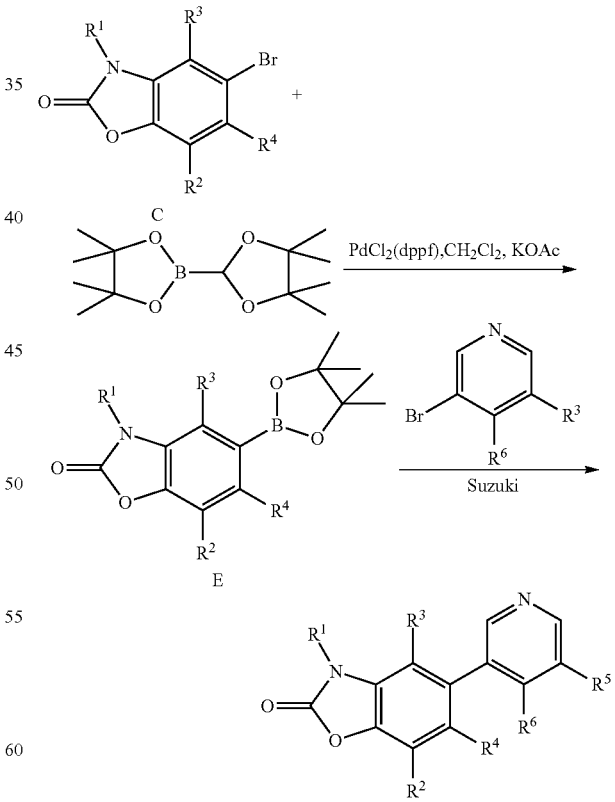

Scheme 2 described an alternative synthesis of compound of Formula I wherein variables $R^1$ to $R^6$ are as defined in Formula I, supra. A compound of type C (benzoxazolone) can be converted into the corresponding boronic ester using 4,4,4', 4',5,5,5',5'-octamethyl-2,2'-bi(1,3,2-dioxaborolane) and PdCl$_2$(dppf) to generate intermediate E. Intermediate E undergoes Suzuki coupling reaction with pyridine F.

Scheme 3:

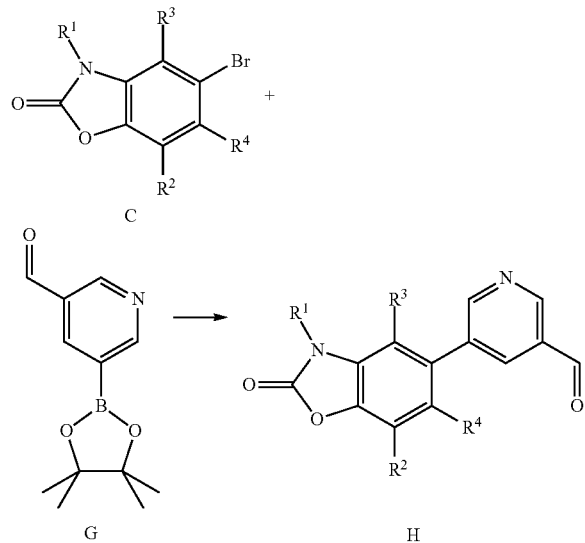

Scheme 3 illustrates the synthesis of an intermediate H, wherein variables $R^1$ to $R^4$ are as defined in Formula I, supra. Intermediate H is obtained after Suzuki coupling of benzoxazolone C with a boronic ester G. Intermediate H can be used for further derivatization. The aldehyde functionality can be converted into primary, secondary alcohol, or into amino, or into sulfonamide as shown in Scheme 4.

defined in Formula I) or $R^5$ is —CH$_2$—NHR$^d$ ($R^d$ is $R^8$ or $R^9$ as defined in Formula I) or $R^5$ is —CH($R^b$)OH in which $R^b$ is alkyl or aryl or arylalkyl) or $R^5$ is —CH($R^b$)NHS(O)$_2$R$^a$ ($R^a$ and $R^b$ are as previously defined) and wherein R is halo (e.g. Bromo) or is benzoxaxolone according to Formula I.

Derivatization on the pyridine can be performed prior to the Suzuki coupling, where R is halo or after the Suzuki coupling where R is benzoxazolone. The compounds of Formula I wherein $R^6$ is other than H can be obtained analogously.

Intermediate (R is halo) or H(R is benzoxazolone) can be reacted with a nucleophile (e.g., $R^b$M is a hydride, Grignard, organolithium, organozinc or other organometallic agent, wherein $R^b$ is alkyl or aryl or arylalkyl) to generate intermediate J (R is halo) or product J (R is benzoxazolone).

Alternatively intermediate I or H can be reacted with aminosulfonyl (e.g. $R^a$SO$_2$NH$_2$ where $R^a$ is alkyl, haloalkyl, cycloalkyl) in the presence of Titanium (IV) alkoxide and a nucleophile (e.g. $R^b$M) to generate intermediate K (R is halo) or product K (R is benzoxazolone).

Intermediate I or H can also be reacted with aminosulfonyl (e.g. $R^a$SO$_2$NH$_2$ where $R^a$ is alkyl, haloalkyl, cycloalkyl, arylalkyl) in the presence of a reductive agent to generate intermediate L (R is halo) or product L (R is benzoxazolone). Also, intermediate I or H can be reacted with an amine ($R^d$NH$_2$ where $R^d$ is $R^d$ is $R^8$ or $R^9$ as defined in Formula I) in the presence of a reducing agent (reductive amination) to generate intermediate M (R is halo) or product M (R is benzoxazolone).

The invention further includes any variant of the present processes, in which an intermediate product obtainable at any stage thereof is used as starting material and the remaining steps are carried out or in which the starting materials are formed in situ under the reaction conditions, or in which the reaction components are used in the form of their salts or optically pure antipodes.

Scheme 4:

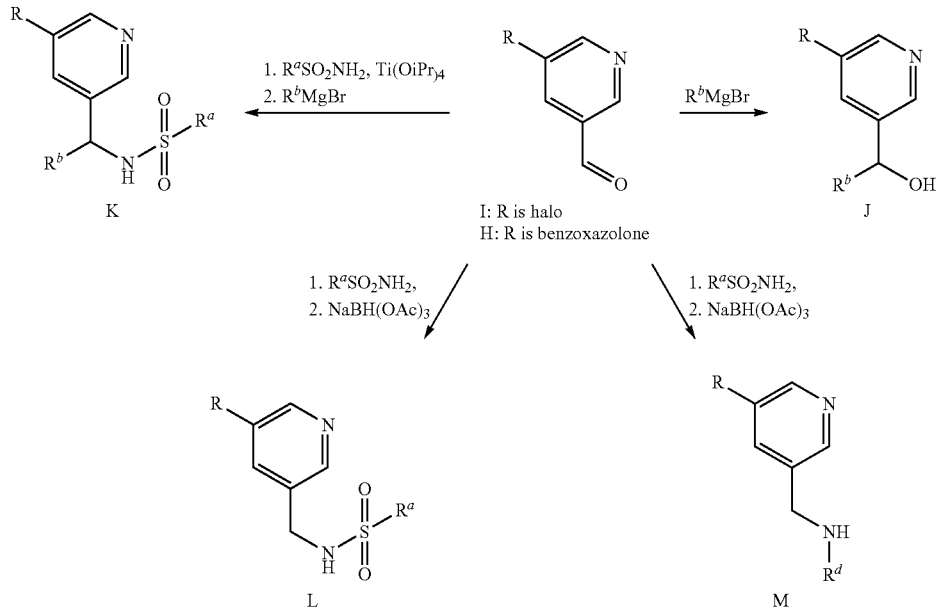

Scheme 4 describes the synthesis of intermediates J, K, L or M or the synthesis of a compound of Formula I wherein $R^5$ is —CH$_2$NHS(O)$_2$R$^a$ ($R^a$ is alkyl, haloalkyl or cycloalkyl as Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. aldosterone synthase and/or CYP11B1 modulating properties, e.g. as indicated in vitro and in vivo tests as provided in the next sections and are therefore indicated for therapy.

Compounds of the invention may be useful in the treatment of an indication selected from hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, or fibrinoid necrosis of coronary arteries, Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke, the cortisol-induced mineralocorticoid excess. Thus, as a further embodiment, the present invention provides the use of a compound according to anyone of formulae or a pharmaceutically acceptable salt thereof, in therapy. In a further embodiment, the therapy is selected from a disease which is ameliorated by inhibition of aldosterone synthase and/or CYP11B1. In another embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

In another embodiment, the invention provides a method of treating a disease which is ameliorated by inhibition of aldosterone synthase and/or CYP11B1 comprising administration of a therapeutically acceptable amount of a compound according to anyone of formulae I-III, or a pharmaceutically acceptable salt thereof. In a further embodiment, the disease is selected from the afore-mentioned list, suitably hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction, more suitably congestive heart failure, cardiac or myocardial fibrosis, renal failure, hypertension or ventricular arrhythmia.

The pharmaceutical composition or combination of the present invention can be in unit dosage of about 0.01-500 mg of active ingredient(s) for a subject of about 50-70 kg, or about 0.01-250 mg or about 0.01-150 mg or about 0.01-100 mg, or about 0.01-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro tests. The compounds of the present invention can be applied in vitro in the form of solutions, e.g. preferably aqueous solutions. The dosage in vitro may range between about $10^{-3}$ molar and $10^{-9}$ molar concentrations. A therapeutically effective amount in vivo may range depending on the route of administration, between about 0.0001-500 mg/kg, or between about 0.0001-100 mg/kg, or between about 0.0003-10 mg/kg.

The activity of a compound according to the present invention can be assessed by the in vitro methods described below.

In particular, the aldosterone synthase inhibitory activities in vitro can be determined by the following assay.

Human adrenocortical carcinoma NCI-H295R cell line was obtained from American Type Culture Collection (Manassas, Va.). Insulin/transferrin/selenium (ITS)-A supplement (100×). DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D-[1,2,6,7-$^3$H(N)]aldosterone was acquired from PerkinElmer (Boston, Mass.). Nu-serum was a product of BD Biosciences (Franklin Lakes, N.J.). The NADPH regenerating system, dibenzylfluorescein (DBF), and human aromatase Supersomes® were obtained from Gentest (Woburn, Mass.).

For in vitro measurement of aldosterone activity, human adrenocortical carcinoma NCI-H295R cells are seeded in NBS 96-well plates at a density of 25,000 cells/well in 100 µl of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 µl of phosphate-buffered saline (PBS) and incubated with 100 µl of treatment medium containing 1 µM Ang II and a compound at different concentrations in quadruplicate wells at 37° C. for 24 hr. At the end of incubation, 50 µl of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 µCi of D-[1,2,6,7-$^3$H(N)]aldosterone and 0.3 µg of anti-aldosterone antibody in PBS containing 0.1% Triton X-100, 0.1% bovine serum albumin, and 12% glycerol in a total volume of 200 µl at room temperature for 1 hr. Anti-mouse PVT SPA beads (50 µl) are then added to each well and incubated overnight at room temperature prior to counting in a Microbeta plate counter. The amount of aldosterone in each sample is calculated by comparing with a standard curve generated using known quantities of the hormone.

The in vitro inhibitory activities for CYP1B1 can be determined by the following assay.

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have Cyp11 B1 (steroid 11 β-hydroxylase). The cells show the physiological property of zonally undifferentiated human foetal adrenocortical cells which, however, have the capacity to produce the steroid hormones which are formed in the three, phenotypically distinguishable zones in the adult adrenal cortex.

The NCI-H295R cells (American Type Culture Collection, ATCC, Rockville, Md., USA) are grown in Dulbeoco's Modified Eagle'Ham F-12 Medium (DME/F12), which has been supplemented with Ulroser SF Serum (Soprachem, Geigy-Saint-Christophe, France), insulin, transferrin, selenite (I-T-S, Becton Dickinson Biosiences, Franklin lakes. NJ, USA) and antibiotics in 75 cm² cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin II (1 D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturer's instructions.

For in vitro measurement of aromatase activity, the human aromatase assay is performed in 96-well flat bottom plates according to a published protocol (Stresser et al, 2000) with minor modifications. Briefly, 10 μL of an NADPH regenerating system containing 2.6 mM $NADP^+$, 6.6 mM glucose 6-phosphate, 6.6 mM $MgCl_2$, and 0.8 U/mL glucose-6-phosphate dehydrogenase in 50 mM potassium phosphate, pH 7.4, is preincubated with the test compound at a desired concentration at 30° C. for 10 min in a total volume of 100 μL. Afterwards, 4 pmol of human aromatase, 20 μg of control microsomal protein, and 4 μM DBF in 100 μL of 50 mM potassium phosphate, pH 7.4, is added to each well and incubated at 30° C. for 90 min. The reaction is terminated by the addition of 75 μL of 2 N NaOH to each well. After 2 h, the product, fluorescin, is measured by a fluorimeter using excitation and emission wavelengths of 485 and 53 nm, respectively.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$, where: a=minimum data level, b=gradient, I c=ICED, d=maximum data level, x=inhibitor concentration.

The inhibition activity of aldosterone production can also be expressed in percentage inhibition (% inhibition) at a given concentration (e.g. % inhibition at 1 μM), which is the aldosterone level when the cell is treated with the given concentration of a compound of this invention (e.g. concentration of 1 μM) versus the aldosterone excretion when cell is free of the compound of the invention:

% inhibition aldosterone production=$[(Y-X)/Y]\times 100$ wherein X is the level of aldosterone when the cell is treated with a compound of Formula I; and Y is the level of aldosterone when the cell is free of compound of Formula I.

The inhibition activity of cortisol production (CYP11B1 activity) can also be expressed in percentage inhibition (% inhibition) at a given concentration (e.g. % inhibition at 1 μM), which is the cortisol level when cell is treated with the given concentration of a compound of the invention (e.g. concentration of 1 μM) versus the cortisol excretion when cell is free of the compound of the invention.

% inhibition cortisol production=$[(Y'-X')/Y']\times 100$ wherein X' is the level of cortisol when the cell is treated with a compound of Formula I; and
Y' is the level of cortisol when the cell is free of compound of Formula I.

Using the test assays (as described above) compounds of the invention exhibit inhibitory efficacy as shown in Table 1, provided infra.

TABLE 1

Inhibitory Activity of Compounds

| Compound | Aldosterone cell secretion (IC50 nM) | Cortisol cell secretion (% Inhib. @ 1 μM) |
|---|---|---|
| Example 1 | 17.8 | 58 |
| Example 2 | 4 | 82 |
| Example 15 | 21 | 83 |
| Example 10 | 17 | 96 |
| Example 8: | | |
| Enantiomer 1 | 53 | 77 |
| Enantiomer 2 | 66 | 73 |
| Example 18 | 34 | 57 |
| Example 14 | 3 | 89 |
| Example 13: | | |
| Enantiomer 1 | 28 | 64 |
| Enantiomer 2 | 30 | 64 |
| Example 19 | 1.4 | 95 |
| Example 7: | | |
| Enantiomer 1 | 437 | |
| Enantiomer 2 | 452 | |
| Example 29: | | |
| Enantiomer 1 | 47 | 57 |
| Enantiomer 2 | 34 | 57 |
| Example 11 | 128 | 39 |
| Example 36 | 144 | 13 |
| Example 4 | 18 | 77 |
| Example 21 | 68 | 65.5 |
| Example 28 | 154 | 30 |

The compound of the present invention may be administered either simultaneously with, or before or after, at least one other therapeutic agent. The compound of the present invention may be administered separately, by the same or different route of administration, or together in the same pharmaceutical composition.

In one embodiment, the invention provides a product comprising a compound according to anyone of formulae I-III, or a pharmaceutically acceptable salt thereof, and at least one other therapeutic agent as a combined preparation for simultaneous, separate or sequential use in therapy. In one embodiment, the therapy is the treatment of a disease or condition mediated by aldosterone synthase and/or CYP11B1. Products provided as a combined preparation include a composition comprising a compound according to any one of formulae I-III, or a pharmaceutically acceptable salt thereof, and the other therapeutic agent(s) together in the same pharmaceutical composition, or the compound according to anyone of formulae I-III, or a pharmaceutically acceptable salt thereof, and the other therapeutic agent(s) in separate form, e.g. in the form of a kit.

In one embodiment, the invention provides a pharmaceutical composition comprising a compound according to any one of formulae I-III, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to any one of formulae I-III, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound according to any one of formulae I-III in the manufacture of a medicament for treating a disease or condition mediated by aldosterone synthase and/or CYP11B1, wherein the medicament is prepared for administration with another therapeutic agent. The invention also provides the use of a another therapeutic agent in the manufacture of medicament for treating a disease or condition mediated by aldosterone synthase, and/or CYP11B1, wherein the medicament is prepared for administration with a compound according to anyone of formulae I-III, or a pharmaceutically acceptable salt thereof.

The invention also provides a compound according to anyone of formulae I-III, or a pharmaceutically acceptable salt thereof, for use in a method of treating a disease or condition mediated by aldosterone synthase and/or CYP11B1, wherein the compound according to anyone of formulae I-III is prepared for administration with another therapeutic agent. The invention also provides another therapeutic agent for use in a method of treating a disease or condition mediated by aldosterone synthase and/or CYP11B1, wherein the other therapeutic agent is prepared for administration with a compound according to anyone of formulae or a pharmaceutically acceptable salt thereof. The invention also provides a compound according to anyone of formulae I-III, or a pharmaceutically acceptable salt thereof, for use in a method of treating a disease or condition mediated by aldosterone synthase and/or CYP11B1, wherein the compound according to anyone of formulae I-III, or a pharmaceutically acceptable salt thereof, is administered with another therapeutic agent. The invention also provides another therapeutic agent for use in a method of treating a disease or condition mediated by aldosterone synthase and/or CYP11B1, wherein the other therapeutic agent is administered with a compound according to any one of formulae or a pharmaceutically acceptable salt thereof.

The invention also provides the use of a compound according to any one of formulae I-III, or a pharmaceutically acceptable salt thereof, in the manufacture of a medicament for treating a disease or condition mediated by aldosterone synthase and/or CYP11B1, wherein the patient has previously (e.g. within 24 hours) been treated with another therapeutic agent. The invention also provides the use of another therapeutic agent in the manufacture of a medicament for treating a disease or condition mediated by aldosterone synthase and/or CYP11B1, wherein the patient has previously (e.g. within 24 hours) been treated with a compound according to anyone of formulae or a pharmaceutically acceptable salt thereof.

In one embodiment, the other therapeutic agent is selected from: HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker, or a CETP inhibitor.

In still another embodiment, the invention pertains, at least in part, to methods wherein the compound of the invention (e.g., a compound according to any one of Formulae I-III or a compound otherwise described herein) is administered in combination with a second agent.

The term "in combination with" a second agent or treatment includes co-administration of the compound of the invention (e.g., a compound according to any one of Formulae I-III or a compound otherwise described herein, or a pharmaceutically acceptable salt thereof) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g., an aldosterone synthase associated disorder, such as, for example, hypokalemia, hypertension, Conn's disease, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction, cardiovascular diseases, renal dysfunction, liver diseases, cerebrovascular diseases, vascular diseases, retinopathy, neuropathy, insulinopathy, edema, endothelial dysfunction, baroreceptor dysfunction, migraine headaches, heart failure such as congestive heart failure, arrhythmia, diastolic dysfunction, left ventricular diastolic dysfunction, diastolic heart failure, impaired diastolic filling, systolic dysfunction, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, and fibrinoid necrosis of coronary arteries. Furthermore, the second agent may be any agent of benefit to the patient when administered in combination with the administration of a compound of the invention.

Examples of second agents include HMG-Co-A reductase inhibitors, angiotensin II receptor antagonists, angiotensin converting enzyme (ACE) inhibitors, calcium channel blockers (CCB), dual angiotensin converting enzyme/neutral endopeptidase (ACE/NEP) inhibitors, endothelin antagonists, renin inhibitors, diuretics, ApoA-I mimics, anti-diabetic agents, obesity-reducing agents, aldosterone receptor blockers, endothelin receptor blockers, and CETP inhibitors.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

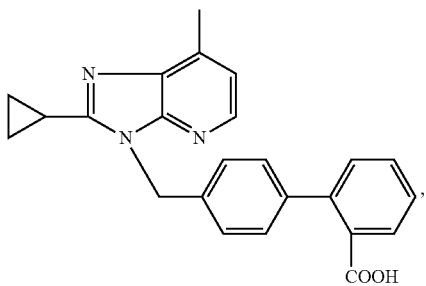 [SMILES: Cc1ccnc2c1nc(C1CC1)n2Cc1ccc(-c2ccccc2C(=O)O)cc1]

the compound with the designation SC-52458 of the following formula

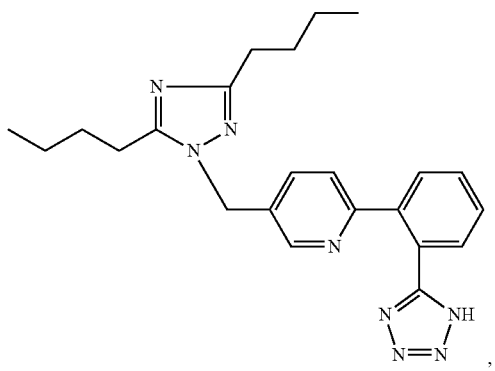 [SMILES: CCCCc1nc(CCCC)n(Cc2ccc(-c3ccccc3-c3nnn[nH]3)nc2)n1]

and the compound with the designation ZD-8731 of the following formula

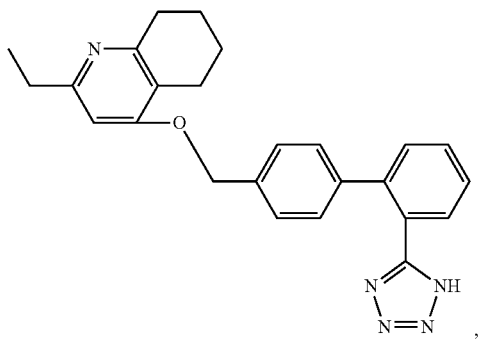 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "dual angiotensin converting enzyme/neutral endopeptidase (ACE/NEP) inhibitor" includes omapatrilate (cf. EP 629627), fasidotril or fasidotrilate, or pharmaceutically acceptable salts thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy) phenyl]methyl}-8-methyl-2-(propan-2-yl)nonanamide) and zankiren (chemical name: [1S-[[1R*[(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP300 as developed by Speedel, or RO 66-1132 and RO 66-1168 of Formula (A) and (B):

(A)

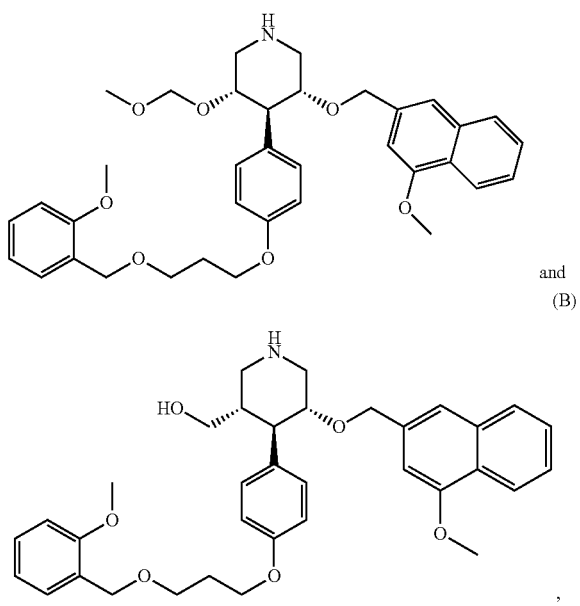

and
(B)

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic □-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

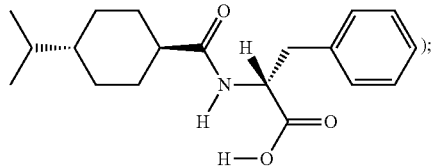 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1. WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia,* 28, 1985, 704-707 and in U.S. Pat. No. 5,705,483.

The term GLP-1 agonists' includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP 1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]- methyl}thiazolidine-2,4-dione (T-174) and 5-(2,4-dioxothia-zolidin-5-ylmethyl)-2-methoxy-N-(4-trifluoromethyl-benzyl)benzamide (KRP297)).

Further anti-diabetic agents include, insulin signaling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPAR☐ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α₂-adrenergic antagonists; and pharmaceutically acceptable salts thereof.

The term "obesity-reducing agent" includes lipase inhibitors (e.g., orlistat) and appetite suppressants (e.g., sibutramine and phentermine).

The term "aldosterone receptor blocker" includes spironolactone and eplerenone.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

Exemplification of the Invention

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Abbreviations:

| | |
|---|---|
| ATP: adenosine 5'-triphosphate | AS: Aldosterone Synthase |
| BINAP: racemic 2,2'-bis (diphenylphosphino)-1,1'-binaphthyl | BOC: tertiary butyl carboxy |
| br: broad | bs: broad singlet |
| calcd: calculated | CYP11B1: 11-beta hydroxylase |
| d: doublet | DAST: (diethylamino)sulfur trifluoride |
| dd: doublet of doublets | DCM: dichloromethane |
| DIEA: diethylisopropylamine | DME: 1,4-dimethoxyethane |
| DMF: N,N-dimethylformamide | DMSO: dimethylsulfoxide |
| DPPA: diphenylphosphorylazide | DTT: dithiothreitol |
| EDTA: ethylenediamine tetraacetic acid | ESI: electrospray ionization |
| EtOAc: ethyl acetate | h: hour(s) |
| HATU: O-(7-azobenzotriazol-1-yl)-1,1,3,3-tetramethyluroniumhexafluorophosphate | HOBt: 1-hydroxy-7-azabenzotriazole |
| HPLC: high pressure liquid chromatography | LCMS: liquid chromatography and mass spectrometry |
| MeOD: methanol-d4 | MeOH: methanol |
| MS: mass spectrometry | m: multiplet |
| min: minutes | m/z: mass to charge ratio |
| n.d.: not determined | NMR: nuclear magnetic resonance |
| ppm: parts per million | Pr: propyl |
| PyBOP: benzotriazol-1-yloxy Tripyrrolidinophosphoniumhexafluorophosphate | rt: room temperature |
| s: singlet | t: triplet |
| TFA: trifluoroacetic acid | THF: tetrahydrofuran |
| TLC: thin layer chromatography | Tris•HCl: aminotris (hydroxymethyl) methane hydrochloride |

EXAMPLES

Example 1

3-Methyl-5-pyridin-3-yl-3H-benzooxazol-2-one

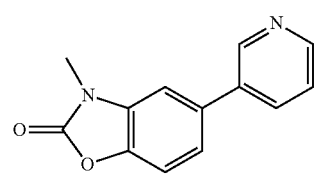 [SMILES: Cn1c(=O)oc2ccc(-c3cccnc3)cc21]

Step 1: Synthesis of
5-Bromo-3-methyl-3H-benzooxazol-2-one

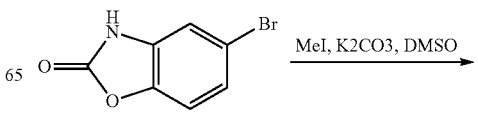

-continued

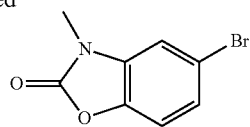

A mixture of 5-Bromo-3-hydro-3H-benzooxazol-2-one (500 mg, 2.3 mmol), iodomethane (291 uL, 663 mg, 4.67 mmol), K2CO3 (807 mg, 5.84 mmol) in DMSO (10 mL) was stirred at room temperature for overnight. After concentration under reduced pressure, the residue was purified by flash column and yielded colorless solid (440 mg). $^1$HNMR (CDCl$_3$, 400.342 MHz): δ 3.38 (5, 3H), 7.07 (d, J=8 Hz, 1H), 7.10 (d, J=1.9 Hz, 1H), 7.24 (dd, J=8, 1.9 Hz, 1H).

Step 2: Synthesis of
3-Methyl-5-pyridin-3-yl-3H-benzooxazol-2-one

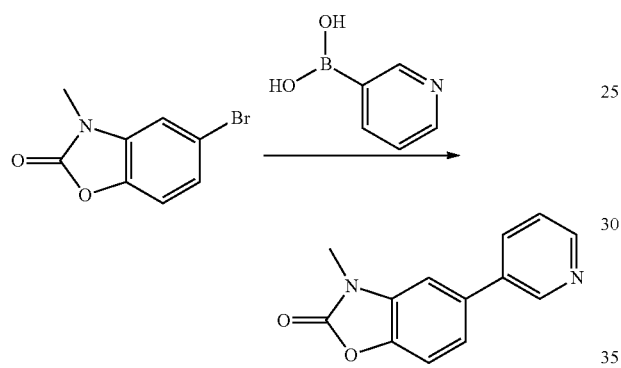

A mixture of pyridin-3-ylboronic acid (61.5 mg, 0.5 mmol), 5-Bromo-3-methyl-3H-benzooxazol-2-one (114 mg, 0.5 mmol), polymer-supported Pd(PPh$_3$)$_4$ (0.11 mmol/g, 114 mg, 0.0125 mmol), Na$_2$CO$_3$ (2 M in water, 0.5 mL, 1 mmol) in DME (3 mL) was heated to reflux for 6 hrs. After filtration and concentration, the residue was purified by flash column (MeOH—CH2Cl2, v/v, 1-3%) and yielded the title compound as pale yellow solid (45 mg). $^1$HNMR(CDCl3, 400.342 MHz): δ 3.47 (s, 3H), 7.13 (s, 1H), 7.30 (m, 2H), 7.38 (dd, J=4.8, 7.9 Hz, 1H), 7.85 (m, 1H), 8.62 (dd, J=1.5, 4.8 Hz, 1H), 8.82 (d, J=2.4 Hz, 1H).

Example 2

3-Methyl-5-(4-methyl-pyridin-3-yl)-3H-benzooxazol-2-one

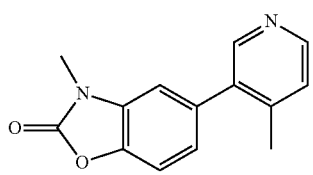

The entitled compound was synthesized using the Suzuki coupling conditions described in example 1. $^1$HNMR (CDCl$_3$, 400.342 MHz): δ 2.22 (s, 3H), 3.37 (s, 3H), 6.83 (d, J=1.6 Hz, 1H), 6.98 (dd, J=8.2, 1.68 Hz, 1H), 7.14 (d, J=6 Hz, 1H), 7.20 (d J=8.2 Hz, 1H), 8.36 (s, 1H), 8.40 (d, J=6.04 Hz, 1H).

Example 3

5-(5-fluo pyridin-3-yl)-3-methylbenzo[d]oxazol-2 (3H-one

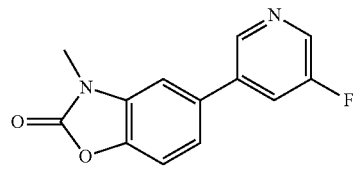 [SMILES: Cn1c(=O)oc2ccc(-c3cncc(F)c3)cc21]

The entitled compound was synthesized using the Suzuki coupling conditions described in example 1, $^1$HNMR (CDCl$_3$, 400.342 MHz): δ 3.41 (s, 3H), 7.06 (s, 1H), 7.24 (m, 2H), 7.51 (m, 1H), 841 (d, J=2.6 Hz, 1H), 8.58 (s, 1H).

Example 4

5-(5-methoxypyridin-3-yl)-3-methylbenzo[d]oxazol-2(3H)-one

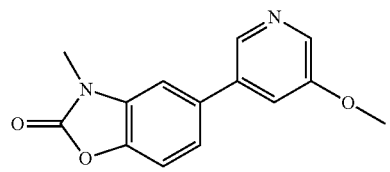 [SMILES: COc1cncc(-c2ccc3oc(=O)n(C)c3c2)c1]

The entitled compound was synthesized using the Suzuki coupling conditions described in example 1. $^1$HNMR (CDCl$_3$, 400.342 MHz): δ 3.45 (s, 3H), 3.92 (s, 3H), 7.11 (d, J=1.2 Hz, 1H), 7.28 (s, 1H), 2.29 (d, J=1.5 Hz, 1H), 7.31 (t, J=2.6 Hz, 1H), 8.30 (d, J=216 Hz, 1H), 8.41 (d, J=1.84 Hz, 1H).

Example 5

5-(3-methyl-2-oxo-2,3-dihydrobenzo[d]oxazol-5-yl) nicotinonitrile

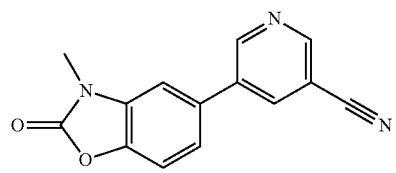 [SMILES: Cn1c(=O)oc2ccc(-c3cncc(C#N)c3)cc21]

The entitled compound was synthesized using the Suzuki coupling conditions described in example 1. $^1$HNMR (CDCl$_3$, 400.342 MHz): δ 3.48 (s, 3H), 7.12 (d, J=1.68 Hz, 1H), 7.32 (d, J=1.76 Hz, 1H), 7.34 (s, 1H), 8.11 (t, J=2.16 Hz, 1H), 8.88 (d, J=1.92 Hz, 1H), 9.01 (d, J=2.3 Hz, 1H).

Example 6

5-(4-(hydroxymethyl)pyridin-3-yl)-3-methylbenzo[d]oxazol-2(3H)-one and 1,1,1-trifluoro-N-((3-(3-methyl-2-oxo-2,3-dihydrobenzo[d]oxazol-5-yl)pyridin-4-yl)methyl)methanesulfonamide

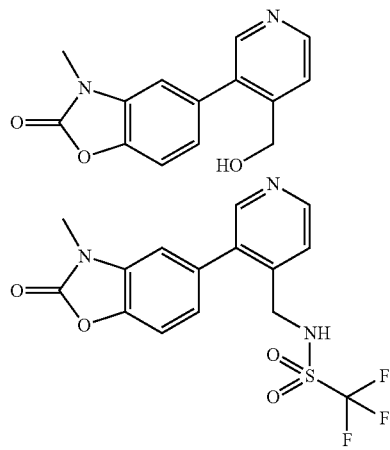

Step 1: synthesis 3-(3-Methyl-2-oxo-2,3-dihydrobenzooxazol-5-yl)-pyridine-4-carbaldehyde

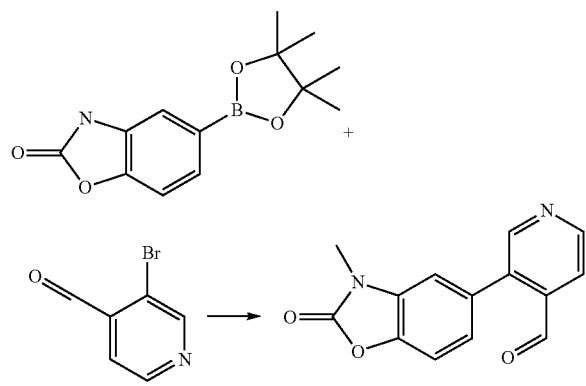

A mixture of 3-Methyl-5-(4,4,5,5-tetramethyl-[1,3,2]dioxaborolan-2-0)-3H-benzooxazol-2-one (330 mg, 1.2 mmol), 3-Bromo-pyridine-4-carbaldehyde (186 mg, 1 mmol), polymer bound Pd(PPh$_3$)$_4$ (642 mg, 0.07 mmol), Na$_2$CO$_3$ (2 M in water, 1 mL, 2 mmol) in N,N-Dimethylacetamide (9 mL) and water (1 mL) was heated to 100° C. by microwave for 1 h. The reaction mixture was cooled to room temperature. The suspension was diluted with CH$_2$Cl$_2$ (15 mL) and filtered through a pad of celite. The filtrate was concentrated in vacuo to reddish brown solid. This crude material was purified by flash column (0-10% CH$_3$OH in CH$_2$Cl$_2$, v/v) and afforded 152 mg of the desired product. ESI-MS m/z: 255.0 [M+1]$^+$, Retention time 1.03 min; $^1$HNMR (DMSO, 400.342 MHz): δ 3.39 (s, 3H), 7.27 (dd, J=8.2, 1.8 Hz, 1H), 7.50 (d, J=8.2 Hz, 1H), 7.57 (d, J=1.8 Hz, 1H), 8.85 (m, 2H), 10.0 (s, 1H).

Step 2: synthesis of 5-(4-(hydroxymethyl)pyridin-3-1)-3-methylbenzo[d]oxazol-2(3H)-one and 1,1,1-trifluoro-N-((3-(3-methyl-2-oxo-2,3-dihydrobenzo[d]oxazol-5-yl)pyridin-4-yl)methyl)methanesulfonamide

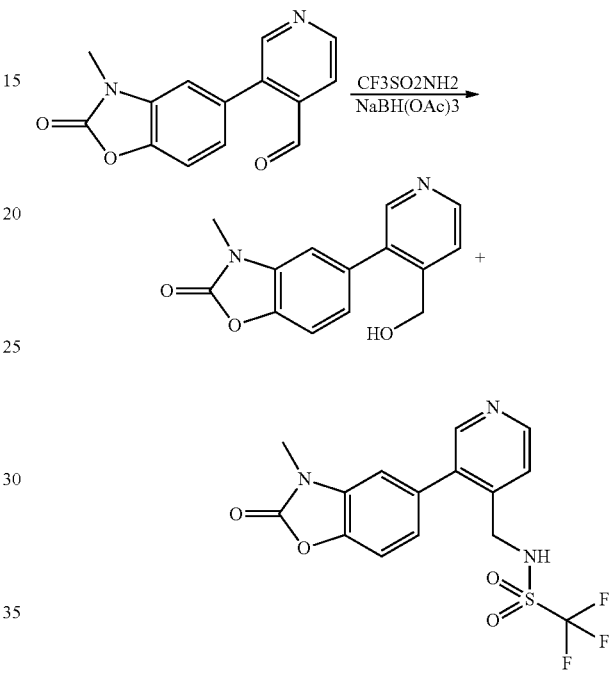

A mixture of 3-(3-methyl-2-oxo-2,3-dihydrobenzo[d]oxazol-5-yl)isonicotinaldehyde (128 mg, 0.5 mmol), trifluoromethanesulfonamide (94 mg, 0.63 mmol), acetic acid (60.5 mg, 1 mmol) and 4° A molecular sieves in 1,2-dichloroentane (2 mL) heated at 70° C. under nitrogen for 6 h. The suspension was cooled to room temperature and sodium triacetoxyborohydride (excess amount) was added. The reaction mixture was further stirred at room temperature for an additional 15 h. The mixture was diluted with dichloromethane (20 mL) and filtered through a pad of celite. The filter cake was thoroughly washed with an additional 30 mL of dichloromethane. The combined filtrates were washed with NaHCO$_3$ (saturated solution). The aqueous phase was extracted with dichloromethane (2×50 mL). The organic phases were combined, dried over anhydrous Na2SO4. After filtration and concentration, the residue was purified by flash column (0-100% ethyl acetate in heptane, v/v) and yielded 43 mg of 1,1,1-trifluoro-N-((3-(3-methyl-2-oxo-2,3-dihydrobenzo[d]oxazol-5-yl)pyridin-4-yl)methyl)methane-sulfonamide as colorless solid ESI-MS m/z; 388.0 [M+1]$^+$, Retention time 1.19 min; $^1$HNMR (MeOD, 400.342 MHz): δ 3.43 (s, 3H), 4.41 (5, 2H), 7.12 (dd, J=8.2, 1.8 Hz, 1H), 7.15 (s, 1H), 7.21 (d, J=1.6 Hz, 1H), 760 (d, J=5.2 Hz, 1H), 8.46 (s, 1H), 8.60 (d, J=8.2 Hz, 1H); and 5-(4-(hydroxymethyl)pyridin-3-yl)-3-methylbenzo[d]oxazol-2(3H)-one 37 mg as pinkish solid ESI-MS m/z: 257.0 [M+1]$^+$, Retention time 0.84 min; $^1$HNMR (MeOD, 400.342 MHz): δ 3.3 (s, 3H), 4.41 (s, 2H), 7.12 (dd, J=1.76, 8.2 Hz, 1H), 7.21 (d, J=1.56 Hz, 1H), 7.37 (d, J=8.2 Hz, 1H), 7.60 (d, J=5.2 Hz, 1H), 8.46 (s, 1H), 8.60 (d. J=5.2 Hz, 1H).

Example 7

5-(4-(1-hydroxyethyl)pyridin-3-yl)-3-methylbenzo[d]oxazol-2(3H)-one

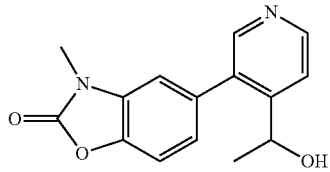 [SMILES: CC(O)c1ccncc1-c1ccc2oc(=O)n(C)c2c1]

Step 1: Synthesis of 1-(3-Bromo-pyridin-4-yl)-ethanol

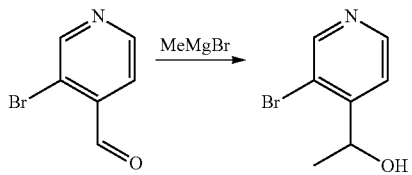

A solution of methylmagnesium bromide (10.00 ml, 30.0 mmol) was added dropwise to a solution of 3-Bromo-pyridine-4-carbaldehyde (1.860 g, 10.00 mmol) in THF (30 mL) at −78° C. The resulting mixture was slowly warmed up to 0° C. over 3 h of period. The reaction was quenched by saturated NH$_4$Cl solution. After extraction with ethyl acetate (50 mL×4), the combined extracts were dried over Na$_2$SO$_4$. After filtration and concentration, an oil residue was obtained, which turned into solid after standing (2.1 g). $^1$H NMR (400.3 MHz, CDCl$_3$): δ 0.23 (d, J=8 Hz, 3H), 3.91 (m, 1H), 6.29 (d, J=4 Hz, 1H), 7.26 (d, J=4 Hz, 1H), 7.37 (s, 1H).

Step 2: Synthesis of 3-Methyl-5-(4,4,5,5-tetramethyl-[1,3,2]dioxaborolan-2-yl)-3H-benzooxazol-2-one

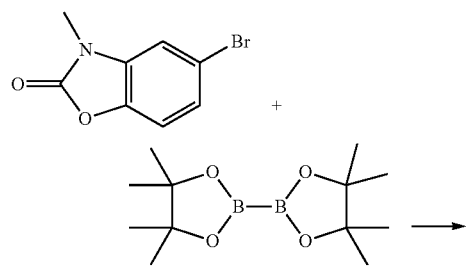

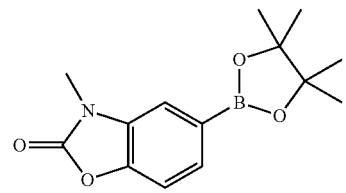

A suspension of 5-Bromo-3-methyl-3H-benzooxazol-2-one (6.25 g, 27.4 mmol), 4,4,4',4',5,5,5',5'-octamethyl-2,2'-bi(1,3,2-dioxaborolane) (7.66 g, 30.1 mmol), potassium acetate (5.38 g, 54.8 mmol) and PdCl$_2$(dppf).CH$_2$Cl$_2$ (1.12 g, 1.37 mmol) in anhydrous 1,4-dioxane (80 mL) was heated at 80° C. under nitrogen for 5 hr. After concentration, the residue was treated with CH$_2$Cl$_2$ (80 mL) and filtrated. The solvent was removed in vaccuo. The residue was purified by flash column (ethyl acetate in heptane, v/v, 0-100%) and yielded colorless solid (5.2 g). $^1$H NMR (400.3 MHz, CDCl$_3$): δ 1.37 (s, 12H), 3.43 (s, 3H), 7.21 (d, J=8 Hz, 1H), 7.40 (s, 1H), 7.63 (dd, J=8, 1 Hz, 1H).

Step 3: Synthesis of 5-(4-(1-hydroxyethyl)pyridin-3-yl)-3-methylbenzo[d]oxazol-2(3H)-one

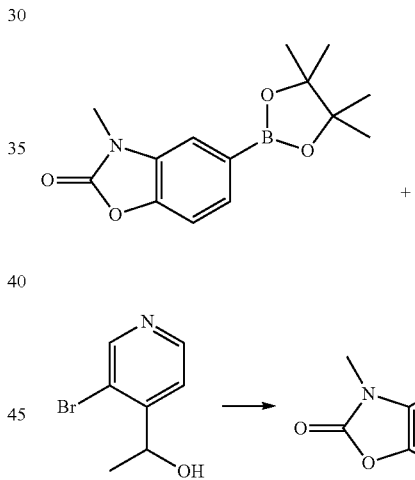

A mixture of 1-(3-Bromo-pyridin-4-yl)-ethanol (240 mg, 1.188 mmol), 3-Methyl-5-(4,4,5,5-tetramethyl-[1,3,2]dioxaborolan-2-yl)-3H-benzooxazol-2-one (327 mg, 1.188 mmol), PalladiumTetrakis (270 mg, 0.030 mmol), sodium carbonate (2 M in water, 0.594 ml, 1.188 mmol) in 1,4-Dioxane (2 ml) was heated by microwave at 100° C. for 1 hr. After filtration, drying over Na$_2$SO$_4$, filtration again and concentration, the residue was purified by flash column (CH$_2$Cl$_2$-MeOH, v/v, 1%-4.5%) yielded an oil which was subsequently purified by chiral HPLC (Ethanol-Heptane, v/v, 20%, ChiralPak OD-H column) to peak 1 (enantiomer 1 retention time 9.21 min) and second peak (enantiomer 2, retention time 11.31 min). ESI-MS m/z: 271.2 [M+1]$^+$, Retention time 0.93 min; $^1$H NMR (400.3 MHz, MeOD): δ 1.32 (d, J=6.4 Hz, 3H), 3.47 (s, 3H), 497 (q, J=6.4 Hz, 1H), 7.15 (dd, J=8.0, 2.0 Hz, 1H), 7.22 (d, J=2.0 Hz, 1H), 7.40 (d, J=8.0 Hz, 1H), 7.75 (d, J=5.6 Hz, 1H), 8.38 (s, 1H), 8.59 (d, J=5.6 Hz, 1H).

Example 8

5-(4-((4-fluorophenyl)(hydroxy)methyl)pyridin-3-yl)-3-methylbenzo[d]oxazol-2(3H)-one

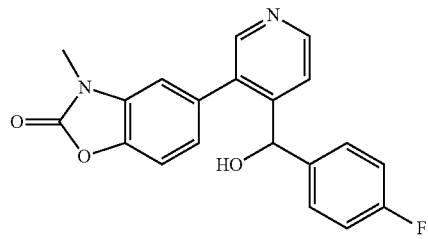 [SMILES: Cn1c(=O)oc2ccc(-c3cnccc3C(O)c3ccc(F)cc3)cc21]

Step 1: Synthesis of (3-Bromo-pyridin-4-yl)-(4-fluoro-phenyl)-methanol

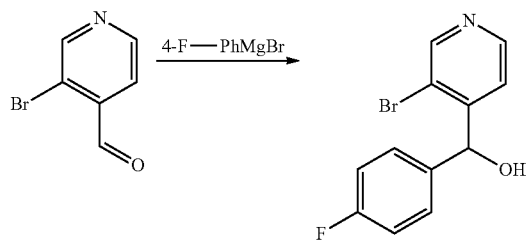

A solution of 4-Fluoromagnesium bromide (2 M in ether, 6.3 mL, 12.6 mmol) was added dropwise to a solution of 3-Bromo-pyridine-4-carbaldehyde (931 mg, 5 mmol) in THF (15 mL) at −45° C. The resulting mixture was stirred at this temperature for additional 2 h. The reaction was quenched by saturated NH$_4$Cl solution. After extraction with ethyl acetate (75 mL×3), the combined extracts were dried over Na$_2$SO$_4$. After filtration and concentration, a yellow solid was obtained. (893 mg). ESI-MS m/z: 284.0 [M+1]$^+$, Retention time 1.17 min;

Step 2: The synthesis of 5-(4-((4-fluorophenyl)(hydroxy)methyl)pyridin-3-yl)-3-methylbenzo[d]oxazol-2(3H)-one

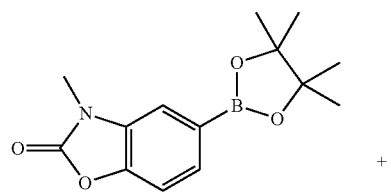

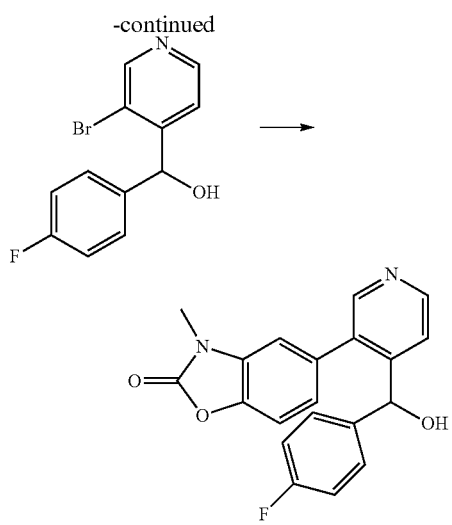

Similar procedure in example 7 was used here. ESI-MS m/z: 251.0 [M+1]$^+$, Retention time 1.17 min; $^1$HNMR (MeOD, 400.342 MHz) δ 3.35 (s, 3H), 5.48 (d, J=1.68 HZ, 1H), 5.83 (brs, 1H), 6.86 (s, 1H), 6.90-7.01 (m, 5H), 7.27 (d, J=8.1 Hz, 1H), 7.81 (d, J=5.2 Hz, 1H), 8.33 (s, 1H), 8.59 (d, J=5.2 Hz, 1H). The enantiomers were separated by chiral HPLC (Ethanol-Heptane, v/v, 20%, ChiralPak OD-H column) peak 1 (enantiomer one retention time 8.91 min) and second peak (enantiomer 2, retention time 11.77 min).

Example 9

5-[5-(1-Hydroxy-ethyl)-pyridin-3-yl]-3-methyl-3H-benzooxazol-2-one

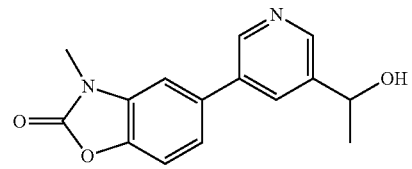

Step 1: Synthesis of 1-(5-Bromo-pyridin-3-yl)-ethanol

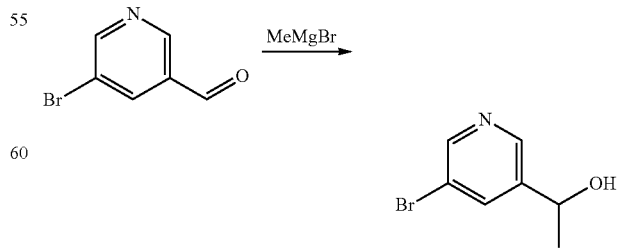

The above compound was synthesized using the procedures described in step 1 example 7. $^1$HNMR (CDCl3, 400.342 MHz) δ 1.45 (d, J=6.48 Hz, 3H), 4.88 (q, J=6.48 Hz, 1H), 7.88 (t, J=2 Hz, 1H), 8.41 (d, J=2 Hz, 1H), 8.47 (d, J=2 Hz, 1H).

Step 2: Synthesis of 5-[5-(1-Hydroxy-ethyl)-pyridin-3-yl]-3-methyl-3H-benzooxazol-2-one

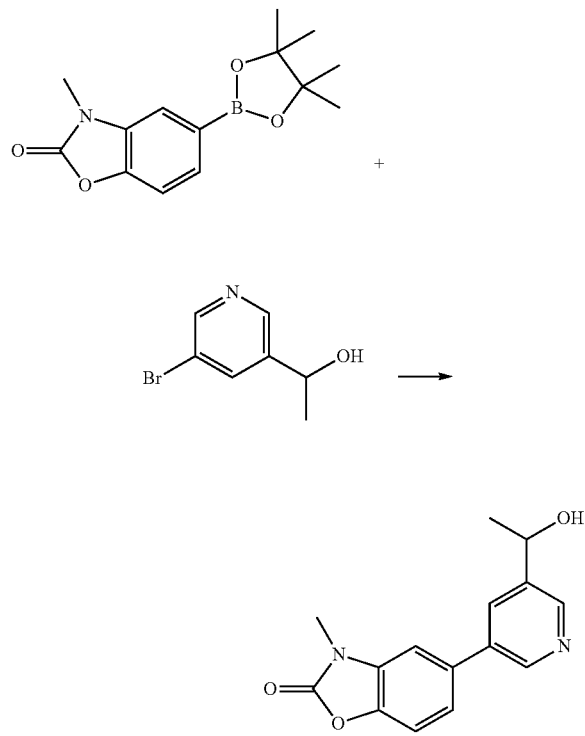

The above compound was synthesized using the Suzuki coupling conditions described in example 7. ESI-MS m/z: 271.2 [M+1]$^+$, Retention time 0.94 min; $^1$HNMR (DMSO-d6, 400.342 MHz) δ 1.43 (d, J=6.5 Hz, 3H), 3.42 (s, 3H), 4.87 (q J=45 Hz, 1H), 5.39 (d, J=4.4 Hz, 1H), 7.43-7.50 (m, 2H), 7.67 (d, J=1.6 Hz, 1H), 8.03 (t, J=2 Hz, 1H), 8.55 (d, J=2 Hz, 1H), 8.79 (d, J=2 Hz, 1H). The enantiomers were separated by chiral HPLC (10% ethanol in supercritical carbon dioxide, v/v, ChiralPak AD-H column): peak 1 (enantiomer one retention time 11.61 min) and second peak (enantiomer 2, retention time 13.26 min).

Example 10

5-{5-[(Benzyl-ethyl-amino)-methyl]-pyridin-3-yl}-3-methyl-3H-benzooxazol-2-one

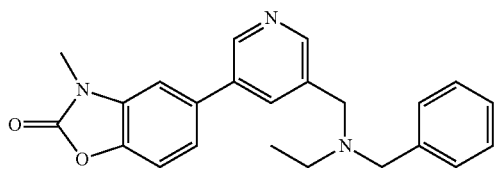 [SMILES: CCN(Cc1ccccc1)Cc1cncc(-c2ccc3oc(=O)n(C)c3c2)c1]

Step 1: Synthesis of 5-(3-Methyl-2-oxo-2,3-dihydro-benzooxazol-5-yl)-pyridine-3-carbaldehyde

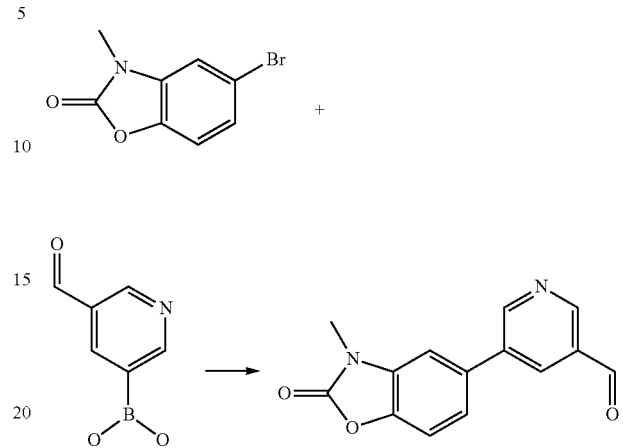

A mixture of 5-Bromo-3-methyl-3H-benzooxazol-2-one (684 mg, 3 mmol), 5-(4,4,5,5-Tetramethyl-[1,3,2]dioxaborolan-2-yl)-pyridine-3-carbaldehyde (699.2 mg, 3 mmol), polymer supported PalladiumTetrakis (0.11 mmol/g, 682 mg, 0.075 mmol), Na2CO3 (2 M in eater, 3 mL, 6 mmol) in DME (6 mL) was heated to reflux for overnight. After filteration and concentration, the residue was purified by flash column and yielded yellow solid. ESI-MS m/z: 255.0 [M+1]$^+$, Retention time 1.03 min.

Step 2: Synthesis of 5-[5-(Benzylamino-methyl)-pyridin-3-yl]-3-methyl-3H-benzooxazol-2-one

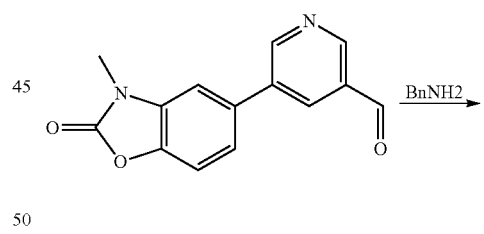

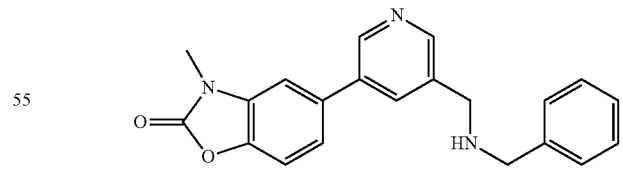

A mixture of 5-(3-Methyl-2-oxo-2,3-dihydro-benzooxazol-5-yl)-pyridine-3-carbaldehyde (100 mg, 0.39 mmol), Benzylamine (46.4 mg, 0.43 mmol), acetic acid (50 uL) and sodium triacetoxyborohydride (25 0 mg, 1.18 mmol) in CH$_2$Cl$_2$ (10 mL) was stirred at room temperature for 2 h. The mixture was quenched with NaHCO3 (saturated solution) and extracted with CH$_2$Cl$_2$ (20 mL×3). The combined extracts were washed with brine and dried over anhydrous Na2SO4. After filtration and concentration, the residue was obtained as yellow solid. ESI-MS m/z: 346.1 [M+1]⁺, Retention time 1.11 min.

Step 3: Synthesis of 5-{5-[(Benzyl-ethyl-amino)-methyl]-pyridin-3-yl}-3-methyl-3H-benzooxazol-2-one

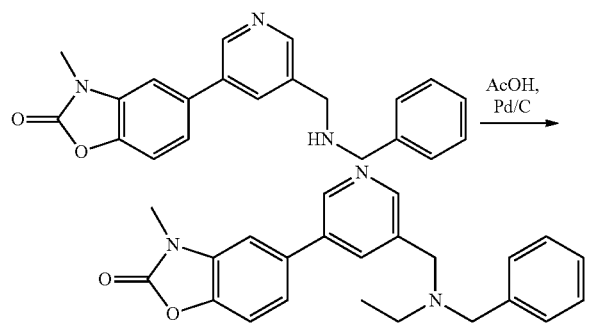

A mixture of 5-(5-(Benzylamino-methyl)-pyridin-3-yl)-3-methyl-3H-benzooxazol-2-one (crude from step 2, ~0.39 mmol) and Pd(OH)$_2$ (20 mg, 10%) in ethanol (10 mL) and acetic acid (0.5 mL) was stirred under 1 atmosphere of H2 at room temperature for 48 h. After filtration and concentration, the residue was purified by flash column (MeOH—CH$_2$Cl$_2$, v/v, 0-5%) and yielded yellow solid (3 mg), ESI-MS m/z: 387.9 [M+1]⁺, Retention time 1.45 min; ¹HNMR (CDCl3, 400.342 MHz) δ 1.48 (t, J=7.2 Hz, 3H), 3.05 (s, 2H), 3.48 (s, 3H), 4.23 (s, 2H), 4.05-4.27 (m, 2H), 7.21 (s, 1H), 7.23 (5, 1H), 7.40-7.43 (m, 3H), 7.62-7.64 (m, 2H), 7.83 (s, 1H), 8.52 (5, 1H), 8.85 (d. J=1.84 Hz, 1H), 9.21 (s, 1H).

Example 11

6-Fluoro-5-(5-hydroxymethyl-pyridin-3-yl)-3-ethyl-3H-benzooxazol-2-one

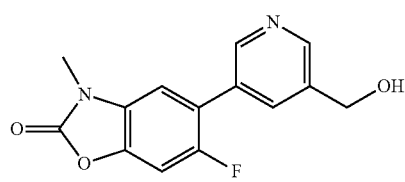 [SMILES: Cn1c(=O)oc2cc(F)c(-c3cncc(CO)c3)cc21]

Step 1: Synthesis of 6-Fluoro-3-methyl-5-(4,4,5,5-tetramethyl-[1,3,2]dioxaborolan-2-yl)-3H-benzooxazol-2-one

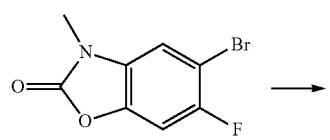

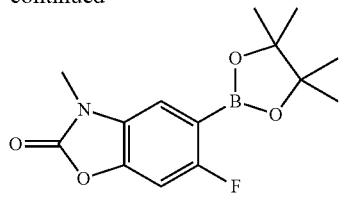

The above compound was synthesized using the Suzuki coupling conditions described in step 2 in example 7. ESI-MS m/z: 294.0 [M+1]⁺, Retention time 1.38 min; ¹HNMR (CDCl3, 400.342 MHz) δ 1.37 (s, 12H), 3.40 (s, 3H), 6.95 (d, J=8.2 Hz, 1H), 7.25 (s, 1H).

Step 2: Synthesis of 6-Fluoro-5-(5-hydroxymethyl-pyridin-3-yl)-3-methyl-3H-benzooxazol-2-one

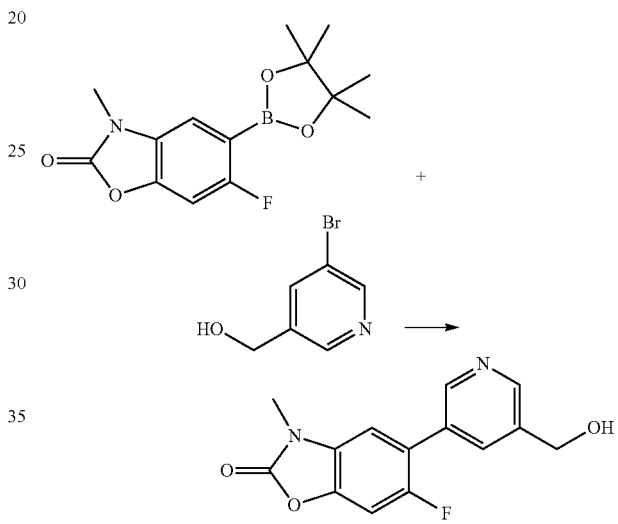

A mixture of 6-Fluoro-3-methyl-5-(4,4,5,5-tetramethyl-[1,3,2]dioxaborolan-2-yl)-3H-benzooxazol-2-one (352 mg, 1.2 mmol), (5-bromopyridin-3-yl)methanol (188 mg, 1 mmol), Na2CO3 (2 M in water, 1 mL, 2 mmol), polymer bound Pd(PPh3)4 (642 mg, 0.07 mmol) in DME (4 mL) was heated by microwave at 100° C. for 1.25 h. The reaction mixture was cooled to room temperature and the mixture was diluted with CH3OH/CH2Cl2 (1:1, 50 mL) and filtered through a pad of celite. The celite pad was further washed with CH2Cl2/CH3OH (50 mL). Ater concentration, the residue was purified by flash column (0-10%, v/v, CH3OH in CH$_2$Cl$_2$) and afforded 121.9 mg of the desired product as a white solid. ESI-MS m/z: 274.9 [M+1]⁺, Retention time 0.93 min; ¹HNMR (MeOD, 400.342 MHz) δ 3.44 (s, 3H), 4.74 (s, 2H), 7.30 (d, J=9.7 Hz, 1H), 7.34 (d, J=6.4 Hz, 1H), 8.03 (s, 1H), 8.55 (s, 1H), 8.64 (s, 1H)

Example 12

6-Fluoro-5-[5-(1-hydroxy-ethyl)-pyridin-3-yl]-3-methyl-3H-benzooxazol-2-one

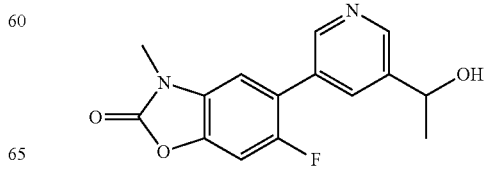

The entitled compound was synthesized using the Suzuki coupling conditions described in example 11, ESI-MS m/z: 289.3 [M+1]+, Retention time 0.68 min; ¹HNMR (d6-DMSO, 400.342 MHz) δ 2.50 (d, J=3.36 Hz, 3H), 3.35 (s, 3H), 4.62 (m, 1H), 7.32 (d, J=6.37 Hz, 1H), 7.57 (d, J=9 Hz, 1H), 7.64 (d, J=5 Hz, 1H), 8.33 (s, 1H), 8.62 (d, J=5 Hz, 1H). The enantiomers were separated by chiral HPLC (Ethanol-Heptane, v/v, 20%, ChiralPak OD-H column) peak 1 (enantiomer 1 retention time 10.39 min) and second peak (enantiomer 2, retention time 14.63 min).

Example 13

5-(5-(cyclopropyl(hydroxy)methyl)pyridin-3-yl)-3-methylbenzo[d]oxazol-2(3H)-one

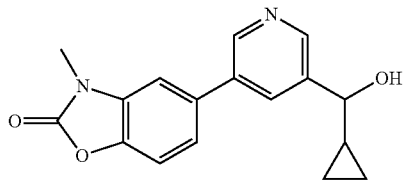 [SMILES: Cn1c(=O)oc2ccc(-c3cncc(C(O)C4CC4)c3)cc21]

The entitled compound was synthesized using the Suzuki coupling conditions described in example 11. ESI-MS m/z: 297.0 [M+1]+, Retention time 1.05 min: ¹HNMR (MeOD, 400.342 MHz) δ 0.49-0.72 (m, 4H), 1.18-1.26 (m, 1H), 3.47 (s, 3H), 4.13 (d, J=82 Hz, 1H), 7.37 (d, J=8.3 Hz, 1H), 7.47 (dd, J=8.3, 2 Hz, 1H), 7.50 (d, J=2 Hz, 1H), 8.15 (t, J=2 Hz, 1H), 8.58 (d, J=2 Hz, 1H), 8.72 (d, J=2 Hz, 1H). The enantiomers were separated by chiral HPLC (Ethanol-Heptane, v/v, 40%, ChiralPak IA-H column): peak 1 (enantiomer 1, retention time 16.37 min) and second peak (enantiomer 2, retention time 18.22 min).

Example 14

5-(5-(2-hydroxypropan-2-yl)pyridin-3-yl)-3-methyl-benzo[d]oxazol-2(3H)-one

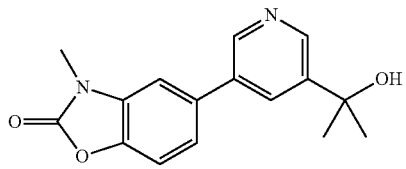 [SMILES: Cn1c(=O)oc2ccc(-c3cncc(C(C)(C)O)c3)cc21]

Step 1: Synthesis of 2-(5-Bromo-pyridin-3-yl)-propan-2-ol

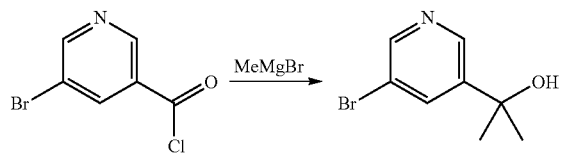

A solution of methylmagnesium chloride (3 M, 5 mL, 15 mmol) was added dropwise to a solution of 5-bromonicotinoyl chloride (661 mg, 3 mmol) in dry THF (15 mL) at −60° C. The resulting mixture was stirred at −60 to −50° C. for 4 h. The reaction mixture was quenched with saturated solution of NH4Cl and extracted with ethyl acetate (3×75 mL). The combined organic phase was washed with brine (100 mL), dried over anhydrous Na2SO4. After filtration and concentration, a pale yellow solid was obtained. ESI-MS m/z: 218.2 [M+1]+, Retention time 0.97 min; ¹HNMR (CDCl3, 400.342 MHz) δ 1.56 (s, 6H), 8.04 (t, J=2 Hz, 1H), 8.51 (d, J=2 Hz, 1H), 8.64 (d, J=2 Hz, 1H).

Step 2: Synthesis of 5-(5-(2-hydroxypropan-2-yl)pyridin-3-yl)-3-methylbenzo[d]oxazol-2(3H)-one

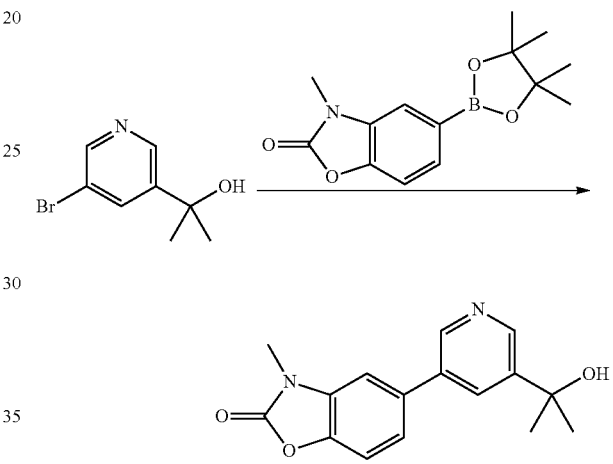

The above compound was synthesized using the Suzuki coupling conditions described in example 11. ESI-MS m/z: 285.2 [M+1]+, Retention time 1.01 min; ¹HNMR (DMSO-d6, 400.342 MHz) δ 1.53 (s, 6H), 3.42 (s, 3H), 7.7.44 (d, J=8 Hz, 1H), 7.48 (d, J=8 Hz, 1H), 7.66 (s, 1H), 8.10 (s, 1H), 8.69 (d, J=2 Hz, 1H), 8.76 (d, J=2 Hz, 1H).

Example 15

5-(5-(hydroxymethyl)pyridin-3-yl)-3-methylbenzo[d]oxazol-2(3H)-one

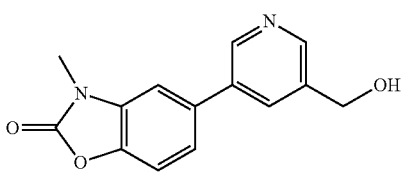 [SMILES: Cn1c(=O)oc2ccc(-c3cncc(CO)c3)cc21]

The entitled compound was synthesized using the Suzuki coupling conditions described in example 11. ESI-MS m/z: 257.1 [M+1]+, Retention time 0.90 min; ¹HNMR (DMSO-d6, 400.342 MHz) δ 3.42 (s, 3H), 4.63 (d, J=5.6 Hz, 2H), 5.40

(t, J=5.6 Hz, 1H), 7.44 (d, J=8 Hz, 1H), 7.48 (d, J=8 Hz, 1H), 8.02 (s, 1H), 8.53 (d, J=2 Hz, 1H), 8.81 (d, J=2 Hz, 1H).

Example 16

6-chloro-5-(5-(hydroxymethyl)pyridin-3-yl)-3-methylbenzo[d]oxazol-2(3H)-one

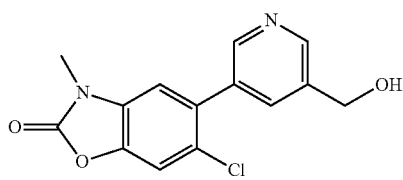 [SMILES: Cn1c(=O)oc2cc(Cl)c(-c3cncc(CO)c3)cc21]

Step 1: synthesis of
5-bromo-4-chloro-2-hydroxybenzamide

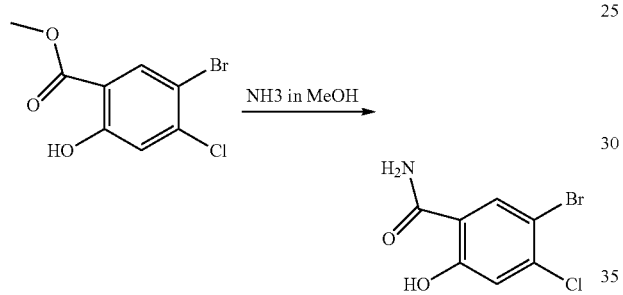

A mixture of methyl 5-bromo-4-chloro-2-hydroxybenzoate (2.655 g, 10.00 mmol) in a solution of ammonia (50.0 ml, 100 mmol) in MeOH was heated at 65° C. for 72 hr. After concentration, the title product was obtained as solid (2.53 g). ESI-MS m/z: 252.1 [M+1]$^+$, Retention time 1.19 min; $^1$HNMR (CDCl3, 400.342 MHz) δ 7.15 (s, 1H), 7.61 (s, 1H), 12.2 (brs, 1H).

Step 2: synthesis of
5-bromo-6-chlorobenzo[d]oxazol-2(3H)-one

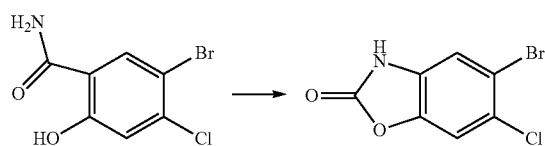 [SMILES: NC(=O)c1cc(Br)c(Cl)cc1O ; O=c1[nH]c2cc(Br)c(Cl)cc2o1]

Iodobenzene diacetate (1.610 g, 5.00 mmol) was added in three portions to a solution of 5-bromo-4-chloro-2-hydroxybenzamide (1.252 g, 5 mmol) and potassium hydroxide (0.561 g, 10.00 mmol) in MeOH (20 mL) at 0 T. The resulting mixture was stirred for at this temperature for hr, HCl (1M in water) was added to adjust the pH to ~7. The solution was concentrated, and heptanes (10 mL) were added. The resulting mixture was stirred for 30 min, and filtered. The solid was washed with water (5 mL) and collected and dried under vacuum to the title compound (1.15 g) as solid. ESI-MS 249.9 [M+1]$^+$, Retention time 1.23 min; $^1$HNMR (CDCl3, 400.342 MHz) δ 7.31 (s, 1H), 7.34 (s, 1H), 8.20 (brs, 1H).

Step 3: synthesis of
5-Bromo-6-chloro-3-methyl-3H-benzooxazol-2-one

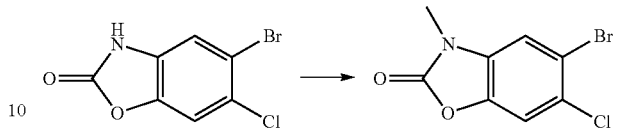

Iodomethane (0.579 ml . . . , 926 mmol) was added dropwise to a mixture of 5-bromo-6-chlorobenzo[d]oxazol-2(3H)-one (1.15 g, 4.63 mmol), potassium carbonate (1.599 g, 11.57 mmol) in DMSO (5 mL) at room temperature. The resulting mixture was stirred at this temperature for 18 h. Ethyl acetate (40 mL) was added and the mixture was stirred for 30 min and then filtered. The solution was washed with water (10 mL), brine (15 mL) and dried over Na2SO4. After filtration and concentration, a pale white solid was obtained (1.1 g). $^1$HNMR (400.342 MHz) δ 3.38 (s, 1H), 7.33 (s, 1H).

Step 4: synthesis of 6-Chloro-3-methyl-5-(4,4,5,5-tetramethyl-[1,3,2]dioxaborolan-2-yl)-3H-benzooxazol-2-one

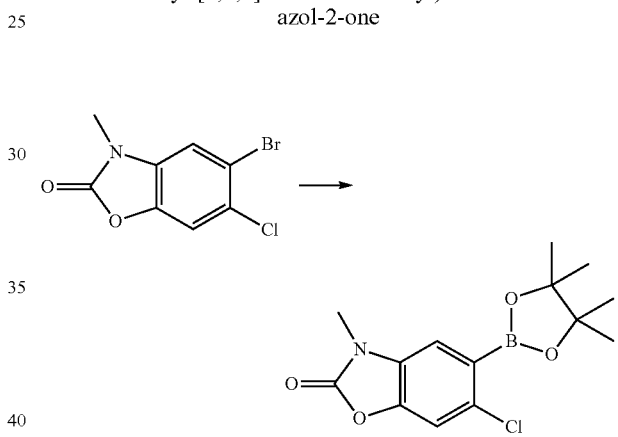

A mixture of 5-Bromo-6-chloro-3-methyl-3H-benzooxazol-2-one (1 g, 3.81 mmol), 4,4,5,5,4',4',5',5'-Octamethyl-[2,2']bi[[1,3,2]dioxaborolanyl] (0.967 g, 3.81 mmol), potassium acetate (0.748 g, 7.62 mmol) and PdCl2(dppf).CH$_2$Cl$_2$ adduct (0.156 g, 0.190 mmol) in 1,4-Dioxane (10 mL, dry) was heated to 80° C. for 4 hr. The mixture was concentrated, and the residue was purified by flash column (Ethyl Acetate-Heptanes, v/v, 10%-20%) and yielded colorless solid (460 mg). ESI-MS m/z: 310.3 [M+1]$^+$, Retention time 1.47 NMR (400.3 MHz, CDCl$_3$): δ 1.55 (s, 12H), 3.57 (s, 3H), 7.40 (s, 1H), 7.43 (s, 1H).

Step 5; synthesis of 6-chloro-5-(5-(hydroxymethyl)pyridin-3-yl)-3-methylbenzo[d]oxazol-2(3H)-one

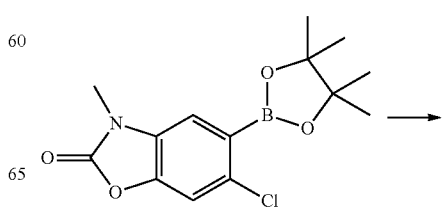

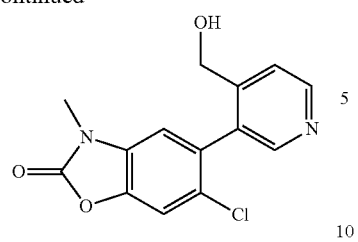

A mixture of 6-Chloro-3-methyl-5-(4,4,5,5-tetramethyl-[1,3,2]dioxaborolan-2-yl)-3H-benzooxazol-2-one (60 mg, 0.194 mmol), (5-Bromo-pyridin-3-yl)-methanol (36.4 mg, 0.194 mmol), polymer bound Pd(PPh3)4 (44.1 mg, 4.85 µmol) in DME (5 mL) was heated to 100° C. for 4 hr. After filtration through a pad of Na2SO4, the solution was concentrated, and the residue was purified by column (MeOH—CH2Cl2, v/v, 1%-2.5%-4.0%) and yielded colorless solid (25 mg). $^1$H NMR (400.3 MHz, CDCl$_3$): δ 3.35 (s, 3H), 4.77 (s, 2H), 6.85 (s, 1H), 7.31 (s, 1H), 7.74 (s, 1H), 8.53 (s, 1H), 8.57 (s, 1H). HRMS (ESI): calculated for $C_{14}H_{11}ClN_2O_3$: 290.04582. Found: 290.04666.

Example 17

5-(4-acetylpyridin-3-yl)-3-methylbenzo[d]oxazol-2(3H)-one

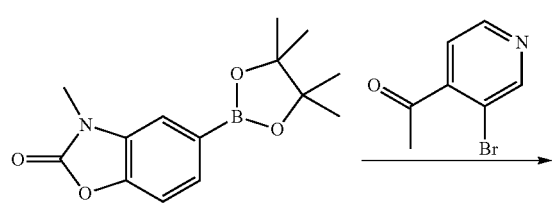

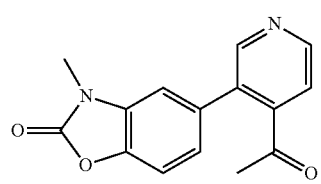

A mixture of 1-(3-bromopyridin-4-yl)ethanone (50 mg, 0.250 mmol), 3-methyl-5-(4,4,5,5-tetramethyl-1,3,2-dioxaborolan-2-yl)benzo[d]oxazol-2(3H)-one (68.8 mg, 0.250 mmol), polymer bound PalladiumTetrakis (56.8 mg, 6.25 µmol) and sodium carbonate (250 µl, 0.500 mmol) in toluene (1 mL) and ethanol (1 mL) was heated to 90° C. in microwave for 45 min. After filtration through a pad of Na2SO4, the solvent was removed in vacuum. The residue was purified by flash column (MeOH—CH$_2$Cl$_2$, v/v, 1%-1.5%) and yielded colorless solid (37 mg). ESI-MS m/z: 269.0 [M+1]$^+$, Retention time 1.03 min; $^1$H NMR (400.3 MHz, CDCl$_3$): δ 2.13 (s, 3H), 344 (s, 3H), 6.95 (d, J=1.48 Hz, 1H), 7.07 (dd, J=8.2, 1.68 Hz, 1H), 7.29 (d, J=8.2 Hz, 1H), 7.37 (d J=5 Hz, 1H), 8.69 (s, 1H), 8.73 (d, J=5 Hz, 1H).

Example 18

5-(5-(2-hydroxyethyl)pyridin-3-yl)-3-methylbenzo[d]oxazol-2(3H)-one

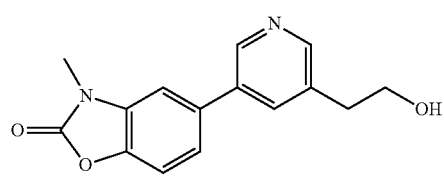 [SMILES: Cn1c(=O)oc2ccc(-c3cncc(CCO)c3)cc21]

Step 1: Synthesis of 2-(5-Bromo-pyridin-3-yl)-ethanol

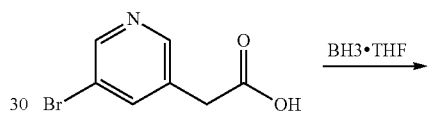

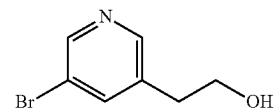

A solution of Diborane-THF complex (1.0 M in THF, 7.5 mL, 7.5 mmol) was added dropwise to a solution of 5-bromo-3-pyridinylacetic acid (1080 mg, 5 mmol) in dry THF at 0° C. The resulting mixture was allowed to warm to room temperature. After 15 h, the reaction mixture was cooled to 0° C. and water (10 mL) was added dropwise. The reaction mixture was diluted with ethyl acetate (100 mL). The organic layer was separated, washed with brine, dried over Na2SO4. After filtration and concentration, the residue was purified by flash column and afforded of the title compound as colorless solid (241 mg). $^1$HNMR (CDCl3, 400.342 MHz) δ 2.89 (t, J=6 Hz, 2H), 3.92 (t, J=6 Hz, 3H), 7.99 (s, 1H), 8.46 (s, 1H), 8.60 (s, 1H).

Step 2: Synthesis of 5-(5-(2-hydroxyethyl)pyridin-3-yl)-3-methylbenzo[d]oxazol-2(3H)-one 5-(5

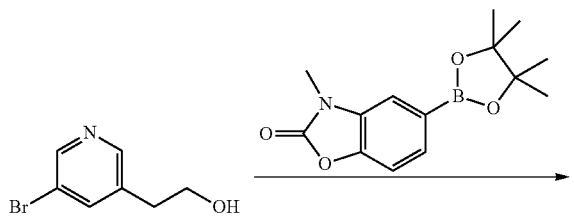

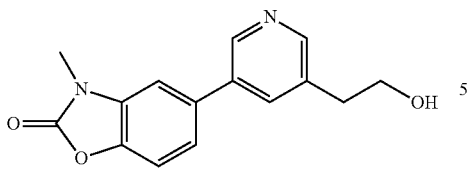

The above compound was synthesized using the Suzuki coupling conditions described in example 11. ESI-MS m/z: 271.2 [M+1]$^+$, Retention time 0.92 min; $^1$HNMR (MeOD, 400.342 MHz) δ 2.85 (t, J=6.5 Hz, 2H), 3.47 (s, 3H), 3.86 (t, J=6.5 Hz, 2H), 7.36 (d, J=8 Hz, 1H), 7.45 (dd, J=8, 2 Hz, 1H), 7.49 (d, J=2 Hz, 1H), 8.01 (s, 1H), 8.42 (d, J=2 Hz, 1H), 8.67 (d, J=2 Hz, 1H).

Example 19

3-methyl-5-(5-(2,2,2-trifluoro-1-hydroxyethyl)pyridin-3-yl)benzo[d]oxazol-2(3H)-one

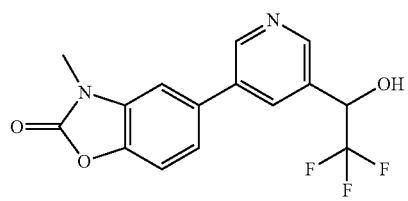 [SMILES: Cn1c(=O)oc2ccc(-c3cncc(C(O)C(F)(F)F)c3)cc21]

Step 1: Synthesis of 1-(5-bromopyridin-3-yl)-2,2,2-trifluoroethanol

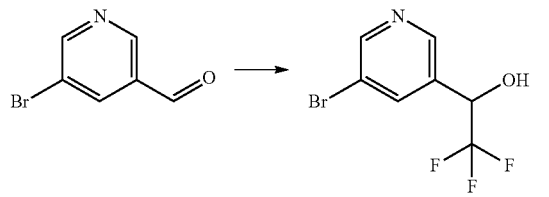 [SMILES: O=Cc1cncc(Br)c1 ; OC(c1cncc(Br)c1)C(F)(F)F]

A solution of Tetrabutylammonium fluoride (TBAF) (1.0 M in THF, 0.225 mL, 0.225 mmol) was added dropwise to the solution of 5-Bromo-pyridine-3-carbaldehyde (558 mg, 3 mmol) and trifluoromethyl)trimethylsilane (2.0 M in THF, 1.8 mL, 3.6 mmol) in THF (6 mL) at 5° C. The resulting pale brown reaction mixture was stirred at room temperature for 2 h. The reaction mixture was quenched by HCl (6 M). The mixture was neutralized by NaHCO3 and extracted with ethyl acetate (2×25 mL). The organic phase was washed with brine (30 mL), dried over anhydrous Na2SO4. After filtration and concentration, the title product was obtained as solid (498 mg). ESI-MS m/z: 257.9 [M+1]$^+$, Retention time 1.13 min;

$^1$HNMR (CDCl3, 400.342 MHz) δ 4.87-4.92 (m, 1H), 7.87 (s, 1H), 8.44 (d, J=2 Hz, 1H), 8.49 (d, J=2 Hz, 1H).

Step 2: Synthesis of 3-methyl-5-(5-(2,2,2-trifluoro-1-hydroxyethyl)pyridin-3-yl)benzo[d]oxazol-2(3H)-one

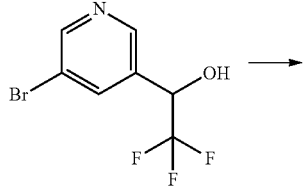

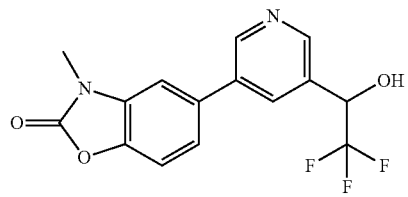

The entitled compound was synthesized using the Suzuki coupling conditions described in example 7, ESI-MS m/z: 224.9 [M+1]$^+$, Retention time 1.14 min; $^1$HNMR (MeOD, 400.342 MHz) δ 3.47 (s, 3H), 5.27-5.30 (m, 1H), 7.38 (d, J=8.2 Hz, 1H), 7.46 (dd, J=8.2, 1.56 Hz, 1H), 7.49 (s, 1H), 8.22 (s, 1H), 8.64 (s, 1H), 8.85 (s, 1H).

Example 20

N-(5-(3-methyl-2-oxo-2,3-dihydrobenzo[d]oxazol-5-yl)pyridin-3-yl)cyclopropanesulfonamide Step 1: Synthesis of Cyclopropanesulfonic acid (5-bromo-pyridin-3-yl)-amide Cyclopropanesulfonyl chloride was added dropwise to a solution of 5-Bromo-pyridin-3-ylamine (346 mg, 2 mmol), 4-dimethylaminopyridine (25 mg, 0.205 mmol) and triethylamine (0.558 mL, 4 mmol) in dichloromethane (4 mL) at room temperature under nitrogen. The reaction was stirred at this temperature for 15 h. The reaction mixture was diluted with ethyl acetate (50 mL) and the resulting solution was washed with saturated NaHCO$_3$ solution (25 mL). The aqueous phase was extracted with ethyl acetate (50 mL). The combined organic phase was dried over anhydrous Na$_2$SO$_4$. After filtration and concentration, the residue was purified by flash column (0-10% CH$_3$OH in CH$_2$Cl$_2$ v/v) and 248 mg of the desired product as a white solid was obtained. ESI-MS m/z: 278.9 [M+1]$^+$, Retention time 1.02 min; $^1$HNMR (MeOD, 400.342 MHz) δ 1.00-1.10 (m, 4H), 2.63-2.69 (m, 1H), 3.31 (s, 1H), 7.94 (t, J=2 Hz, 1H), 8.39 (s, 1H), 8.40 (d, J=2 Hz, 1H).

Step 2: Synthesis of N-(5-(3-methyl-2-oxo-2,3-dihydrobenzo[d]oxazol-5-yl)pyridin-3-yl)cyclopropanesulfonamide

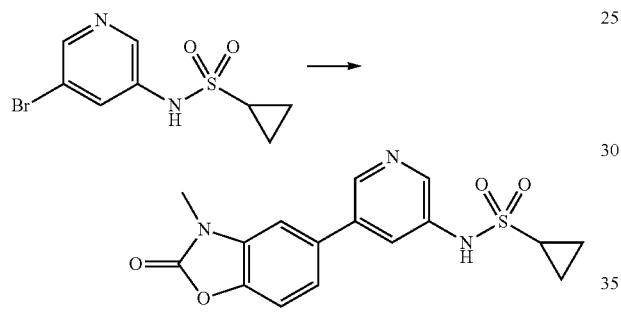

The above compound was synthesized using the Suzuki coupling conditions described in example 7. ESI-MS m/z: 346.0 [M+1]$^+$, Retention time 1.06 min; $^1$HNMR (MeOD, 400.342 MHz) δ 0.99-1.11 (m, 4H), 2.65-2.71 (m, 1H), 3.47 (s, 3H), 7.37 (d, J=8 Hz, 1H), 7.43 (dd, J=8, 2 Hz, 1H), 7.47 (d, J=2 Hz, 1H), 7.99 (t, J=2 Hz, 1H), 8.44 (d, J=2 Hz, 1H), 8.60 (d, J=2 Hz, 1H).

Example 21

N-methyl-N-(5-(3-methyl-2-oxo-2,3-dihydrobenzo[d]oxazol-5-yl)pyridin-3-yl)cyclopropanesulfonamide

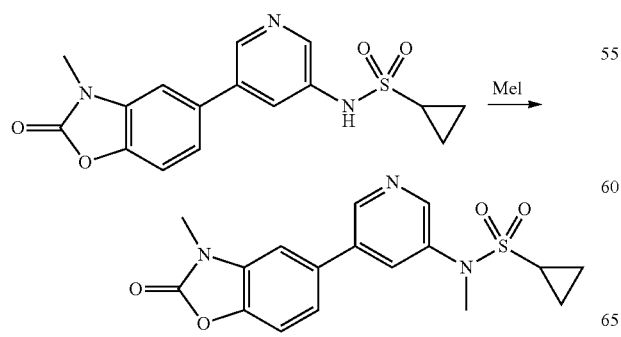

Iodomethane (55.4 mg, 0.39 mmol) was added dropwise to a suspension of N-(5-(3-methyl-2-oxo-2,3-dihydrobenzo[d]oxazol-5-yl)pyridin-3-yl)cyclopropanesulfonamide (104 mg, 0.3 mmol), potassium carbonate (207 mg, 1.5 mmol) in DMF (1.5 mL) at room temperature. The resulting mixture was stirred at this temperature for 4 h. The mixture was diluted with ethyl acetate (50 mL) and washed with water (2×50 mL). The aqueous layer was extracted with ethyl acetate (2×50 mL). The combined extracts were washed with NaHCO3 solution and dried over anhydrous Na2SO4. After filteration and concentration, the residue was treated with ether then filterated to pale solid (30 mg). ESI-MS m/z: 3601 [M+1]$^+$, Retention time 1.15 min; $^1$HNMR (MeOD, 400.342 MHz) δ 0.96-1.03 (m, 4H), 2.65-2.72 (m, 1H), 3.47 (s, 3H), 7.38 (d, J=8 Hz, 1H), 747 (dd J=8, 2 Hz, 1H), 7.52 (s, 1H), 8.18 (t J=2 Hz, 1H), 8.64 (d, J=2 Hz, 1H), 8.76 (s, 1H).

Example 22

N-(5-(6-fluoro-3-methyl-2-oxo-2,3-dihydrobenzo[d]oxazol-6-yl)pyridin-3-yl)ethanesulfonamide

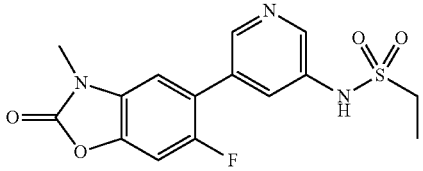 [SMILES: CCS(=O)(=O)Nc1cncc(-c2cc3c(cc2F)oc(=O)n3C)c1]

Step 1: Synthesis of 4-bromo-5-fluoro-2-nitro-phenol

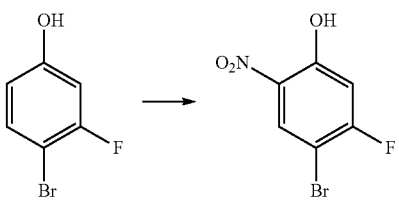 [SMILES: Oc1ccc(Br)c(F)c1 ; O=[N+]([O-])c1cc(Br)c(F)cc1O]

Iron(III) nitrate nonahydrate (4.19 g, 10.26 mmol) was added to a solution of 4-bromo-2-fluorophenol (10.0 g, 51.3 mmol) in THF (150 mL). The solution was cooled to 0° C. and nitric acid (12.93 g, 205 mmol) was added. At the end of addition, the cooling bath was removed, TLC analysis indicated partial conversion after overnight stirring and the temperature was raised to 45° C. Complete conversion was observed after another 7 h. The mixture was diluted with ethyl acetate (500 mL), washed with water (4 times 200 mL) and brine (200 mL). The organic phase was dried over MgSO$_4$, filtered and concentrated. The residue was purified by silica gel flash chromatography to give 4-bromo-5-fluoro-2-nitro-phenol. $^1$H NMR (400 MHz, CHLOROFORM-d) δ ppm 6.96 (d, J=8.8 Hz, 1H), 8.40 (d, J=7.1 Hz, 1H), 10.69 (d, J=1.5 Hz, 1H).

Step 2: Synthesis of 2-amino-4-bromo-5-fluorophenol

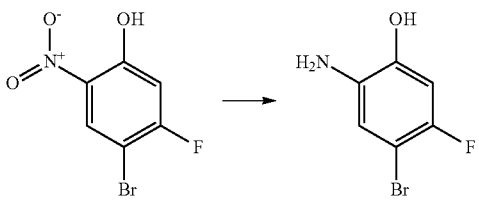 [SMILES: O=[N+]([O-])c1cc(Br)c(F)cc1O ; Nc1cc(Br)c(F)cc1O]

Tin(II) chloride dihydrate (16.83 g, 74.6 mmol) was added to a solution of 4-bromo-5-fluoro-2-nitrophenol (4.4 g, 18.64 mmol) in ethanol (180 mL). The mixture was flushed with nitrogen and heated to 85° C. (oil bath temperature) for 1 day. The mixture was diluted with ethyl acetate (500 mL), saturated aqueous sodium bicarbonate (200 mL) was added with vigorous stirring. The mixture was filtered through celite and the celite pad was repeatedly washed with ethyl acetate. The two phases were separated and the organic phase was washed with brine. The combined aqueous phase was extracted with ethyl acetate. The combined organic phase was dried over MgSO$_4$, filtered and concentrated to give 2-amino-4-bromo-5-fluorophenol. $^1$H NMR (400 MHz, DMSO-d$_6$) δ ppm 4.61 (br. s., 2H) 6.60 (d, J=10.11 Hz, 1H) 6.76 (d, J=7.33 Hz, 1H) 9.69 (br. s., 1 H).

Step 3: Synthesis of
5-bromo-6-fluorobenzo[d]oxazol-2(3H)-one

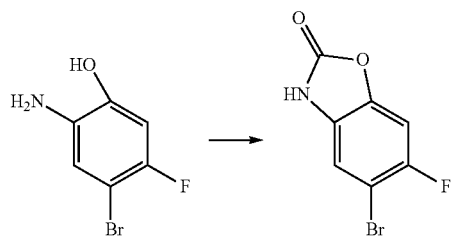 [SMILES: Nc1cc(Br)c(F)cc1O ; O=c1[nH]c2cc(Br)c(F)cc2o1]

A flask was charged with 2-amino-4-bromo-5-fluorophenol (3.3 g, 18.84 mmol) and THF (200 mL), and CDI (3.05 g, 18.84 mmol) was added. The mixture was heated to 60° C. for 2 h. The mixture was diluted with EtOAc and washed with 1N HCl in water. The organic phase was dried over Na$_2$SO$_4$ and concentrated to give 5-bromo-6-fluorobenzo[d]oxazol-2 (3H)-one. $^1$H NMR (400 MHz, DMSO-d$_6$) δppm 7.38 (d, J=6.06 Hz, 1H) 7.56 (d, J=8.34 Hz, 1H) 11.88 (br. s., 1H).

Step 4: Synthesis of
5-bromo-6-fluoro-3-methylbenzo[d]oxazol-2(3H)-one

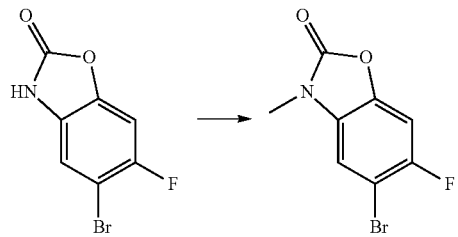

A flask was charged with 5-bromo-6-fluorobenzo[d]oxazol-2(3H)-one (3.6 g, 14.74 mmol) and DMSO (150 mL), and MeI (4.18 g, 29.5 mmol) and potassium carbonate (5.09 g, 36.9 mmol) were added. The mixture was stirred at room temperature overnight. The mixture was poured to water (1.2 L) and the precipitate was filtered, washed with water and dried under high vacuum at 60° C. for 1 h to give 5-bromo-6-fluoro-3-methylbenzo[d]oxazol-2(3H)-one. $^1$H NMR (400 MHz, DMSO-d$_6$) δ ppm 3.32 (s, 3H) 7.62 (d, J=8.34 Hz, 1H) 7.70 (d, J=6.06 Hz, 1H).

Step 5: Synthesis of 6-fluoro-3-methyl-5-(4,4,5,5-tetramethyl-1,12-dioxaborolan-2-yl)benzo[d]oxazol-2(3H)-one

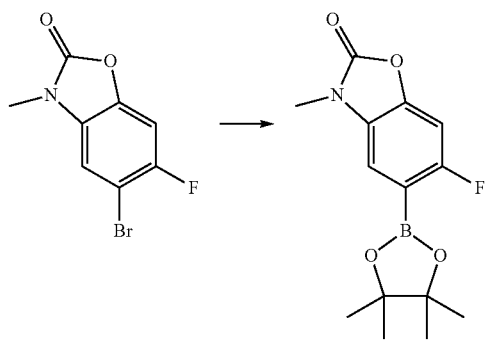 [SMILES: Cn1c(=O)oc2cc(F)c(Br)cc21 ; Cn1c(=O)oc2cc(F)c(B3OC(C)(C)C(C)(C)O3)cc21]

A flask was charged with 5-bromo-6-fluoro-3-methyl-benzo[d]oxazol-2(3H)-one (246 mg, 1.0 mmol), 4,4,4',4',5,5,5',5'-octamethyl-2,2'-bi(1,3,2-dioxaborolane) (381 mg, 1.5 mmol) and potassium acetate (294 mg, 3.0 mmol), and 1,4-dioxane (10 mL) was added. The mixture was flushed with N$_2$ for 5 min. PdCl$_2$(dppf).CH$_2$Cl$_2$ (37 mg, 0.050 mmol) was added. The mixture was stirred at 90° C. overnight. The mixture was cooled to room temperature and silica gel (5 g) was added. The suspension was concentrated and the residue was purified by silica chromatography eluting with a 0 to 40% EtOAc-heptane gradient to give 6-fluoro-3-methyl-5-(4,4,5,5-tetramethyl-1,3,2-dioxaborolan-2-yl)benzo[d]oxazol-2 (3H)-one, $^1$H NMR (400 MHz, CHLOROFORM-d) δ ppm 1.38 (s, 12 H) 3.42 (s, 3H) 6.97 (d, J=8.08 Hz, 1H) 7.26 (d, J=8.08 Hz, 1H).

Step 6: Synthesis of
N-(5-bromopyridin-3-yl)ethanesulfonamide

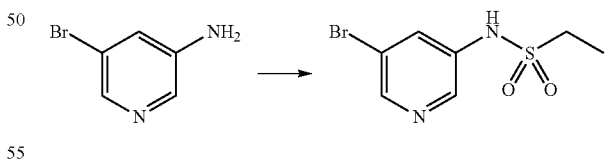

To a solution of 5-bromopyridin-3-amine (1.73 g, 10 mmol) and triethylamine (4.05 g, 40 mmol) in DCM (100 mL) was added a solution of ethanesulfonyl chloride (3.86 g, 30 mmol) in DCM (20 mL) at 0° C. The mixture was stirred at 0° C. for 1 h. 1N NaOH in water (10 mL) and methanol (20 mL) were added and the mixture was concentrated in vacuo, Silica gel (20 g) and DCM (100 mL) were added and the mixture was concentrated in vacuo. The residue was purified by silica chromatography eluting with a 0 to 5% MeOH- DCM gradient to give N-(5-bromopyridin-3-yl)ethanesulfonamide. ESI-MS: m/z 265.2, 267.2 (M+H)+.

Step 7: Synthesis of N-(5-(6-fluoro-3-methyl-2-oxo-2,3-dihydrobenzo[d]oxazol-5-yl)pyridin-3-yl)ethanesulfonamide

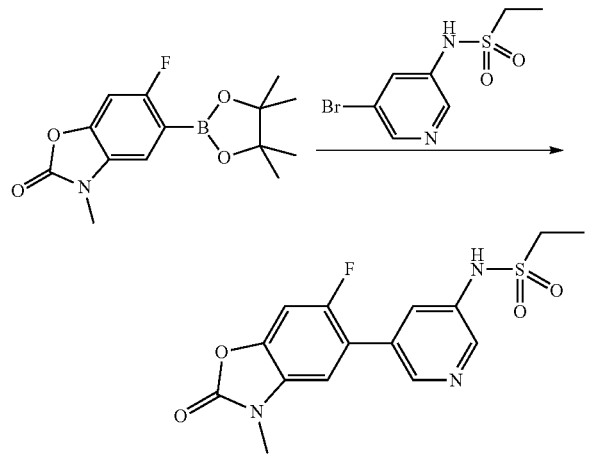

A flask was charged with 6-fluoro-3-methyl-5-(4,4,5,5-tetramethyl-1,3,2-dioxaborolan-2-yl)benzo[d]oxazol-2(3H)-one (220 mg, 0.751 mmol), N-(5-bromopyridin-3-yl)ethanesulfonamide (133 mg, 0.5 mmol), K$_3$PO$_4$ (212 mg, 1.0 mmol) and Pd(PPh$_3$)$_4$ (28.9 mg, 0.025 mmol). The flask was flushed with N$_2$ and DMF (5 mL) was added. The mixture was stirred under N$_2$ at 100° C. for 1 h. The mixture was cooled to room temperature, diluted with EtOAc (100 mL) and filtered through a pad of celite. The celite pad was washed with EtOAc (100 mL) and the combined organic phase was washed with water (50 mL*2) and brine (50 mL), dried over Na$_2$SO$_4$ and concentrated in vacuo. The residue was purified by silica chromatography eluting with a 0 to 80% EtOAc-heptane gradient to give N-(5-(6-fluoro-3-methyl-2-oxo-2,3-dihydrobenzo[d]oxazol-5-yl)pyridin-3-yl)ethanesulfonamide. $^1$H NMR (400 MHz, DMSO-d$_6$) d ppm 1.23 (t, J=7.33 Hz, 3H) 3.21 (q, J=7.33 Hz, 2H) 3.38 (s, 3H) 7.53 (d, J=6.57 Hz, 1H) 7.58 (d, J=10.11 Hz, 1H) 7.79 (q, J=1.85 Hz, 1H) 8.47 (d, J=2.27 Hz, 1H) 8.49 (t, J=1.52 Hz, 1H) 10.20 (s, 1H). HRMS: (ESI) m/z 352.0769 [(M+H)+Calcd for C15H15FN3O4S 352.07618].

Example 23

N-((5-(3-methyl-2-oxo-2,3-dihydrobenzo[d]oxazol-5-yl)pyridin-3-yl)methyl)ethanesulfonamide

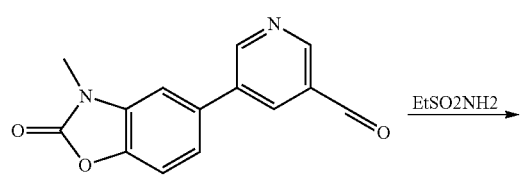

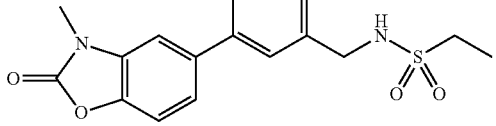

A mixture of 5-(3-Methyl-2-oxo-2,3-dihydro-benzooxazol-5-yl)-pyridine-3-carbaldehyde (51 mg, 0.2 mmol), ethanesulfonamide (33 mg, 0.3 mmol), Ti(OiPr)4 (118 uL, 114 mg, 0.4 mmol) in toluene (5 mL) was heated to reflux for overnight. After concentration, the residue was dissolved into CH2Cl2 (5 mL). NaBH(OAc)$_3$ (127 mg, 0.6 mmol) was added at room temperature. The resulting mixture was stirred for 4 h at this temperature. Saturated NaHCO3 solution was added, and the mixture was extracted with CH2Cl2. The combined extracts were dried over anhydrous Na2SO4. After filteration and concentration, the residue was purified by flash column (MeOH—CH2Cl2, v/v, 1-3.5%) and afforded the title product (50 mg), ESI-MS m/z: 348.0 [M+1]+, Retention time 1.01 min; $^1$HNMR (CDCl3, 400.342 MHz) δ 1.40 (t, J=7.4 Hz, 3H), 3.07 (q, J=7.4 Hz, 2H), 3.48 (s, 3H), 4.42 (d, J=6 Hz, 2H), 4.60 (t, J=6 Hz, 1H), 7.13 (s, 1H), 7.31 (s, 2H), 7.92 (s, 1H), 8.57 (d, J=14 Hz, 1H), 8.77 (d, J=1.4 Hz, 1H).

Example 24

1,1,1-trifluoro-N-((5-(3-methyl-2-oxo-2,3-dihydrobenzo[d]oxazol-5-yl)pyridin-3-yl)methyl)ethanesulfonamide

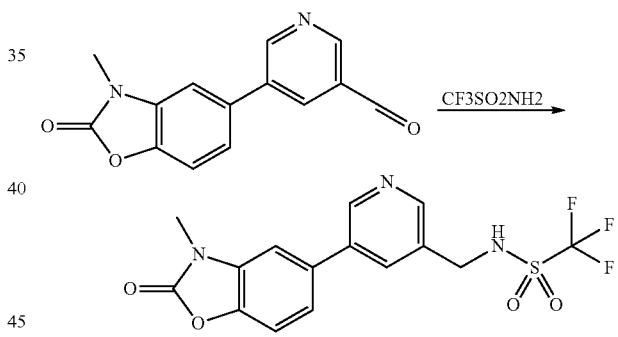

The entitled compound was synthesized using the reductive amination procedure described in example 23. The reductive amination procedure in example 24 was used here. ESI-MS z: 387.9 [M+1]+, Retention time 1.12 min; $^1$HNMR (CDCl3, 400.342 MHz) δ 3.41 (s, 3H) 4.51 (s, 2H), 7.06 is 1H), 7.24 (s, 2H), 7.81 (s, 1H), 8.49 (s, 1H), 8.74 (s, 1H).

Example 25

2,2,2-trifluoro-N-((5-(3-methyl-2-oxo-2,3-dihydrobenzo[d]oxazol-5-yl)pyridin-3-yl)methyl)ethanesulfonamide

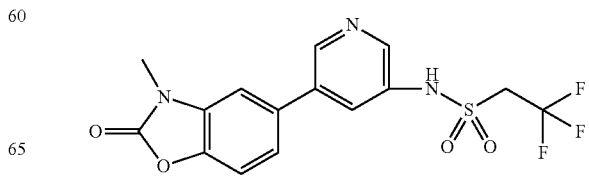

The entitled compound was synthesized using procedure described in example 20. ESI. MS m/z: 388.0 [M+1]+, Retention time 1.10 min; ¹HNMR (MeOD, 400.342 MHz) δ 3.47 (s, 3H), 4.34 (q, J=9.4 Hz, 2H), 7.38 (d, J=8 Hz, 1H), 7.44 (dd, J=8, 2 Hz, 1H), 7.48 (d, J=2 Hz, 1H), 7.98 (t, J=2 Hz, 1H), 8.43 (d, J=2 Hz, 1H), 8.64 (d, J=2 Hz, 1H).

Example 26

N-(5-(3-methyl-2-oxo-2,3-dihydrobenzo[d]oxazol-5-yl)pyridin-3-yl)ethanesulfonamide

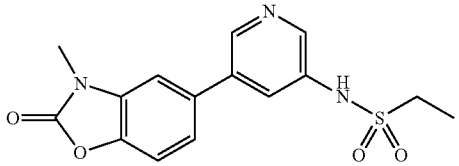 [SMILES: CCS(=O)(=O)Nc1cncc(-c2ccc3oc(=O)n(C)c3c2)c1]

The entitled compound was synthesized using procedure described in example 20 ESI-MS m/z: 388.0 [M+1]+, Retention time 1.10 min; ¹HNMR (MeOD, 400.342 MHz) δ 3.47 (s, 3H), 4.34 (q, J=9.4 Hz, 2H), 7.38 (d, J=8 Hz, 1H), 7.44 (dd, J=8, 2 Hz, 1H), 7.48 (d, J=2 Hz, 1H), 7.98 (t, J=2 Hz, 1H), 8.43 (d, J=2 Hz, 1H), 8.64 (d, J=2 Hz, 1H).

Example 27

N-(5-(3-methyl-2-oxo-2,3-dihydrobenzo[d]oxazol-6-yl)pyridin-3-yl)propane-2-sulfonamide

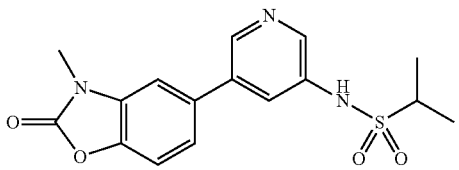 [SMILES: CC(C)S(=O)(=O)Nc1cncc(-c2ccc3oc(=O)n(C)c3c2)c1]

The entitled compound was synthesized using procedure described in example 20. ESI-MS m/z: 334.0 [M+1]+, Retention time 1.03 min; ¹HNMR (MeOD, 400.342 MHz) δ 1.56 (t, J=7.3 Hz, 3H), 321 (q, J=7.3 Hz, 1H), 3.47 (s, 3H), 7.37 (s, 1H), 7.41 (d, J=1.6 Hz, 1H), 7.46 (d, J=1.6 Hz, 1H), 7.95 (s, 1H), 8.41 (s, 1H), 8.57 (s, 1H).

Example 28

N-(5-(3-methyl-2-oxo-2,3-dihydrobenzo[d]oxazol-5-yl)pyridin-3-yl)propane-1-sulfonamide

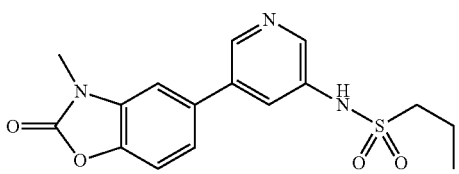 [SMILES: CCCS(=O)(=O)Nc1cncc(-c2ccc3oc(=O)n(C)c3c2)c1]

The entitled compound was synthesized using procedure described in example 20. ESI-MS m/z: 348.1 [M+1]+, Retention time 1.11 min, ¹HNMR (CD2Cl2, 400.342 MHz) δ 0.96 (t, J=7.3 Hz, 3H), 1.73-1.83 (m, 2H), 2.98-3.07 (m, 2H), 3.36 (s, 3H), 7.10 (s, 1H), 7.21 (5, 1H), 7.23 (s, 1H), 7.77 (s, 1H), 8.33 (s, 1H), 8.55 (s, 1H).

Example 29

5-(5-(1-amino-2,2,2-trifluoroethyl)pyridin-3-yl)-3-methylbenzo[d]oxazol-2(3H)-one

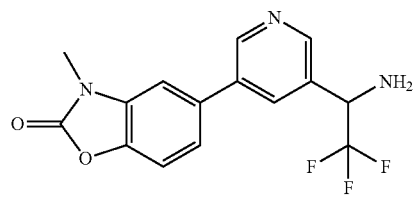 [SMILES: Cn1c(=O)oc2ccc(-c3cncc(C(N)C(F)(F)F)c3)cc21]

Step 1: Synthesis of N-(1-(5-bromopyridin-3-yl)-2,2,2-trifluoroethyl)-2-methylpropane-2-sulfinamide

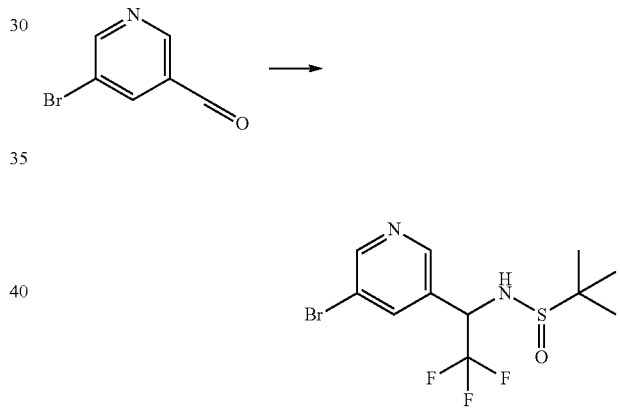

A mixture of 3-(3-Methyl-2-oxo-2,3-dihydro-benzooxazol-5-yl)-pyridine-4-carbaldehyde (730 mg, 3.92 mmol) and 2-Methyl-propane-2-sulfinic acid amide (523 mg, 4.32 mmol) and Titanium isopropoxide (4.7 mL, 15.7 mmol) in toluene (20 mL) was stirred at room temperature for overnight. Brine (8 mL) was added and the precipitate was removed and washed with ethyl acetate. The combined filtrates were dried over anhydrous Na2SO4. After filtration and concentration, the residue and TBAT (2.32 g, 4.3 mmol) was dissolved in THF (75 mL) and cooled to −50° C. A solution of TMSCF3 (2 M in THF, 2.344 mL, 4.69 mmol) was added dropwise and resulting mixture was stirred at −50° C. for 1.5 h. The reaction was quenched with saturated NH4Cl solution and diluted with ethyl acetate. The organic layer was separated, and dried over anhydrous Na2SO4. After filtration and concentration, the residue was purified by flash column (MeOH—CH2Cl2, v/v, 0-10%) and afforded colorless solid (340 mg). ¹HNMR (DMSO-d6, 400.342 MHz) δ 1.16 (s, 9H), 5.51 (m, 1H), 6.57 (d, J=9.9 Hz, 1H), 8.39 (t, J=2 Hz, 1H), 8.77 (d, J=2 Hz, 1H), 8.80 (d, 2 Hz, 1H).

(dd, J=8, 2 Hz, 1H), 7.52 (d, J=2 Hz, 1H), 8.28 (s, 1H), 8.64 (d, J=2 Hz, 1H), 8.86 (d, J=2 Hz, 1H).

Step 2: Synthesis of 1-(5-bromopyridin-3-yl)-2,2,2-trifluoroethanamine

Example 30

N-(cyclopropyl(5-(3-methyl-2-oxo-2,3-dihydrobenzo[d]oxazol-5-yl)pyridin-3-yl)methyl)ethanesulfonamide

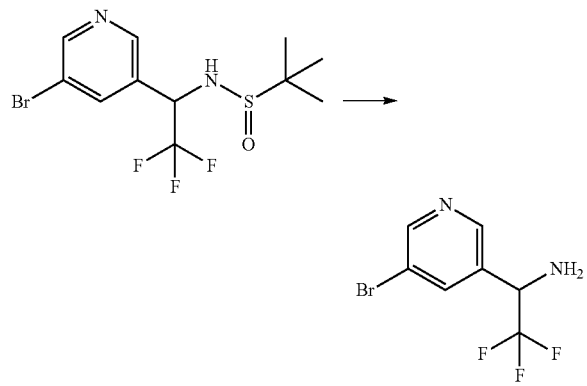

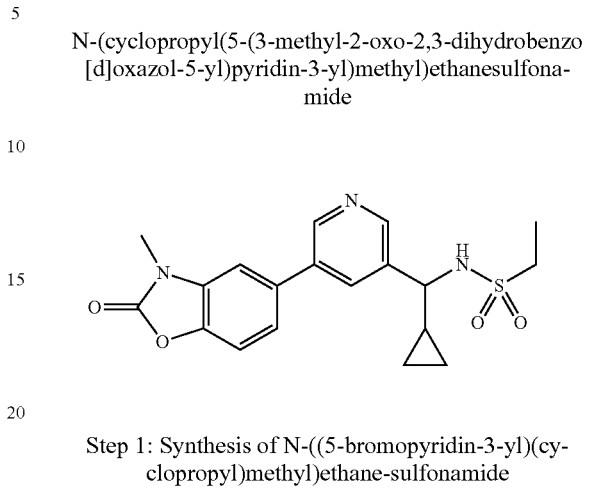

Step 1: Synthesis of N-((5-bromopyridin-3-yl)(cyclopropyl)methyl)ethane-sulfonamide A solution of HCl (4 M in dioxane, 0.557 m, 2.23 mmol) was added to a solution of N-(1-(5-bromopyridin-3-yl)-2,2,2-trifluoroethyl)-2-methylpropane-2-sulfinamide (400 mg, 1.114 mmol) in MeOH (2.5 mL) at room temperature. The resulting mixture was stirred at this temperature for overnight. The solvent was removed in vacuum, and the residue was treated with saturated NaHCO3 solution and extracted with ethyl acetate. The combined extracts were dried over anhydrous Na2SO4. After filtration and concentration, the title compound was obtained (230 mg). ESI-MS m/z: 256.9 [M+1]+; Retention time 1.02 min;

$^1$HNMR (MeOD, 400.342 MHz) δ 4.61 (q, J=7.7 Hz, 1H), 8.21 (s, 1H), 8.62 (d, J=2 Hz, 1H), 8.67 (d, J=2 Hz, 1H).

Step 3: Synthesis of 5-(5-(1-amino-2,2,2-trifluoroethyl)pyridin-3-yl)-3-methylbenzo[d]oxazol-2(3H)-one A mixture of 5-bromonicotinaldehyde (1.860 g, 10 mmol), ethanesulfonamide (1.091 g, 10.00 mmol) and titanium(IV) isopropoxide (5.86 ml, 20.00 mmol) in Toluene (20 mL) was heated to reflux for 2 hr. After concentration, the residue was dissolved in THF (25 mL) and cooled to −40° C. A solution of cyclopropylmagnesium bromide (50.0 ml, 25.00 mmol) was added dropwise and the resulting mixture was slowly warmed up to −20° C. and stirred at this temperature for 4 hr. After quenched by NH4Cl solution, filtration, extraction with CH2Cl2, the solution was dried over Na2SO4, and concentrated, the residue was purified by flash column (ethyl acetate heptane, v/v, 10%-35%) and yielded the title compound (1.5 g). $^1$H NMR (400.3 MHz, CDCl$_3$): δ0.2-0.3 (m, 1H), 0.4-0.5 (m, 1H), 0.5-0.6 (m, 1H), 0.6-0.7 (m, 1H), 1.0-1.1 (m, 1H), 1.1-1.2 (m, 3H), 2.55-2.75 (m, 2H), 3.8-3.7 (m, 1H), 4.51 (brd, J=4.8 Hz, 1H), 7.73 (s, 1H), 8.42 (s, 1H), 8.51 (s, 1H).

Step 2: Synthesis of N-(cyclopropyl(5-(3-methyl-2-oxo-2,3-dihydrobenzo[d]oxazol-5-yl)pyridin-3-yl)methyl)ethanesulfonamide

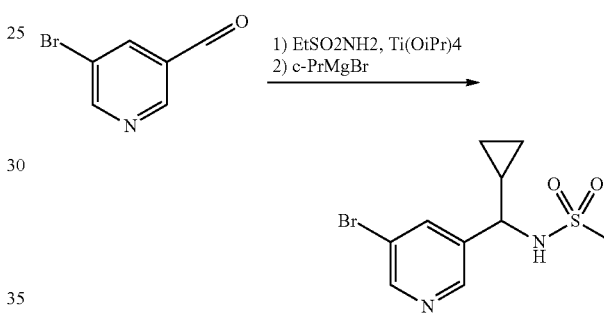

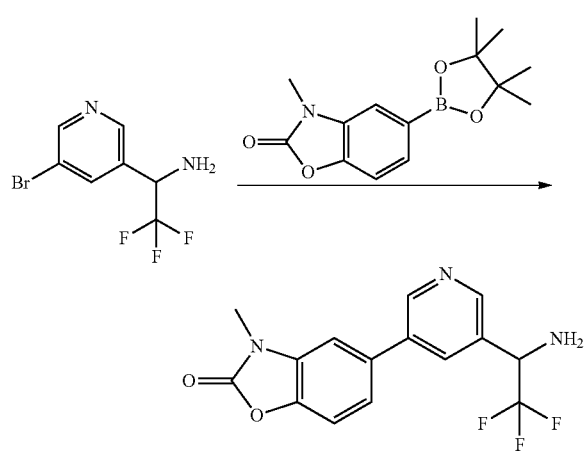

The entitled compound was synthesized using Suzuki procedure described in example 7. ESI-MS m/z: 324.0 [M+1]+; Retention time 1.08 min; $^1$HNMR (MeOD, δ00.342 MHz) δ 3.48 (s, 3H), 4.68 (q, J=7.6 Hz, 1H), 7.38 (d, J=8 z, 1H), 7.48

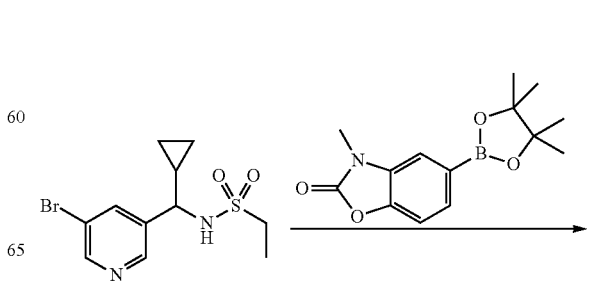

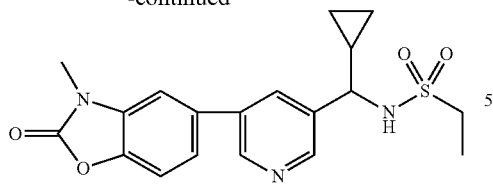

The mixture of 3-Methyl-5-(4,4,5,5-tetramethyl-[1,3,2]di-oxaborolan-2-yl)-3H-benzooxazol-2-one (115 mg, 0.42 mmol), N-((5-bromopyridin-3-yl)(cyclopropyl)methyl)ethane-sulfonamide (133 mg, 0.42 mmol), PdCl2(dppf).CH2Cl2 (34 mg, 0.04 mmol) and Na2CO3 (2 M in water, 0.42 mL, 0.83 mmol) in DMF (6 mL) was heated at 100° C. for 3 h. After concentration, the residue was diluted with DCM, and subsequently filtered to remove insoluble solid. The filtrate was concentrated and purified by flash column (MeOH—CH2Cl2, v/v, 0-4%) to give N-(cyclopropyl(5-(3-methyl-2-oxo-2,3-dihydrobenzo[d]oxazol-5-yl)pyridin-3-yl)methyl)ethanesulfonamide (87 mg, 54%); ESI-MS m/z: 388 [M+1]$^+$, Retention time 1.35 min; $^1$H-NMR (MeOD, 400 MHz) δ 8.80 (1H, d, J=2.0 Hz), 8.62 (1H, d, J=2.0 Hz), 8.20 (1H, t, J=2.0 Hz), 7.54 (1H, d, J=2.4 Hz), 7.50 (1H, dd, J=8.4, 24 Hz), 7.42 (1H, d, J=84 Hz), 3.95 (1H, d, J=8.8 Hz), 3.52 (3H, s), 3.05-2.92 (2H, m), 1.36-1.30 (1H, m), 1.30 (1H, t, J=7.2 Hz), 0.81-0.77 (1H, m), 0.66-0.62 (2H, m), 0.55-0.47 (1H, m)

Example 31

3-methyl-5-(4-(2,2,2-trifluoro-1-hydroxyethyl)pyridin-3-yl)benzo[d]oxazol-2(3H)-one

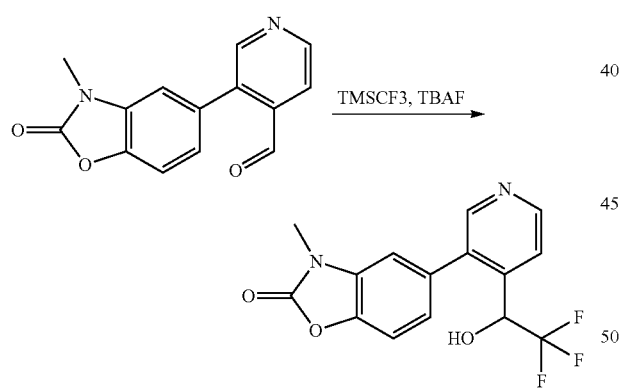

A solution of TBAF in THF (1M, 0.02 mL, 0.02 mmol) was added dropwise to a mixture of 3-(3-Methyl-2-oxo-2,3-dihydro-benzooxazol-5-yl)-pyridine-4-carbaldehyde (54 mg, 0.21 mmol) and (trifluoromethyl)trimethyl silane (0.2 mL, 0.42 mmol) in THF (0.8 mL) at 5° C. under nitrogen. After 5 min at this temperature, TBAF (1M in THF, 1 mL, 1 mmol) was added. The resulting solution was diluted with ethyl acetate and water. The organic layer was washed with brine and dried over anhydrous Na2O4. After concentration, the residue was purified by PTLC (10% MeOH in DCM, v/v) gave 3-Methyl-5-[4-(2,2,2-trifluoro-1-hydroxy-ethyl)-pyridin-3-yl]-3H-benzooxazol-2-one. (13 mg, 19%); ESI-MS m/z: 325 [M+1]$^+$, Retention time 1.53 min; 1H-NMR (MeOD, 400 MHz) δ 8.65 (1H, d, 5.6 Hz), 8.50 (1H, s), 7.79 (1H, d, J=5.6 Hz), 7.39 (1H, d, J=8.0 Hz), 7.17 (1H d, J=1.6 Hz), 7.12 (1H, dd, J=8.0, 1.6 Hz), 5.16 (1H, q, J=6.8 Hz), 3.43 (3H, s).

Example 32

5-(4-(cyclopropyl(hydroxy)methyl)pyridin-3-yl)-3-methylbenzo[d]oxazol-2(3H)-one

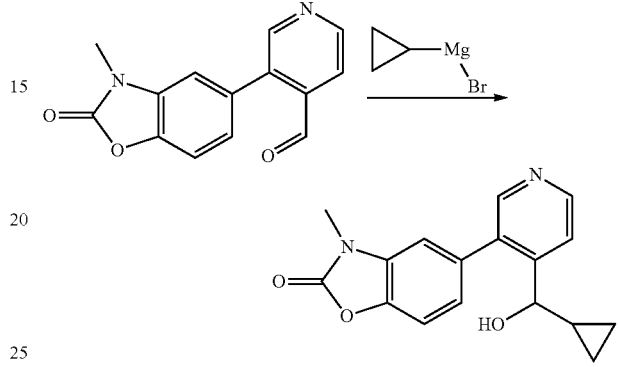

Cyclopropylmagnesium bromide (0.5 M in THF, 3.5 mL, 1.8 mmol) was added dropwise to a solution of 3-(3-Methyl-2-oxo-2,3-dihydro-benzooxazol-5-yl)-pyridine-4-carbaldehyde (150 mg, 0.58 mmol) in THF (1.6 mL) at −36'C. The resulting mixture was stirred at this temperature for 3 h, and the reaction was quenched by the addition of saturated NH4Cl solution. The mixture was diluted with ethyl acetate and water. The organic layer was separated and dried over anhydrous Na2SO4. After filtration and concentration, the residue was purified by flash column (MeOH/DCM, v/v, 0-4%) to give the title compound. (67 mg, 39%); ESI-MS m/z 297.2 [M+1]$^+$, Retention time 1.00 min; $^1$HNMR (CDCl$_3$, 400.342 MHz) δ ppm −0.27-0 (m, 1H), 0.36-0.45 (m, 2H), 0.52-0.57 (m, 1H), 0.96-1.02 (m, 1H), 3.47 (s, 3H), 4.52 (d, J=7.6 Hz, 1H), 7.14 (dd, J=8, 1.6 Hz, 1H), 7.25 (d, J=1.6 Hz, 1H), 7.33 (d, J=: 8 Hz, 1H), 8.18 (d, J=6 Hz, 1H), 8.47 (s, 1H), 8.63 (d, J=6 Hz, 1H).

Example 33

5-(4-(1-hydroxypropyl)pyridin-3-yl)-3-methylbenzo[d]oxazol-2(3H)-one

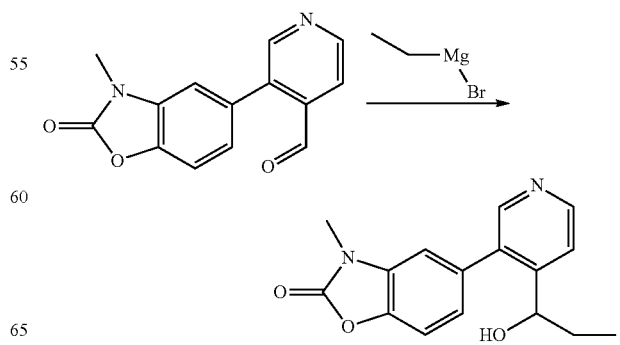

Ethylmagnesium bromide (3 M in THF, 0295 mL, 0.885 mmol) was added dropwise to a solution of 3-(3-Methyl-2-oxo-2,3-dihydro-benzooxazol-5-yl)-pyridine-4-carbaldehyde (75 mg, 0.295 mmol) in THF (2 mL) at −36° C. The resulting mixture was stirred at this temperature for 3 h, and the reaction was quenched by the addition of saturated NH4Cl solution. The mixture was diluted with ethyl acetate and water. The organic layer was separated and dried over anhydrous Na2SO4. After filtration and concentration, the residue was purified by reverse phase chromatography (10%-100%, v/v, ACN-water), 6 mg of desired product was obtained. ESI-MS m/z: 285.1 [M+1]$^+$, Retention time 1.00 min; $^1$HNMR (CDCl$_3$, 400.342 MHz) δ ppm 0.74 (t, J=7.3 Hz, 3H), 1.47-1.53 (m, 2H), 3.40 (s, 3H), 4.93 (t, J=5.5 Hz, 1H), 7.03 (dd, J=8.1, 1.2 Hz, 1H), 7.16 (s, 1H), 7.25 (d, J=8.1 Hz, 1H), 8.03 (d, J=5 Hz, 1H), 8.36 (s, 1H), 8.52 (d, J=5 Hz, 1H).

Example 34

3-methyl-5-(4-(oxetan-2-yl)pyridin-3-yl)benzo[d]oxazol-2(3H)-one

Step 1: Synthesis of 3-Bromo-4-oxiranyl-pyridine

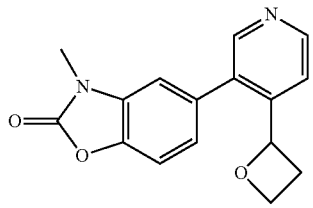 [SMILES: Cn1c(=O)oc2ccc(-c3cnccc3C3CCO3)cc21]

To a solution of sulfonium salt (7.39 g, 33.6 mmol) in DMSO (40 mL) was added sodium hydride (60% in oil, 1.236 g, 30.9 mmol) at room temperature. After 15 min of stirring, 3-Bromo-pyridine-4-carbaldehyde (930 mg, 5 mmol) in DMSO (20 was added slowly at this temperature. After addition, the resulting mixture was stirred for another 30 min, and was subsequently quenched with brine. The mixture was extracted with ethyl acetate twice. The combined extracts were dried over anhydrous Na2SO4. After filtration and concentration, the title compound was obtained (200 mg).

Step 2: Synthesis of 3-Bromo-4-oxetan-2-yl-pyridine

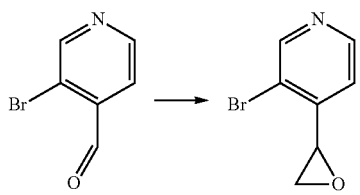 [SMILES: O=Cc1ccncc1Br ; Brc1cnccc1C1CO1]

potassium tert-butoxide (561 mg, 5 mmol) was added to a solution of sulfonium salt (1100 mg, 5 mmol) in t-BuOH (20 mL) at room temperature. After 15 min, a solution of 3-Bromo-4-oxiranyl-pyridine (200 mg, obtained above) in DMSO (10 mL) was added dropwise at 50° C. The resulting mixture was stirred at 50° C. for 15 h. The reaction mixture was quenched with brine, and the resulting mixture was extracted with ethyl acetate twice. The combined extracts were dried over anhydrous Na2SO4. After filtration and concentration, the residue was purified by flash column and afforded the title compound (96 mg). ESI-MS m/z: 216.1 [M+1]$^+$, Retention time 1.01 min; $^1$HNMR (CDCl$_3$, 400.342 MHz) δ ppm 2.50-2.59 (m, 1H), 3.31-3.39 (m, 1H), 4.65-4.70 (m, 1H), 4.87-4.92 (m, 1H), 5.91 (t, J=8 Hz, 1H), 7.95 (d, J=8 Hz, 1H), 8.68 (d, J=8 Hz, 1H), 8.73 (s, 1H).

Step 3: Synthesis of 3-methyl-5-(4-(oxetan-2-yl)pyridin-3-yl)benzo[d]oxazol-2(3H)-one

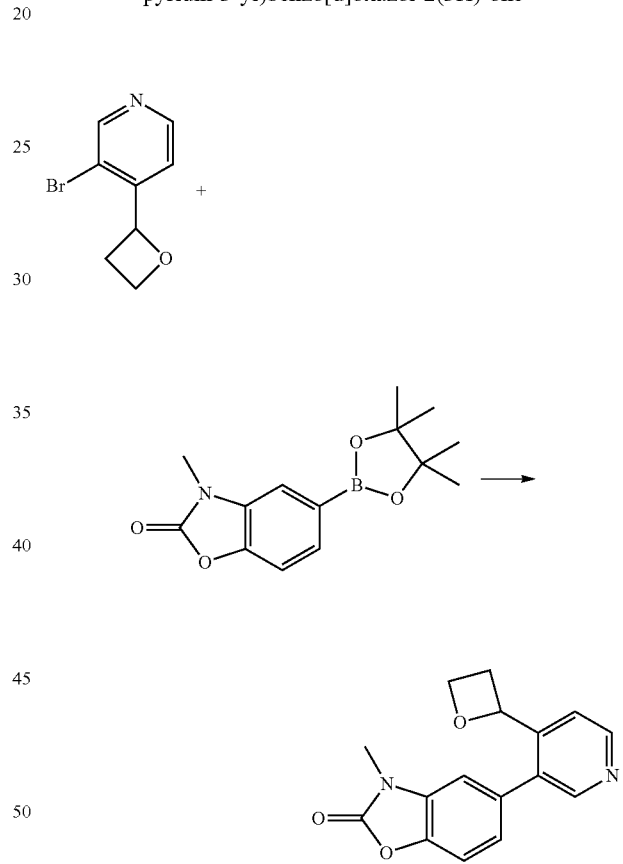

A mixture of 3-Methyl-5-(4,4,5,5-tetramethyl-[1,3,2]dioxaborolan-2-yl)-3H-benzooxazol-2-one (123 mg, 0.44 mmol), 3-Bromo-4-oxetan-2-yl-pyridine (96 mg, 0.44 mmol), Na2CO3 (2 M in water, 067 mL, 1.35 mmol) and PdCl2(PPh3)2 (16 mg, 0.02 mmol) in DMF (4 mL) was heated at 100° C. for 3 h. After concentration, the resulting residue was diluted with DCM and saturated NH4Cl solution. After filteration, the filtrates were concentrated and the residue was purified by flash column (MeOH/CH2Cl2, v/v, 0-3.5%) and afforded the title compound (6 mg, 5%); ESI-MS m/z: 283 [M+1]$^+$, Retention time 1.03 min; $^1$HNMR (MeOD, 400.342 MHz) δ ppm 2.60-2.65 (m, 1H), 2.83-2.87 (m, 1H), 3.47 (s, 3H), 4.62-4.68 (m, 1H), 4.75-4.82 (m, 1H), 5.91 (t, J=7.6 Hz, 1H), 7.06 (dd, J=8, 1.6 Hz, 1H), 7.15 (d, J=1.6 Hz, 1H), 7.39 (d, J=8 Hz, 1H), 7.94 (d, J=5.2 Hz, 1H), 8.46 (s, 1H), 8.67 (d, J=5.2 Hz, 1H).

Example 35

5-(4-(2-hydroxypropan-2-yl)pyridin-3-yl)-3-methyl-benzo[d]oxazol-2(3H)-one

Step 1: Synthesis of 2-(3-Bromo-pyridin-4-yl)-propan-2-ol

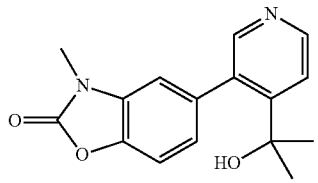 [SMILES: Cn1c(=O)oc2ccc(-c3cnccc3C(C)(C)O)cc21]

A solution of methylmagnesium bromide (3 M solution in THF, 1 mL, 3 mmol) was added dropwise to a solution of 1-(3-Bromo-pyridin-4-yl)-ethanone (200 mg, 1 mmol) in THF (3 mL) at −36° C. After addition, the resulting mixture was stirred for another 30 min at this temperature an was subsequently warmed up to 0° C. The reaction was quenched by saturated NH4Cl solution. The mixture was extracted with ethyl acetate. The combined extracts were dried over anhydrous MgSO4. After filtration and concentration, the title compound was obtained (217 mg), ESI-MS m/z: 218.0 [M+1]$^+$, Retention time 0.95 min.

Step 2: Synthesis of 5-(4-(2-hydroxypropan-2-yl) pyridin-3-yl)-3-methylbenzo[d]oxazol-2(3H)-one

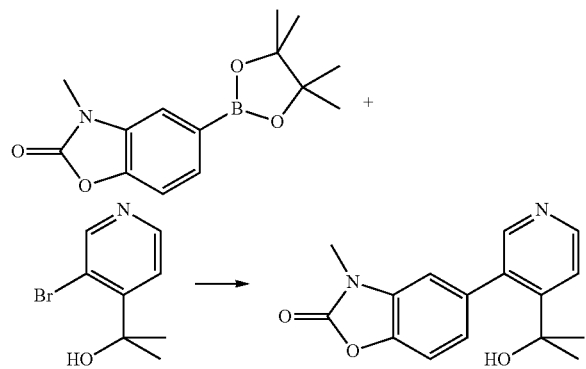

A mixture of 3-Methyl-5-(4,4,5,5-tetramethyl-[1,3,2]dioxaborolan-2-yl)-3H-benzooxazol-2-one (304 mg, 1.1 mmol), 2-(3-Bromo-pyridin-4-yl)-propan-2-ol (217 mg, 1.0 mmol), Na2CO3 (2 M in water, 1.5 mL, 3.0 mmol) and PdCl2(PPh3)2 (56 mg, 0.08 mmol) in DMF (6 mL) was heated at 100° C. for 4 hrs. After concentration, the residue was diluted with DCM and saturated NH4Cl solution. After filtration and concentration, the residue was purified by flash column (MeOH—CH2Cl2, v/v, 0-3.5%) to give the title compound (1.4 mg, 0.5%); ESI-MS m/z: 285 [M+1]$^+$, Retention time 0.98 min; $^1$H-NMR (CDCl3, 400 MHz) δ 1.51 (s, 6H), 3.43 (s, 3H), 6.95 (d, J=1.6 Hz, 1H), 7.04 (dd, J=8.4, 1.6 Hz, 1H), 7.32 (d, J=8.4 Hz, 1H), 8.11 (d, J=6.0 Hz, 1H), 8.40 (s, 1H), 8.65 (d. J=6.0 Hz, 1H).

Example 36

5-(5-fluoro-4-(hydroxymethyl)pyridin-3-yl)-3-methylbenzo[d]oxazol-2(3H)-one

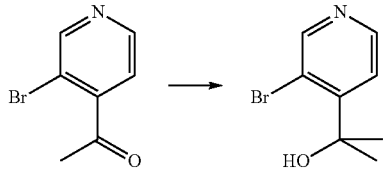

Step 1: Synthesis of 3-Brom-5-fluoro-pyridine-4-carbaldehyde

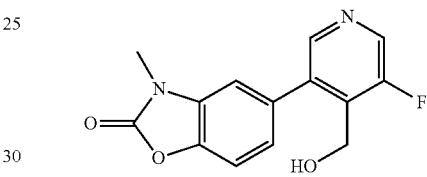

n-BuLi (1.6 M in hexanes, 2.250 mL, 3.60 mmol) was added dropwise to a solution of diisopropylamine (0.556 mL, 3.90 mmol) in THF (20 mL) at −78° C. under inert gas (N$_2$). The resulting mixture was warmed up to ~−50° C. and stirred for 10 min and cooled again to −78° C. A solution of 3-bromo-5-fluoropyridine (528 mg, 3 mmol) in THF (5 mL) was added dropwise at this temperature. The reaction mixture turned from clear light brown to heterogenous light brown. After 30 min, DMF (0.256 mL, 3.30 mmol) was added dropwise and the resulting mixture was stirred for 30 min. The reaction was quenched by MeOH then NH4Cl (saturated solution) and warmed up to room temperature. After concentration, the residue was dissolved in CH2Cl2 and washed with NaHCO3 (Saturated solution). After drying over Na2SO4, concentration, the residue was purified by column (Heptane to CH2Cl2) and yielded slightly yellow crystal (380 mg). $^1$H NMR (400.3 MHz, CDCl$_3$): δ 8.58 (s, 1H), 8.72 (s, 1H), 10.33 (s, 1H).

Step 2: Synthesis of 3-Fluoro-5-(3-methyl-2-oxo-2,3-dihydro-benzooxazol-5-yl)-pyridine-4-carbaldehyde

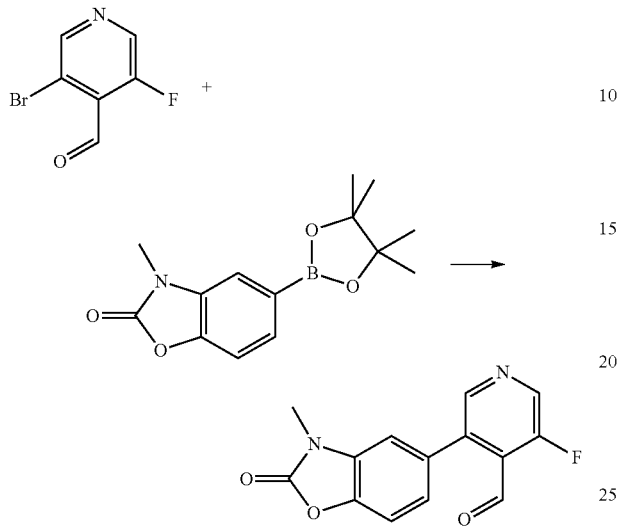

A mixture of 3-Methyl-5-(4,4,5,5-tetramethyl-[1,3,2]dioxaborolan-2-yl)-3H-benzooxazol-2-one (138 mg, 0.5 mmol), 3-Bromo-5-fluoro-pyridine-4-carbaldehyde (102 mg, 0.5 mmol), Na2CO3 (2 M in water, 0.75 mL, 1.5 mmol) and PdCl2(PPh3)2 (17 mg, 0.03 mmol) in DMF (3 mL) was heated at 100° C. for 4 hrs. After concentration, the residue was diluted with DCM and saturated NH4Cl solution. After filtration and concentration, the residue was purified by flash column (MeOH—CH2Cl2, v/v, 0-1.5%) and afforded the title compound (47 mg, 35%). $^1$H NMR (400.3 MHz, CDCl$_3$): δ 3.45 (s, 3H), 6.96 (d, J=1.7 Hz, 1H), 7.08 (dd, J=8, 1.7 Hz, 1H), 7.32 (d, J=8 Hz, 1H) 8.59 (s, 1H), 8.68 (d, J=1.3 Hz, 1H), 10.07 (s, 1H).

Step 3: Synthesis of 5-(5-fluoro-4-(hydroxymethyl)pyridin-3-yl)-3-methylbenzo[d]oxazol-2(3H)-one

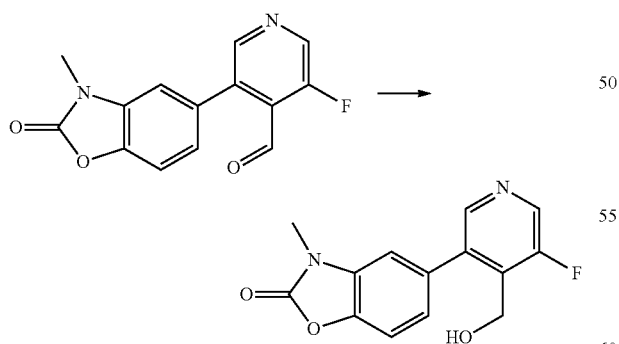

Sodium borohydride (6.3 mg, 0.17 mmol) was added to a solution of 3-Fluoro-5-(3-methyl-2-oxo-2,3-dihydro-benzooxazol-5-yl)-pyridine-4-carbaldehyde (47 mg, 0.17 mmol) in THF (0.5 mL) and water (0.1 mL) at 0° C. The resulting mixture was stirred at room temperature for 2 h. Brine was added to the reaction mixture. The resulting mixture was diluted with DCM and water. The organic layer was separated, dried over anhydrous Na2SO4 and concentrated under reduced pressure. The residue was purified by flash column (MeOH—CH2Cl2, v/v, 0-3%) and afforded the title compound (7 mg, 16%); ESI-MS m/z: 275 [M+1]$^+$, Retention time 0.92 min; $^1$HNMR (MeOD, 400.3 MHz) δ 3.44 (s, 3H), 4.59 (s, 2H), 7.32 (dd, J=8.0, 1.2 Hz, 1H), 7.35 (d, J=1.2 Hz, 1H), 7.38 (d, J=80 Hz, 1H), 8.39 (s, 1H), 8.48 (d, J=1.2 Hz, 1H).

Example 37

5-(4-(1-methoxyethyl)pyridin-3-yl)-3-methylbenzo[d]oxazol-2(3H)-one

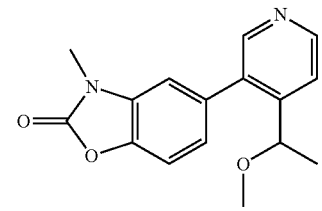 [SMILES: COC(C)c1ccncc1-c1ccc2oc(=O)n(C)c2c1]

Step 1: Synthesis of 3-Bromo-4-(1-methoxy-ethyl)-pyridine

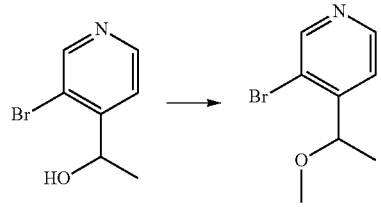

Sodium hydride (60% in mineral oil, 148 mg, 3.71 mmol) was added to a solution of 1-(3-bromopyridin-4-yl)ethanol (500 mg, 2.475 mmol) in DMF (12 mL) at 0° C. After 10 min, iodomethane (1.237 mL, 2.475 mmol) was added dropwise and the resulting mixture was stirred at room temperature for another 1 h. The reaction was quenched by water, and the mixture was extracted with ethyl acetate. The combined extracts were dried over anhydrous Na2SO4. After filtration and concentration, the residue was purified by flash column (ethyl acetate-heptane, v/v, 0-30%) to give 418 mg of the title compound. $^1$HNMR (CDCl3, 400.3 MHz) δ 1.42 (d, J=6.4 Hz, 3H), 3.30 (s, 3H), 4.64 (q, J=0.4 Hz, 1H), 7.58 (s, 1H), 8.56 (s, 1H), 8.70 9s, 1H).

Step 2: Synthesis of 5-(4-(1-methoxyethyl)pyridin-3-yl)-3-methylbenzo[d]oxazol-2(3H)-one

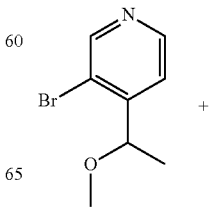

-continued

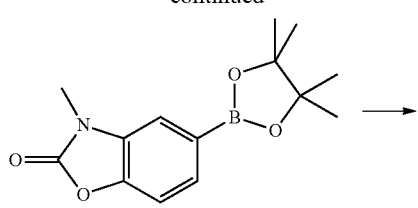

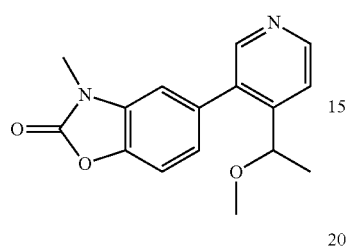

A mixture of 3-Methyl-5-(4,4,5,5-tetramethyl-[1,3,2]di-oxaborolan-2-yl)-3H-benzooxazol-2-one (255 mg, 0.93 mmol), 3-Bromo-4-(1-methoxy-ethyl)-pyridine (200 mg, 0.93 mmol), Na2CO3 (2 M in water, 1.6 mL, 0.8 mmol) and PdCl2(PPh3)2 (52 mg, 0.07 mmol) in DMF (3 was heated at 100"C for overnight. After concentration, the residue was diluted in DCM and saturated NH4Cl solution. After filtration and extraction, the combined extracts were dried over anhydrous Na2SO4. After filtration and concentration, the residue was purified by flash column (MeOH—CH2Cl2, v/v, 0-1.5%) to give the title compound (182 mg, 69%). The racemate was resolved by chiral HPLC (ChiralPak, IA-H column, 40% EtOH/Heptane) to the first peak (enantiomer 1, retention time=10.90 min) and the second peak (enantiomer 2, retention time 14.25 min). ESI-MS m/z: 285 [M+1]+, Retention time 1.13 min; $^1$HNMR (MeOD, 400 MHz) δ 1.38 (d, J=6.8 Hz, 3H), 3.30 (s, 3H), 3.48 (s, 3H), 4.69 (q, J=6.8 Hz, 1H), 7.27 (dd, J=8.0, 1.6 Hz, 1H), 7.32 (d, J=1.6 Hz, 1H), 7.45 (d, J=8.0 Hz, 1H), 8.25 (d, J=6.0 Hz, 1H), 8.78 (s, 1H), 8.89 (id, J=6.0 z, 1H).

Example 38

5-(4-(1-amino-2,2,2-trifluoroethyl)pyridin-3-yl)-3-methylbenzo[d]oxazol-2(3H)-one

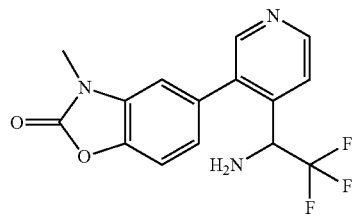 [SMILES: Cn1c(=O)oc2ccc(-c3cnccc3C(N)C(F)(F)F)cc21]

The entitled compound was synthesized using procedures described in example 30. Enantiomers were obtained by employing either enantiomers of the commercially available 2-Methyl-propane-2-sulfinic acid amide in the synthesis. ESI-MS m/z: 324 [M+1]+, Retention time 1.13 min; $^1$H-NMR (MeOD, 400 MHz) δ 343 (s, 3H), 4.57 (q, J=7.6 Hz, 1H), 7.14 (dd, J=8.0, 1.6 Hz, 1H), 7.20 (d J=1.6 Hz, 1H), 7.38 (d, J=80 Hz, 1H), 7.78 (d J=5.2 Hz, 1H), 8.50 (s, 1H), 8.63 (d, J=5.2 Hz, 1H).

Example 39

Ethanesulfonic acid [5-(2-oxo-3-propyl-2,3-dihydro-benzooxazol-5-yl)-pyridin-3-yl]-amide

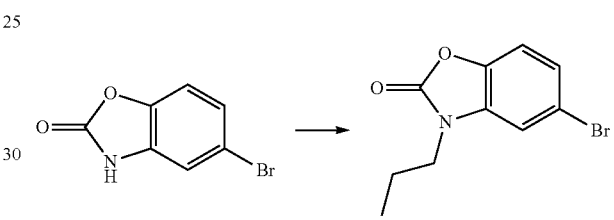

Step 1: Synthesis of 5-Bromo-3-propyl-3H-benzooxazol-2-one

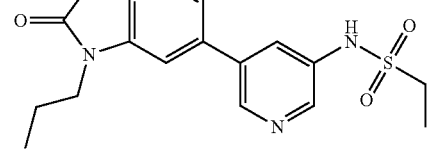

A 100 mL round-bottomed flask was charged with 5-bromo-2-benzoxazolinone (0.750 g, 3.50 mmol), n-propyl iodide (0.684 mL, 7.01 mmol), potassium carbonate (1.211 g, 8.76 mmol) and Dioxane (5 mL). The reaction mixture was stirred at room temperature for overnight. The reaction was quenched with water. Colorless precipitate was collected through filtration and 5-Bromo-3-propyl-3H-benzooxazol-2-one was obtained, ESI-MS: m/z 258.2 (M+H)+

Step 2: Synthesis of 3-propyl-5-(4,4,5,5-tetramethyl-[1,3,2]dioxaborolan-2-yl)-3H-benzooxazol-2-one

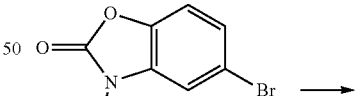

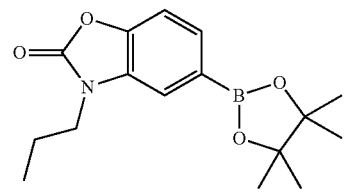

A 100 mL round bottom flask was charged with 5-Bromo-3-propyl-3H-benzooxazol-2-one (716 mg, 2.80 mmol), 4,4,4',4',5,5,5',5'-octamethyl-2,2'-bi(1,3,2-dioxaborolane) (785 mg, 3.09 mmol) and dioxane (15 mL). To this mixture PdCl2

(dppf).CH2Cl2 (51.4 mg, 0.084 mmol) was added. The reaction mixture was stirred at 90° C. for overnight. The reaction was cooled to room temperature and concentrated in vacuo. The residue was purified by silica gel flash chromatography (Ethyl acetate-Heptane, v/v, 10-90 to 50-50) to afford pure product 3-propyl-5-(4,4,5,5-tetramethyl-[1,3,2]dioxaborolan-2-yl)-3H-benzooxazol-2-one as a light cream color solid. m/z 304.3 (M+H)+

Step 3: Synthesis of ethanesulfonic acid [5-(2-oxa-3-propyl-2,34-dihydro-benzooxazol-5-yl)-pyridin-3-yl]-amide

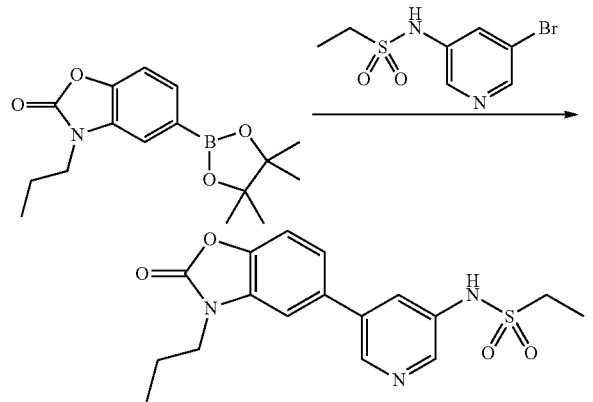

A 20 mL microwave vial was charged with 3-propyl-5-(4,4,5,5-tetramethyl-[1,3,2]dioxaborolan-2-yl)-3H-benzooxazol-2-one (0.258 g, 0.852 mmol), ethanesulfonic acid (3-bromo-phenyl)-amide (0.150 g, 0.568 mmol), sodium carbonate (2 M in water, 0.852 mL 1.704 mmol) and Dioxane (5 ml). The reaction mixture was flushed and evacuated with N2 twice, then tetrakis(triphenylphosphine)palladium(0) (65.6 mg, 0.057 mmol) was added and the vial was evacuated and flushed with N2 again. The reaction mixture was stirred in the microwave at 100° C. for 2 hrs. The reaction mixture was concentrated in vacuo. The residue was dissolved in DMSO (3.5 mL) and purified by using Xbridge C18 eluting with a 10 to 100% ACN-water to afford pure product ethanesulfonic acid [5-(2-oxo-3-propyl-2,3-dihydro-benzooxazol-5-yl)-pyridin-3-yl]-amide as a white color solid. ESI-MS: m/z 362.2 (M+H), $^1$H NMR (400 MHz, MeOD) 5 ppm 1.04 (t, J=7.5 Hz, 3H), 1.39 (t, J=7.3 Hz, 3H), 1.83-1.96 (m, 2H), 3.24 (d, J=7.3 Hz, 2 H), 3.95 (t, J=7.1 Hz, 2H), 7.42 (d, J=8.3 Hz, 1H), 7.46 (dd. J=8.3, 1.8 Hz, 1H), 7.53 (d, 5 Hz, 1H), 7.97 (t, J=21 Hz, 1H), 8.44 (d, J=2.3 Hz, 1H), 8.58 (d, J=2.0 Hz, 1H). HRMS: (ESI) m/z 362.11745 [(M+H)+ Calcd for C17H19N3O4S 362.11691].

Example 40

Ethanesulfonic acid [5-(3-ethyl-2-oxo-2,3-dihydro-benzooxazol-5-yl)-pyridin-3-yl]-amide

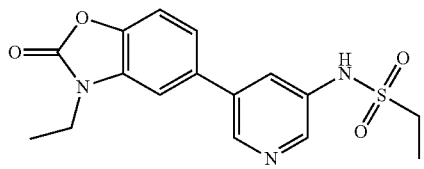 [SMILES: CCn1c(=O)oc2ccc(-c3cncc(NS(=O)(=O)CC)c3)cc21]

The entitled compound was synthesized using procedure described in example 39. ESI-MS: m/z 348.2 (M+H)+, 1H NMR (400 MHz, MeOD) δ ppm 1.39 (t, J=7.5 Hz, 3H), 1.43 (t, J=7.2 Hz, 3H) 3.21 (q, J=7.3 Hz, 2H), 4.03 (q, J=7.2 Hz, 2H), 7.41 (d J=8.3 Hz, 1H), 7.45 (dd, J=8.3, 1.8 Hz, 1H), 7.53 (d, J=1.3 Hz, 1H), 7.94 (t, J=2.1 Hz, 1H), 8.41 (d, J=2.5 Hz, 1H), 8.51 (d, J=2.0 Hz, 1H). HRMS: (ESI) m/z 348.10245 [(M+H)+ Calcd for C16H17N3O4S 348.10126].

It can be seen that the compounds of the invention are useful as inhibitors of aldosterone synthase activity and therefore useful in the treatment of diseases and conditions mediated by aldosterone synthase such as the metabolic disorders disclosed herein.

It will be understood that the invention has been described by way of example only and modifications may be made whilst remaining within the scope and spirit of the invention.

The invention claimed is:
1. A compound of Formula I:

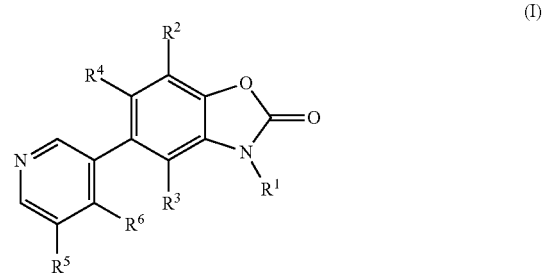

(I)

or a pharmaceutically acceptable salt thereof, wherein:
R$^1$ is C$_{1-7}$alykl, C$_{6-10}$aryl-C$_{1-7}$alkyl, hydroxy-C$_{1-7}$alkyl, or C$_{3-8}$cycloalkyl;
R$^2$ and R$^4$ are each independently hydrogen or halogen;
R$^3$ is hydrogen or C$_{1-7}$alkoxy;
R$^5$ is hydrogen, halogen, C$_{1-7}$alkoxy, C$_{1-7}$alkyl, C$_{3-8}$cycloalkyl, cyano, —CH$_2$NR$^8$R$^9$, —CH$_2$NR$^8$(SO$_2$)—C$_{1-7}$alkyl, —CH$_2$NR$^8$(SO$_2$)—C$_{3-8}$cycloakyl, —NR$^8$(SO$_2$)—C$_{1-7}$alkyl, —NR$^8$(SO$_2$)—C$_{3-8}$cycloalkyl or —NHC(O)NR$^8$R$^9$; in which each alkyl and cycloalkyl is optionally substituted with one or more substitutents selected from the group consisting of C$_{1-7}$alkoxy, halogen, hydroxy, —NH$_2$, —NH(C$_{1-7}$alkyl) and —N(C$_{1-7}$alkyl)$_2$;
R$^6$ is hydrogen, C$_{1-7}$alkyl, C$_{3-8}$cycloalkyl, heterocyclyl, —C(O)—C$_{1-7}$alkyl, —C(O)NR$^8$R$^9$, —C$_{1-7}$alkyl-NR$^8$C(O)—C$_{1-7}$alkyl, —CH$_2$NR$^8$(SO$_2$)—C$_{1-7}$alkyl, —C$_{1-7}$alkyl-NR$^8$—S(O)$_n$—C$_{1-7}$alkyl, —CH$_2$NR$^8$—S(O)$_n$—C$_{3-8}$cycloalkyl or —CH$_2$NR$^8$(SO$_2$)—C$_{1-7}$alkyl; in which each alkyl and cycloalkyl is optionally substituted with one or more substituents selected from the group consisting of C$_{6-10}$aryl, C$_{1-7}$alkoxy, halogen, hydroxy and —NH$_2$, —NH(C$_{1-7}$alkyl) and —N(C$_{1-7}$alkyl)$_2$; and
R$^8$ and R$^9$ are each independently hydrogen, C$_{1-7}$alkyl or C$_{6-10}$aryl-C$_{1-7}$alkyl; and n is 1 or 2;
wherein each heteroaryl is a mono- or bicyclic aromatic moiety comprising 5-10 ring atoms selected from carbon atoms and 1 to 5 heteroatoms, and
each heterocyclyl is a mono- or bicyclic saturated or partially saturated but non-aromatic moiety comprising 4-10 ring atoms selected from carbon atoms and 1 to 5 heteroatoms; and each heteratoms being O, N or S.

2. The compound according to claim 1, wherein:
$R^3$, $R^2$ and $R^6$ are H;
$R^5$ is hydrogen, halogen, $C_{1-7}$ alkyl or $C_{3-8}$cycloalkyl in which alkyl and cycloalkyl are optionally substituted with one or more substituents selected from the group consisting of $C_{1-7}$alkoxy, halogen, hydroxy, —NH$_2$, —NH($C_{1-7}$alkyl) and —N($C_{1-7}$alkyl)$_2$, or a pharmaceutically acceptable salt thereof.

3. The compound according to claim 1, wherein $R^5$ is selected from the group consisting of:

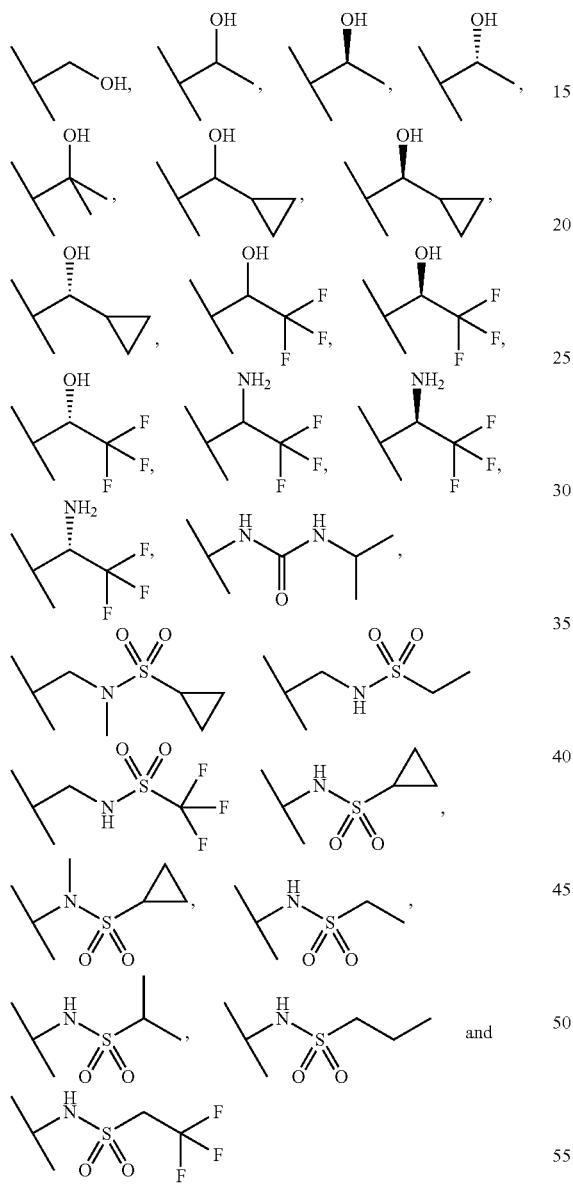

or a pharmaceutically acceptable salt thereof.

4. The compound according to claim 1, wherein:
$R^3$, $R^2$ and $R^5$ are H;
$R^4$ is hydrogen or halogen;
$R^6$ is H, halogen, $C_{7-7}$alkyl or $C_{3-8}$cycloalkyl in which alkyl and cycloalkyl are optionally substituted with one or more substituents selected from the group consisting of $C_{6-10}$aryl, $C_{1-7}$alkoxy, halogen, hydroxy and —NH$_2$, —NH($C_{1-7}$alkyl) and —N($C_{1-7}$alkyl)$_2$, or a pharmaceutically acceptable salt thereof.

5. The compound according to claim 1, wherein:
$R^6$ is selected from the group consisting of:

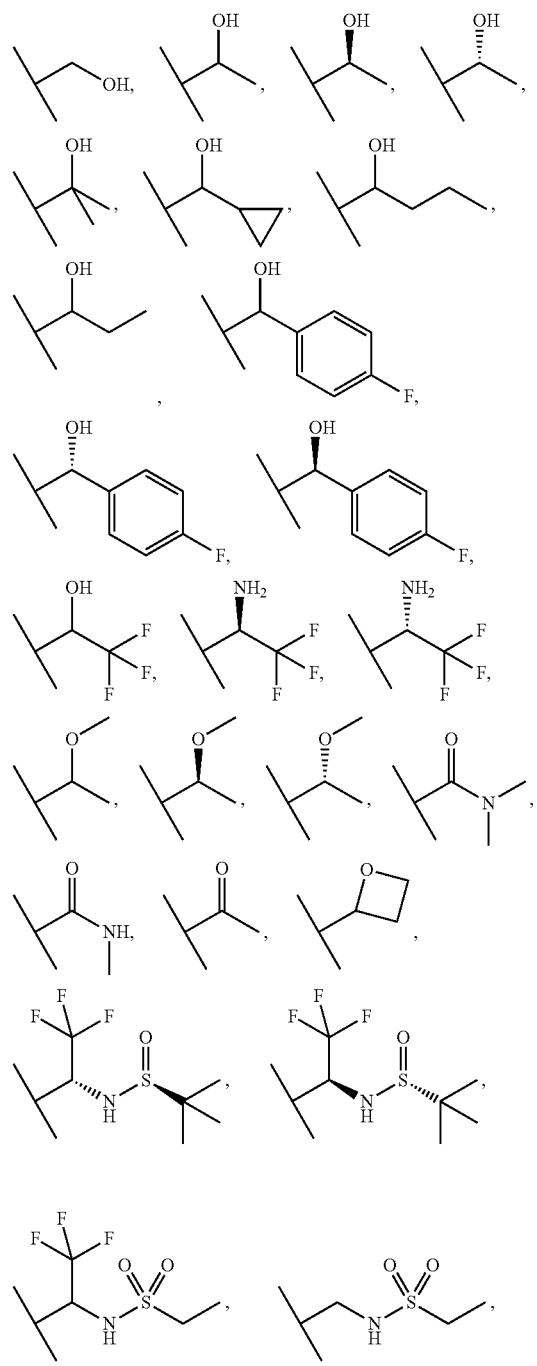

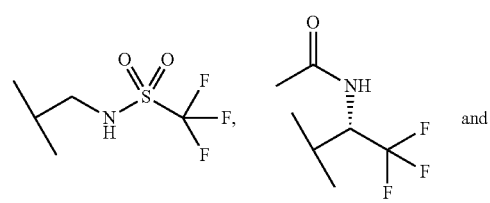

-continued

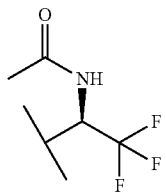

or a pharmaceutically acceptable salt thereof.

6. The compound according to claim 1; wherein:
$R^4$ is H;
$R^6$ is $C_{1-7}$alkyl substituted with hydroxy, or a pharmaceutically acceptable salt thereof.

7. A pharmaceutical composition comprising a therapeutically effective amount of the compound according to claim 1, or a pharmaceutically acceptable salt thereof, and one or more pharmaceutically acceptable carriers.

8. A pharmaceutical combination, comprising a therapeutically effective amount of the compound according to claim 1, or a pharmaceutically acceptable salt thereof, and one or more therapeutically active agents selected from an HMG-Co-A reductase inhibitor, an angiotensin II receptor antagonist, angiotensin converting enzyme (ACE) Inhibitor, a calcium channel blocker (CCB), a dual angiotensin converting enzyme/neutral endopeptidase (ACE/NEP) inhibitor, an endothelin antagonist, a renin inhibitor, a diuretic, an ApoA-I mimic, an anti-diabetic agent, an obesity-reducing agent, an aldosterone receptor blocker, an endothelin receptor blocker and a CETP inhibitor.

9. A method of inhibiting aldosterone synthase activity in a subject having hypertension, comprising: administering to the subject a therapeutically effective amount of the compound according to claim 1, or a pharmaceutically acceptable salt thereof.

10. A method of treating a disorder or a disease mediated by aldosterone synthase, in a subject having said disorder or disease, comprising: administering to the subject a therapeutically effective amount of the compound according to claim 1, or a pharmaceutically acceptable salt thereof, wherein said disorder or disease is hypertension.

* * * * *